(12) United States Patent
Crow et al.

(10) Patent No.: US 9,809,854 B2
(45) Date of Patent: Nov. 7, 2017

(54) BIOMARKERS FOR DISEASE ACTIVITY AND CLINICAL MANIFESTATIONS SYSTEMIC LUPUS ERYTHEMATOSUS

(71) Applicant: NEW YORK SOCIETY FOR THE RUPTURED AND CRIPPLED MAINTAINING THE HOSPITAL, New York, NY (US)

(72) Inventors: Mary K. Crow, New York, NY (US); Mikhail Olferiev, Mount Kisco, NY (US)

(73) Assignee: NEW YORK SOCIETY FOR THE RUPTURED AND CRIPPLED MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 345 days.

(21) Appl. No.: 13/998,598

(22) Filed: Nov. 15, 2013

(65) Prior Publication Data
US 2014/0135225 A1    May 15, 2014

Related U.S. Application Data

(60) Provisional application No. 61/726,902, filed on Nov. 15, 2012.

(51) Int. Cl.
*C12Q 1/68* (2006.01)
(52) U.S. Cl.
CPC ..... *C12Q 1/6883* (2013.01); *C12Q 2600/158* (2013.01)
(58) Field of Classification Search
None
See application file for complete search history.

(56) References Cited

U.S. PATENT DOCUMENTS

| | | | | |
|---|---|---|---|---|
| 7,571,055 | B2 * | 8/2009 | Behrens | C12Q 1/6883 435/6.11 |
| 2010/0113293 | A1 * | 5/2010 | Pascual | C12Q 1/6883 506/8 |
| 2010/0261172 | A1 * | 10/2010 | Yao | C12Q 1/6883 435/6.12 |

OTHER PUBLICATIONS

Manzi et al. "Systemic Lupus Erythematosus: Treatment and Assessment" in Klippel et al., Primer on the Rheumatic Diseases, 13th ed. (New York, Springer, 2008), pp. 327-338.*
Affymetrix HG-U133A Annotation File (filtered excerpt, obtained from <http://www.affymetrix.com/Auth/analysis/downloads/na35/ivt/HG-U133A.na35.annot.csv.zip> on Apr. 29, 2016, 1 page).*
Mannucci et al. (2003) Von Willebrand factor cleaving protease (ADAMTS-13) in 123 patients with connective tissue diseases Journal of Hematology, 88(8):914-918.*
Whitehead et al. (2005) Variation in tissue-specific gene expression among natural populations. Genome Biology, 6:R13.*
Villanueva et al. (2011) Netting Neutrophils Induce Endothelial Damage, Infiltrate Tissues, and Expose Immunostimulatory Molecules in Systemic Lupus Erythematosus. The Journal of Immunology, 187:538-552.*
Bijl et al. (2001) Fas expression on peripheral blood lymphocytes in systemic lupus erythematosus (SLE): relation to lymphocyte activation and disease activity. Lupus, 10:866-872.*
Crow et al. (2003) Microarray analysis of gene expression in lupus. Arthritis Research and Therapy, 5:279-287.*
Baechler et al. (2003) Interferon-inducible gene expression signature in peripheral blood cells of patients with severe lupus. PNAS, 100(5):2610-2615.*
GeneCards database entry for IFIT3 (obtained from <http://www.genecards.org/cgi-bin/carddisp.pl?gene=IFIT3> on May 26, 2016, 15 pages).*
Navarra et al. (2011) Efficacy and safety of belimumab in patients with active systemic lupus erythematosus: a randomised, placebo-controlled, phase 3 trial. The Lancet, 377:721-731.*
Abramson et al. (1983) Arthritis Rheum. 26:630-6.
American College of Rheumatology Ad Hoc Committee on Systemic Lupus Erythematosus Response Criteria (2004) Arthritis Rheum. 50:3418-26.
Baechler et al. (2003) Proc Natl Acad Sci USA 100:2610-5.
Barrat et al. (2005) J. Exp. Med. 202:1131-9.
Bauer et al. (2009) Arthritis Rheum. 60:3098-107.
Bennett et al. (2003) J. Exp. Med. 197:711-23.
Brinkmann et al. (2004) Science 303:1532-5.
Chaussabel et al. (2008) Immunity 29:150-64.
Crow and Kirou (2008) Arthritis Res. Ther. 10:126.
Crow (2007) Curr. Top. Microbiol. Immunol. 316:359-86.
Crow and Wohlgemuth (2003) Arthritis Res. Ther. 5:279-87.
Crow et al. (2003) Autoimmunity 36:481-90.
Denny et al. (2010) J. Immunol. 6:3284-97.
De Waard et al.(1999) Gene 226:1-8.
Fan et al. (2004) Genome Res. 14:878-85.
Feng et al. (2006) Arthritis Rheum. 54:2951-62.
Forsman and Dahlgren (2010) BMC Cell Biol. 11:52.
Fukuda et al. (2009) Clin. Rheumatol. 28:301-4.
Garcia-Carrasco et al. (2002) J. Rheumatol. 29:726-30.
Garcia-Romo et al. (2011) Sci. Trans. Med. 3:73ra20.
Gray et al. (2010) J. Immunol. 184:6359-66.
Hakkim et al. (2010) Proc Natl Acad Sci USA 107:9813-8.
Han et al. (2003) Genes Immun.4:177-86.
Hargraves et al. (1948) Mayo Clin. Proc. 23:25-8.
Hargraves (1969) Mayo Clin. Proc. 44:579-9.

(Continued)

*Primary Examiner* — Neil P Hammell
(74) *Attorney, Agent, or Firm* — Leason Ellis LLP

(57) ABSTRACT

This invention related to methods and assays for screening for, identifying, and predicting the severity and clinical manifestations of systemic lupus erythematosus (SLE). Specifically, this invention provides various biomarkers for the prediction of flares of the disease both in number and severity, as well as clinical manifestations of the disease, and methods of using these biomarkers to correctly subclassify patients with this disease, and prescribe appropriate treatment. The invention also provides for biomarkers of lupus disease activity, i.e., flares, as well as biomarkers for the prediction of future flares, and methods of using these biomarkers. The invention also provides, in these biomarkers, targets and methods for drug development and basic research for SLE.

6 Claims, 17 Drawing Sheets
(5 of 17 Drawing Sheet(s) Filed in Color)

(56) References Cited

OTHER PUBLICATIONS

Irizarry et al. (2003) Biostatistics 4:249-64.
Karlovich et al. (2009) BMC Med. Genomics.2:33.
Kirou et al. (2004) Arthritis Rheum. 50:3958-67.
Kurien and Scofield (2006) Scand. J. Immunol. 64:227-35.
Kurien et al. (2000) Clin. Exp. Immunol.120:209-17.
Lande et at. (2011) Sci. Transl. Med.3:73ra19.
Lovgren et al. (2004) Arthritis Rheum. 50:1861-72.
Mantovani et al. (1998) Ann. N Y Acad. Sci.840:338-51.
Milner and Day (2003) J. Cell. Sci. 116:1863-73.
Nathan (2006) Nat. Rev. Immunol. 6:173-82.
Samarajiwa et al. (2009) Nucleic Acids Research (Database Issue):D852-7.
Tan et at. (1982) Arthritis Rheum. 25:1271-7.
Theilgaard-Mönch et al. (2005) Blood 105:1785-96.
Velculescu et at. (1995) Science 270;484-487.
Velculescu et al. (1997) Cell 88.
Villanueva et al. (2011) J. Immunol. 187:538-52.
Yee et al. (2009) Rheumatology 48:691-5.
Zhao et al. (2009) Drug Metab. Dispos.37:282-91.

* cited by examiner

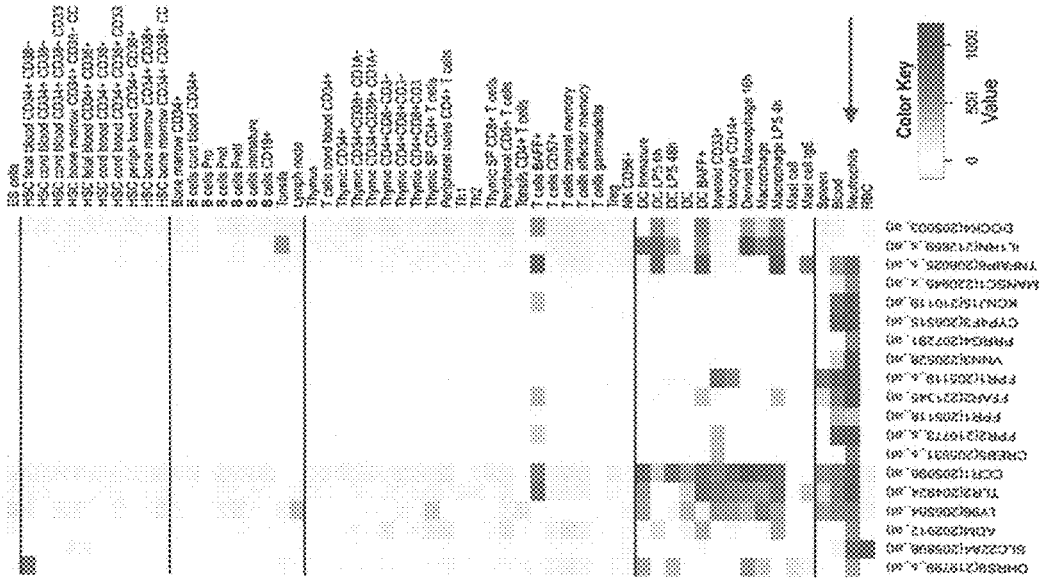
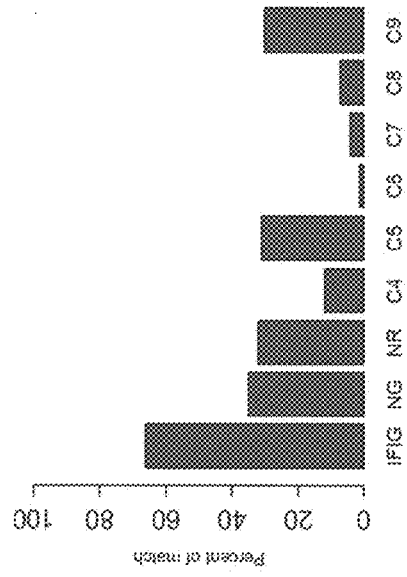
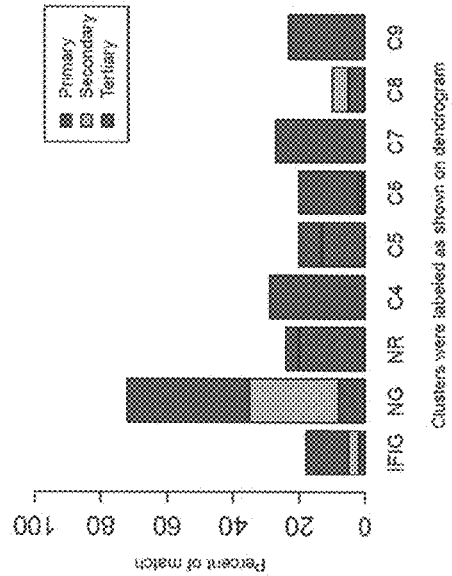
Figure 2A
Figure 2B
Figure 2C

BIOMARKERS FOR DISEASE ACTIVITY AND CLINICAL MANIFESTATIONS SYSTEMIC LUPUS ERYTHEMATOSUS

CROSS REFERENCE TO RELATED APPLICATION

The present application claims priority to U.S. Patent Application Ser. No. 61/726,902 filed Nov. 15, 2012, which is hereby incorporated by reference in its entirety.

FIELD OF THE INVENTION

This invention relates to the field of screening for, identifying, and predicting the severity and clinical manifestations of systemic lupus erythematosus (SLE). Specifically, this invention provides various biomarkers for the prediction of flares of the disease both in number and severity, as well as clinical manifestations of the disease, and methods of using these biomarkers to correctly subclassify patients with this disease, and prescribe appropriate treatment. The invention also provides for biomarkers of lupus disease activity, i.e., flares, as well as biomarkers for the prediction of future flares, and methods of using these biomarkers.

The invention also provides targets for drug development and basic research for SLE.

BACKGROUND OF THE INVENTION

Systemic lupus erythematosus (SLE), also known as lupus, is an autoimmune illness.

Although there are several different forms of lupus, the classical lupus patient is usually a young woman with a combination of symptoms, such as fever, swollen lymph glands, rashes (particularly butterfly-shaped rashes on the face), arthritis, fatigue, hair loss, chest and/or abdominal pain, oral ulcers, and neuropsychiatric problems, such as headache, memory loss, mood disorders, and/or confusion.

While the cause of lupus is unknown, theories on its origin include genetics, environment, infections, and the defective failure to process the products of an immune response. Although it is a lifelong condition, symptoms tend to cycle in alternate periods of flares and remission. Those with lupus are at great risk of contracting kidney disease as well.

Treatment options include corticosteroids, anti-malarial drugs, immunosuppressive drugs such as mycophenolate mofetil, cytotoxic agents such as cyclophosphamide, non-steroidal anti-inflammatory drugs (NSAIDs), and certain biologics, such as belimumab, rituximab, and others.

The American College of Rheumatology has established criteria that is used for studies, but can also aid in the diagnosis. If four or more of the eleven criteria occur, a patient may have SLE. These criteria are:

1. Malar rash (rash on cheeks);
2. Discoid rash (red, scaly patches on skin that cause scarring);
3. Photosensitivity;
4. Oral ulcers;
5. Nonerosive arthritis of two or more peripheral joints, with tenderness, swelling, or effusion;
6. Pleuritis or pericarditis;
7. Renal disorder as evidenced by more than 0.5 g per day protein in urine or cellular casts seen in urine under a microscope;
8. Neurologic disorder such as seizures or psychosis;
9. Hematalogic disorder such as hemolytic anemia (low red blood cell count) or leukopenia (white blood cell count<4000/µl);
10. Immunologic disorder including positive anti-smith, anti-ds DNA, anti-phospholipid antibody, and/or false positive serological test for syphilis; and
11. Positive anti-nuclear antibody (ANA) test.

Currently, a number of tests are performed to aid in establishing a diagnosis of SLE in the context of the characteristic symptoms and signs of SLE. These include: antinuclear antibody (ANA) blood test; anti-double stranded DNA test; anti-Smith antibody test; VDRL, a syphilis test; complete blood count (CBC); blood chemistry levels; inflammatory markers—the erythrocyte sedimentation rate (also called the ESR) and C-reactive protein; x-rays of joints; and a biopsy from the skin or kidneys.

At this time there is no definitive diagnostic test for SLE, or any tests that predict the course and severity of the disease or which organs the disease is most likely to affect. Moreover, genetic testing is not routinely performed in order to diagnose SLE. Thus, there is a real need in the art for definitive tests to determine the severity of a patient's SLE, including the number and severity of flares of the disease. Moreover, with the vast number of etiologies of the disease, as well as the number of therapies used for treatment, a test that provides information on which organs and organ systems the disease will most affect would be useful. Better knowledge as to targets to concentrate upon when testing for drugs, as well as when performing basic research on SLE would be of great value as well.

The biomarkers described herein provide not only a novel and unique way to definitively screen, identify, and predict the severity, activity, and clinical manifestations of SLE, but provide a number of markers for use in drug screening and research, and basic research on SLE.

SUMMARY OF THE INVENTION

This invention is based upon the surprising discovery that changes in expression in three sets of signature genes correlate to the severity of disease activity and clinical manifestations in subjects with SLE. Using the differences in expression of genes in three sets of signature genes, interferon inducible ("IFIG"), neutrophil granule, and neutrophil-related, SLE patients can be categorized into five groups. These five groups differ by the severity of the disease including the number of, and severity of flares, as well as the clinical manifestations. Additionally, certain protein markers can confirm these classifications. These categories are useful for the health care provider in determining treatment options, and the amount and type of monitoring a patient diagnosed with SLE may need. Genetic testing in combination with testing for protein markers is a novel method for determining the severity and etiology of a subject's SLE, and can be used to determine the course of treatment and amount of monitoring of the subject, often prior to any identifiable symptoms. This early identification of disease activity and clinical manifestations is invaluable in providing proper patient care especially given the unpredictability of SLE.

Thus, one embodiment of the present invention is a method and/or assay for screening, identifying and/or predicting the severity and clinical manifestation of systemic lupus erythematosus in a subject, comprising obtaining biological tissue and/or fluid from the subject, purifying and/or isolating nucleic acid, including, but not limited to, mRNA and cDNA, from the biological tissue and/or fluid, detecting the expression of one or more genes in the IFIG signature, listed in Table 2, and comparing the expression of the gene or genes with the expression of the gene or genes in a healthy control, wherein an increase in expression of one or more genes from the IFIG signature could indicate an increase in flares, an increase in severe flares, and an increase in mucocutaneous manifestation of the disease.

A more preferred embodiment of the present invention is a method and/or assay for screening, identifying and/or predicting the severity and clinical manifestation of systemic lupus erythematosus in the subject, comprising obtaining biological tissue and/or fluid from a subject, purifying and/or isolating nucleic acid, including, but not limited to, mRNA and cDNA, from the biological tissue and/or fluid, and detecting the expression of one or more genes in the IFIG signature, listed in Table 2, and one or more genes in the neutrophil granule signature, listed in Table 3, and comparing the expression of the gene or genes with the expression of the gene or genes in a healthy control, wherein an increase in expression of one or more genes from the IFIG signature and the neutrophil granule signature would indicate an increase in the number of flares, an increase in the number of severe flares, and an increase in vascular and renal manifestations of the disease.

Another preferred embodiment of the present invention is a method and/or assay for screening, identifying and/or predicting the severity and clinical manifestation of systemic lupus erythematosus in the subject, comprising obtaining biological tissue and/or fluid from a subject, purifying and/or isolating nucleic acid, including, but not limited to, mRNA and cDNA, from the biological tissue and/or fluid, and detecting the expression of one or more genes in the IFIG signature, listed in Table 2, and one or more genes in the neutrophil-related signature, listed in Table 4, and comparing the expression of the gene or genes with the expression of the gene or genes in a healthy control, wherein an increase in expression of one or more genes from the IFIG signature and the neutrophil-related signature would indicate an increase in the number of flares, and an increase in mucocutaneous manifestation of the disease.

A further embodiment of the invention is a method and/or assay for screening, identifying and/or predicting the severity and clinical manifestation of systemic lupus erythematosus in a subject, comprising obtaining biological tissue and/or fluid from the subject, purifying and/or isolating nucleic acid, including, but not limited to, mRNA and cDNA, from the biological tissue and/or fluid, and detecting the expression of one or more genes in the IFIG signature, listed in Table 2, and one or more genes in the neutrophil granule signature, listed in Table 3, and comparing the expression of the gene or genes with the expression of the gene or genes in a healthy control, purifying and isolating protein from the biological tissue and/or fluid, and detecting the presence of anti-SSA/Ro autoantibodies, wherein an increase in expression of one or more genes from the IFIG signature and the neutrophil granule signature, and the presence of the anti-SSA/Ro autoantibodies would indicate an increase in the number of flares, an increase in the number of severe flares, and an increase in vascular and renal manifestation of the disease.

A more preferred embodiment of the present invention is a method and/or assay for screening, identifying and/or predicting the severity and clinical manifestation of systemic lupus erythematosus in a subject, comprising obtaining biological tissue and/or fluid from the subject, purifying and/or isolating nucleic acid, including, but not limited to mRNA and cDNA, from the biological tissue and/or fluid, and detecting the expression of one or more genes in the IFIG signature, listed in Table 2, and one or more genes in the neutrophil-related signature, listed in Table 4, and comparing the expression of the gene or genes with the expression of the gene or genes in a healthy control, purifying and isolating protein from the biological tissue and/or fluid, and detecting the presence of TNFα, IL-8, and IL-18, wherein an increase in expression of one or more genes from the IFIG signature and the neutrophil-related signature, and the presence of TNFα, IL-8, and IL-18, would indicate an increase in the number of flares, and an increase in mucocutaneous manifestation of the disease.

Another embodiment of the present invention is a method of treating a subject with SLE comprising obtaining biological tissue and/or fluid from the subject, purifying and/or isolating nucleic acid, including, but not limited to, mRNA and cDNA, from the biological tissue and/or fluid, and detecting the expression of one or more genes in the IFIG signature, listed in Table 2, and one or more genes in the neutrophil granule signature, listed in Table 3, and comparing the expression of the gene or genes with the expression of the gene or genes in a healthy control, wherein an increase in expression of one or more genes from the IFIG signature and the neutrophil granule signature would indicate treating the subject with agents for the treatment of vascular and renal manifestations of SLE, including, but not limited to, corticosteroids, such as prednisone in a medium to high dose (7.5 to over 30 mg/day), or intravenous methylprednisolone in a high doses (known as pulse therapy, using greater than 50 mg/day for 1-3 days); cytotoxic drugs, such as cyclophosphamide; immunosuppressive drugs, such as mycophenolate mofetil and azathioprine; biologic agents, such as rituximab; and anti-malarial drugs, such as hydroxychloroquine, as well as agents targeting the vascular system, including but not limited to anti-hypertensive drugs, statins, and anti-coagulants, such as aspirin and coumarin, and monitoring the subject often, e.g., at least monthly, possibly weekly.

Another embodiment of the present invention is a method of treating a subject with SLE comprising obtaining biological tissue and/or fluid from the subject, purifying and/or isolating nucleic acid, including, but not limited to, mRNA and cDNA, from the biological tissue and/or fluid, and detecting the expression of one or more genes in the IFIG signature, listed in Table 2, and one or more genes in the neutrophil granule signature, listed in Table 3, and comparing the expression of the gene or genes with the expression of the gene or genes in a healthy control, purifying and isolating protein from the biological tissue and/or fluid, and detecting the presence of anti-SSA/Ro autoantibodies, wherein an increase in expression of one or more genes from the IFIG signature and the neutrophil granule signature, wherein an increase in expression of one or more genes from the IFIG signature and the neutrophil granule signature, and the presence of the anti-SSA/Ro autoantibodies would indicate treating the subject with agents for the treatment of vascular and renal manifestations of SLE, including, but not limited to, corticosteroids such as prednisone in a medium to high dose (7.5 to over 30 mg/day), or intravenous methylprednisolone in a high doses (known as pulse therapy, using greater than 50 mg/day for 1-3 days); cytotoxic drugs, such as cyclophosphamide; immunosuppressive drugs, such as mycophenolate mofetil and azathioprine; biologic agents, such as rituximab; and anti-malarial drugs, such as hydroxychloroquine, as well as agents targeting the vascular system, including but not limited to anti-hypertensive drugs, statins, and anti-coagulants, such as aspirin and coumarin, and monitoring the subject often, e.g., at least monthly, possibly weekly.

Another preferred embodiment of the present invention is a method for treating a subject with SLE comprising obtaining biological tissue and/or fluid from a subject, purifying and/or isolating nucleic acid, including, but not limited to, mRNA and cDNA, from the biological tissue and/or fluid, and detecting the expression of one or more genes in the IFIG signature, listed in Table 2, and one or more genes in the neutrophil-related signature, listed in Table 4 and comparing the expression of the gene or genes with the expression of the gene or genes in a healthy control, wherein an increase in expression of one or more genes from the IFIG signature and the neutrophil-related signature would indicate treating the subject with agents for the treatment of mucocutaneous manifestation of the disease, including but not limited to, corticosteroids, such as prednisone in a low to medium dose (less than 20 mg/day); anti-malarial medications, such as hydroxychloroquine, and immunosuppressive agents, such as azathioprine, dapsone, and thalidomide, as well as topical agents that target mucocutaneous disorders, including but not limited to, topical corticosteroids. These subjects would typically be monitored less than monthly, e.g., quarterly, and would be especially counseled to avoid sunlight.

Another preferred embodiment of the present invention is a method for treating a subject with SLE comprising obtaining biological tissue and/or fluid from a subject, purifying and/or isolating nucleic acid, including but not limited to mRNA and cDNA from the biological tissue and/or fluid, and detecting the expression of one or more genes in the IFIG signature, listed in Table 2, and one or more genes in the neutrophil-related signature listed in Table 4 and comparing the expression of the gene or genes with the expression of the gene or genes in a healthy control, purifying and isolating protein from the biological tissue and/or fluid, and detecting the presence of TNFα, IL-8, and/or IL-18, wherein an increase in expression of one or more genes from the IFIG signature and the neutrophil-related signature and the presence of TNFα, IL-8, and/or IL-18 would indicate treating the subject with agents for the treatment of mucocutaneous manifestation of the disease, including but not limited to, corticosteroids, such as prednisone in a low to medium dose (less than 20 mg/day); anti-malarial medications, such as hydroxychloroquine, and immunosuppressive agents, such as azathioprine, dapsone, and thalidomide, as well as topical agents that target mucocutaneous disorders, including but not limited to, topical corticosteroids. These subjects would typically be monitored less than monthly, e.g., quarterly, and would be especially counseled to avoid sunlight.

It should be noted that the major benefit from these methods of treatment is that they could be started prior to any overt symptoms in the subject.

Another embodiment of the invention is method of and/or assay for monitoring subjects with SLE for their responses to treatment, in both the regular care of the subject, e.g., administration of a known therapeutic agent and lifestyle changes, as well as in clinical trials of test agents. This method and/or assay comprises obtaining biological tissue and/or fluid from a subject prior to treatment, purifying and/or isolating nucleic acid, including, but not limited to, mRNA and cDNA, from the biological tissue and/or fluid, and detecting the expression of one or more genes in the IFIG signature, listed in Table 2, and/or detecting the expression of one or more genes in the neutrophil granule signature listed in Table 3, and/or one or more genes in the neutrophil-related signature listed in Table 4 prior to the treatment, administering a therapeutic agent, or a test agent, or other treatment, detecting the expression of the same gene or genes after treatment, and comparing the gene expression prior to treatment to the gene expression after treatment, wherein a decrease in gene expression after treatment as compared to the gene expression prior to treatment, indicates that the therapeutic agent or test agent or other treatment is effectively treating or ameliorating the subject's SLE.

A further embodiment would include purifying and isolating protein from the biological tissue and/or fluid, and detecting the presence of TNFα, IL-8, and/or IL-18, and/or anti-SSA/Ro autoantibodies, prior to and after treatment, wherein a decrease in the level or amount of protein after treatment indicates that the therapeutic agent or test agent or other treatment is effectively treating or ameliorating the subject's SLE.

In all of the preceding methods and assays, a preferred embodiment is that expression from more than one gene from a signature would be detected and/or measured. For the IFIG signature, 1 to 83 genes can be detected and/or measured, with IFIT1 and IFIT3, being preferred. For the neutrophil granule signature, 1 to 24 genes can be detected and/or measured with OLFM4, CRISP3, IFI27, DEFA4, MMP8, ANXA3, ARG1, MPO, DEFA1, LTF, and CEACAM6 being preferred. For the neutrophil-related signature, 1 to 23 genes, can be detected and/or measured, with TNFAIP6, FPR1, FPR2, LY96, CYP4F3, IL1R2, PRRG4, and DOCK4, being preferred.

A most preferred embodiment of the present invention is a method and/or assay that comprise all five components.

It will also be understood that proteins and polypeptides encoded by any of the genes listed in Tables 2, 3, and 4 can be detected and/or measured in all of the preceding methods and/or assays as a way of detecting and/or measuring gene expression.

Additionally, the invention also relates to the surprising discovery that differential expression of genes in at least three signatures in an SLE patient along with increased von Willebrand factor (vWF) and IL-10 mark the active disease state, i.e., flares.

Thus, a further embodiment of the present invention is a method and/or assay for monitoring subjects with SLE for their responses to treatment, in both the regular care of the subject, e.g., administration of a known therapeutic agent and lifestyle changes, as well as in clinical trials of test agents. This method and/or assay comprises obtaining biological tissue and/or fluid from a subject prior to treatment, purifying and/or isolating nucleic acid, including, but not limited to, mRNA and cDNA, from the biological tissue and/or fluid, and detecting the expression of one or more genes in the IFIG signature, listed in Table 2, and/or detecting the expression of one or more genes in the neutrophil granule signature, listed in Table 3, and/or one or more genes in the plasma cell signature listed in Table 5 prior to the treatment, administering a therapeutic agent, or a test agent or other treatment, detecting the expression of the same gene or genes, and comparing the gene expression prior to treatment to the gene expression after treatment, wherein a decrease in gene expression after treatment as compared to the gene expression prior to treatment, indicates that the therapeutic agent or test agent or other treatment is effectively treating or ameliorating the subject's SLE. Preferably, plasma proteins, von Willebrand factor (vWF) and IL-10 are also monitored.

In all of the preceding methods and assays, a preferred embodiment is that expression from more than one gene from a signature would be detected and/or measured. For the IFIG signature, 1 to 83 genes can be detected and/or measured, with IFIT1 and IFIT3, being preferred. For the neutrophil granule signature, 1 to 24 genes can be detected and/or measured with OLFM4, CRISP3, IFI27, DEFA4, MMP8, ANXA3, ARG1, MPO, DEFA1, LTF, and CEACAM6 being preferred. For the plasma cell signature, 1 to 45 genes, can be detected and/or measured, with CD38, being preferred.

Additionally, the invention also relates to the surprising discovery that differential expression of genes in four signatures in an SLE patient when not flaring, indicates increased number of future flares.

Thus, a further embodiment of the present invention is a method and/or assay for predicting future flares in a subject with SLE, who is not flaring, comprising obtaining biological tissue and/or fluid from the subject, purifying and/or isolating nucleic acid, including but not limited to mRNA and cDNA from the biological tissue and/or fluid, detecting the expression of the expression of one or more genes in the IFIG signature, listed in Table 2, and/or detecting the expression of one or more genes in the neutrophil granule signature listed in Table 3, and/or one or more genes in the plasma cell signature listed in Table 5, and/or one or more genes in the T-cell/iNKT signature listed in Table 6, and comparing the expression of the genes with the expression of the genes in a healthy control, wherein an increase in expression the genes in the first three signatures and a decrease in the expression of the gene in the last signature, indicates an increase in future flares.

Yet another embodiment is a method of treating a subject with SLE comprising obtaining biological tissue and/or fluid from the subject, purifying and/or isolating nucleic acid, including but not limited to mRNA and cDNA from the biological tissue and/or fluid, detecting the expression of detecting the expression of the expression of one or more genes in the IFIG signature, listed in Table 2, and/or detecting the expression of one or more genes in the neutrophil granule signature listed in Table 3, and/or one or more genes in the plasma cell signature listed in Table 5, and/or one or more genes in the T-cell/iNKT signature listed in Table 6, and comparing the expression of the genes with the expression of the genes in a healthy control, wherein an increase in expression the genes in the first three signatures and a decrease in the expression of the gene in the last signature, indicates consideration of treating the patient with agents including, but not limited to, corticosteroids, such as prednisone in a medium to high dose (7.5 to over 30 mg/day), or intravenous methylprednisolone in a high doses (known as pulse therapy, using greater than 50 mg/day for 1-3 days); cytotoxic drugs, such as cyclophosphamide; immunosuppressive drugs, such as mycophenolate mofetil and azathioprine; biologic agents, such as rituximab; and anti-malarial drugs, such as hydroxychloroquine, as well as increasing the dose of any therapeutic agents currently be used by the subject, and monitoring the subject more frequently, e.g., monthly or more frequently.

In all of the preceding methods and assays, a preferred embodiment is that expression from more than one gene from a signature would be detected and/or measured. For the IFIG signature, 1 to 83 genes can be detected and/or measured, with IFIT1 and IFIT3, being preferred. The neutrophil granule signature, 1 to 24 genes can be detected and/or measured with OLFM4, CRISP3, IFI27, DEFA4, MMP8, ANXA3, ARG1, MPO, DEFA1, LTF, and CEACAM6 being preferred. For the plasma cell signature, 1 to 48 genes, can be detected and/or measured, with CD38, being preferred. For the T-cell/iNKT gene signature, 1 to 20 can be detected and/or measured with KLRB 1 being preferred.

A preferred embodiment detects the expression of IFIT3, KLRB1, CD38, and MMP8.

Determining the expression of any of the genes in any of the signatures can be done by any method known in the art, including, but not limited to, microarrays; Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

The expression of the genes from the subject with SLE can be compared to a reference value of the expression of the same genes in a healthy control. The levels of expressed genes may be measured as absolute or relative. Absolute quantitation measure concentrations of specific RNA and requires a calibration curve. Relative quantification measures fold change differences of specific RNA in comparison to housekeeping genes. Relative quantification is usually adequate to investigate physiological changes in gene expression levels. One reference value that can be used in the methods and assays of the invention is the fold change between patients with SLE and healthy donors of expression of each differentially expressed gene found in Table 9.

Detection of the levels of anti-SSA/Ro autoantibodies, TNFα, IL-8, and IL-18, and vWF and IL-10, can be accomplished by any method known in the art, including methods which result in qualitative results, such as ones where the existence of the protein can be visualized, either by the naked eye or by other means, and/or quantitative results. Such methods would include, but are not limited to, quantitative Western blots, immunoblots, quantitative mass spectrometry, enzyme-linked immunosorbent assays (ELISAs), radioimmunoassays (RIA), immunoradiometric assays (IRMA), and immunoenzymatic assays (IEMA) and sandwich assays using monoclonal and polyclonal antibodies. Reference values of fold change of proteins between patients with SLE and healthy donors is found in Table 10.

The present invention also provides for methods and tools for drug design, testing of agents, and tools for basic research into the causes and etiology of systemic lupus erythematosus.

One embodiment is a method and/or assay for screening and/or identifying a test agent for the prevention and/or treatment of SLE, comprising contacting or incubating the test agent with a polypeptide encoded by one of the genes listed in Tables 2, 3, 4, 5 or 6, and detecting the presence of a complex between the test agent, wherein if a complex between the test agent and the polypeptide is detected, the test agent is identified as a prevention and/or treatment for SLE.

A further embodiment is a method and/or assay for screening and/or identifying a test agent for the prevention and/or treatment of SLE, comprising contacting or incubating the test agent with a polypeptide encoded by one of the genes listed in Tables 2, 3, 4, 5, or 6 and a known ligand of the polypeptide, and detecting the presence of a complex between the test agent and the ligand, wherein if a complex between the test agent and the ligand is detected, the test agent is identified as a prevention and/or treatment for SLE.

Another embodiment of the present invention is a method and/or assay for screening and/or identifying a test agent for the prevention and/or treatment of SLE, comprising contacting or incubating the test agent with a polypeptide encoded by one of the genes listed in Tables 2, 3, 4, 5, or 6 and a known antibody of the polypeptide, and detecting the presence and quantity of unbound antibody, wherein the presence of the unbound antibody indicates that the test agent is binding to the polypeptide, and the test agent is identified as a prevention and/or treatment for SLE.

These methods and assays can be done using polypeptides TNFα, IL-8, IL-18, vWF, and IL-10. They can be performed with the polypeptides and test agents, and ligands and antibodies, if applicable, free in solution, or affixed to a solid support. The polypeptides and antibodies may be labeled by any method known in the art.

High throughput screening can also be used to screen the test agents. Small peptides or molecules can be synthesized and bound to a surface and contacted with the polypeptides encoded by the gene signature transcripts, and washed. The bound peptide is visualized and detected by methods known in the art.

A further embodiment of the present invention is a method and/or assay for screening and/or identifying a test agent for the prevention and/or treatment of SLE comprising is contacting or incubating a test agent to a nucleotide comprising any one of the genes listed in Tables 2, 3, 4, 5, or 6, and determining if the test agent binds to the gene, wherein if the test agent binds to the nucleotide, the test agent is identified as a therapeutic or preventative agent for SLE.

A further embodiment of the present invention is a method and/or assay for screening and/or identifying a test agent for the prevention and/or treatment of SLE comprising contacting or incubating a test agent with a nucleotide comprising any one of the genes listed in Tables 2, 3, 4, 5, or 6 which expresses a measurable phenotype, and measuring the phenotype before and after contact or incubation with the test agent, wherein if the expression of the measurable phenotype is decreased after the contact or incubation with the test agent, the test agent is identified as a therapeutic or preventative agent for SLE.

The measurable phenotype can be one that is native to the gene or one that is artificially linked, such as a reporter gene.

A further embodiment of the present invention is a method and/or assay for screening and/or identifying a test agent for the prevention and/or treatment of SLE, comprising transforming a host cell with a gene construct comprising any gene listed in Tables 2, 3, 4, 5 or 6, detecting the expression of the gene in the host cell, contacting the test agent with the host cell, and detecting the expression of the gene from the host cell after contact with the test agent or compound, wherein if the expression of the gene is reduced or decreased after contact with the test agent or compound, the test agent is identified as a therapeutic or preventative agent for SLE.

The present invention also provides a method for determining target genes or proteins for drug development and basic research regarding SLE. The invention also contemplates that the protein products of any of the genes in the gene signatures found in Tables 2-6 would also be potential therapeutic targets drug development or research.

The present invention also includes kits.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

The patent or application file contains at least one drawing executed in color. Copies of this patent or patent application publication with color drawing(s) will be provided by the Office upon request and payment of the necessary fee.

FIG. 2 depicts the assignment of transcripts, in which expression is different in PBMC of SLE patients, to functional groups of genes. FIG. 2A is the graphical results of analyzing the top cluster in the dendrogram of FIG. 1 using INTERFEROME. FIG. 2B shows the graphical results of analysis done on the second from top cluster in FIG. 1, labeled "NG" based upon previously published microarray analysis of bone marrow and peripheral blood neutrophils by Theilgaard-Mönch et al. 2005. FIG. 2C shows the results of analysis of the third cluster from the top of the dendrogram in FIG. 1 labeled "NR" using a Gene Enrichment Profiler from Harvard University containing data from human normal primary tissues (126 tissues represented by 557 microarrays). Expression profiles were processed to identify tissue specificity which is measured by an enrichment score.

FIG. 3 depicts graphs of the average plasma levels of autoantibodies and pro-inflammatory proteins among three major groups of SLE patients during the study.

FIG. 6 shows graphs of disease activities in groups of SLE patients based on hierarchical clustering and frequency of visits per year.

FIG. 9 are graphs of the comparison of the 4-gene microarray score and vWF plasma level as compared to flares in three representative SLE patients (IF06, IF09, and IF12).

DETAILED DESCRIPTION OF THE INVENTION

Definitions

Figure 1:
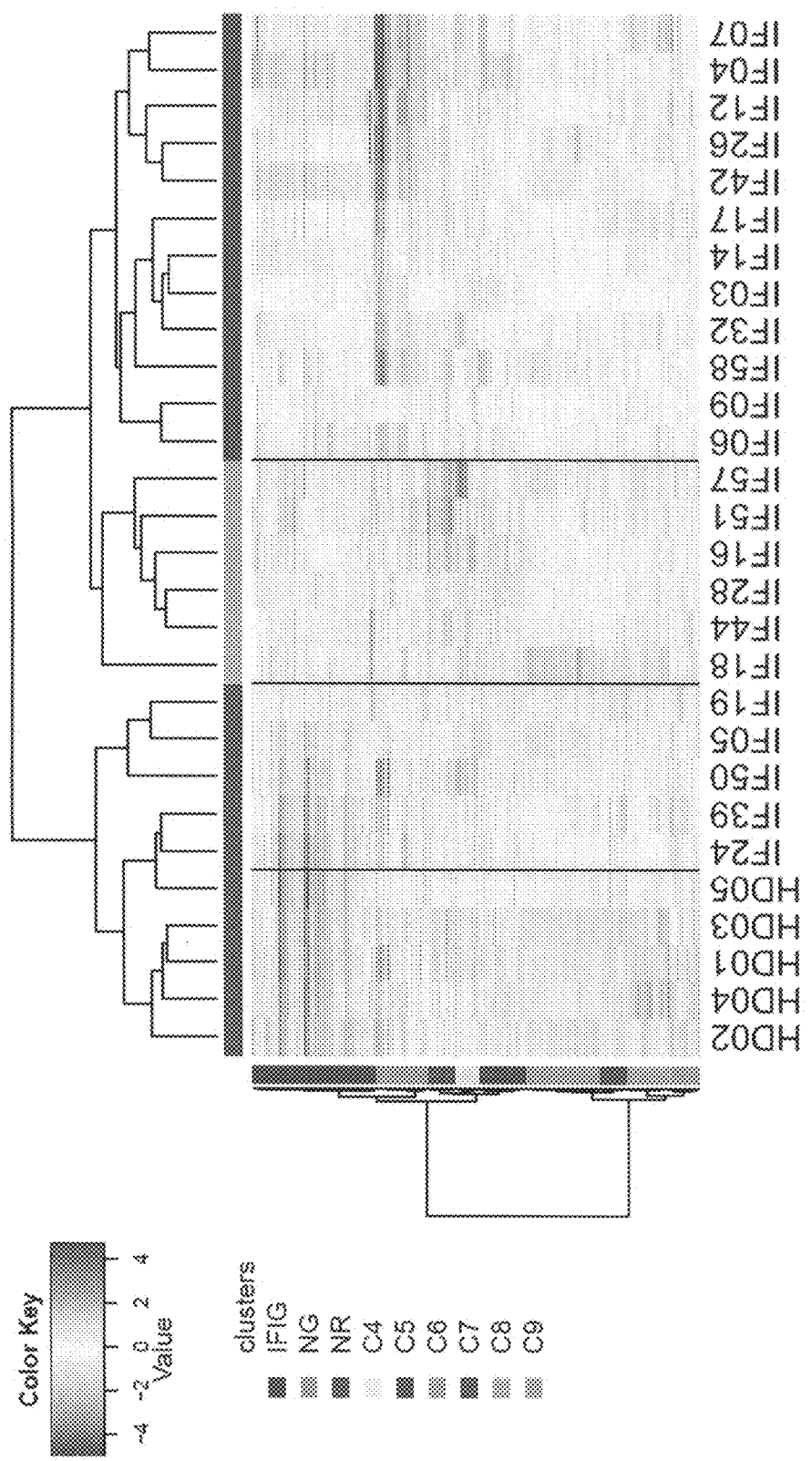
FIG. 1 is a heatmap and dendrogram showing the unsupervised hierarchical clustering of donors (shown in the columns) and differentially expressed mRNA transcripts (shown in the rows). Heatmap codes mean levels of expression for each probe-set, calculated over all visits for each study subject before clustering, Unsupervised hierarchical clustering is shown based on 433 mRNA transcripts differentially expressed in SLE and HD PBMC (FC>1.5, p<0.05, 5% FDR). The first three groups of transcripts from the top of dendrogram were identified as follows: IFIG—interferon inducible genes, NG—neutrophil granules related, and NR—neutrophil related. SLE patients (identified as IF#) were classified based on the dendrogram as follows: (A) linked with healthy donors (identified as HD#)—shown mostly in blue; (B) showing increase in IFN and NR genes—blue turning to yellow and orange; and (C) showing increase in IFN and NG genes—mostly yellow with orange.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is one suffering with systemic lupus erythematosus.

The terms "systemic lupus erythematosus" and "SLE" and "lupus" will be used interchangeably herein and is defined as a systemic autoimmune disease that can affect any part of the body. As occurs in other autoimmune diseases, the immune system attacks the body's cells and tissue, resulting in inflammation and tissue damage. SLE most often harms the heart, joints, skin, lungs, blood vessels, liver, kidneys, and nervous system. The course of the disease is unpredictable, with periods of illness (called flares) alternating with remissions.

The terms "SLE disease activity index" and "SLEDAI" and "SELENA SLEDAI" are used interchangeably in this application and means the weighted cumulative index of lupus disease activity (American College of Rheumatology Ad Hoc Committee on Systemic Lupus Erythematosus Response Criteria 2004). The total score falls between 0 and 105, with higher scores representing increased disease activity. The SLEDAI has been shown to be a valid and reliable disease activity measure in multiple patient groups, and has also has been shown to be sensitive to changes in disease activity in children.

The terms "British Isles Lupus Assessment Group Index 2000" and "BILAG" are used interchangeably in this application. BILAG is a score which accounts for disease activity in eight systems.

The terms "screen" and "screening" and the like as used herein means to test a subject or patient to determine if they have a particular illness or disease, or a particular manifestation of an illness or disease. The term also means to test an agent to determine if it has a particular action or efficacy.

The terms "identification", "identify", "identifying" and the like as used herein means to recognize a disease state or a clinical manifestation or severity of a disease state in a subject or patient. The term also is used in relation to test agents and their ability to have a particular action or efficacy.

The terms "prediction", "predict", "predicting" and the like as used herein means to tell in advance based upon special knowledge.

The term "reference value" as used herein means an amount or a quantity of a particular protein or nucleic acid in a sample from a healthy control or healthy donor.

The terms "healthy control", "healthy donor" and "HD" are used interchangeably in this application and are a human subject who is not suffering from systemic lupus erythematosus or any other rheumatic or autoimmune disease.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

As used herein, the term "isolated" and the like means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, an isolated genomic DNA, or a restriction fragment. In another embodiment, an isolated nucleic acid is preferably excised from the chromosome in which it may be found. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated material may be, but need not be, purified.

The term "purified" and the like as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The terms "expression profile" or "gene expression profile" refers to any description or measurement of one or more of the genes that are expressed by a cell, tissue, or organism under or in response to a particular condition. Expression profiles can identify genes that are up-regulated, down-regulated, or unaffected under particular conditions. Gene expression can be detected at the nucleic acid level or at the protein level. The expression profiling at the nucleic acid level can be accomplished using any available technology to measure gene transcript levels. For example, the method could employ in situ hybridization, Northern hybridization or hybridization to a nucleic acid microarray, such as an oligonucleotide microarray, or a cDNA microarray. Alternatively, the method could employ reverse transcriptase-polymerase chain reaction (RT-PCR) such as fluorescent dye-based quantitative real time PCR (TaqMan® PCR). In the Examples section provided below, nucleic acid expression profiles were obtained using Affymetrix GeneChip® oligonucleotide microarrays. The expression profiling at the protein level can be accomplished using any available technology to measure protein levels, e.g., using peptide-specific capture agent arrays.

The terms "gene signature" and "signature genes" will be used interchangeably herein and mean the particular transcripts that have been found to be differentially expressed in some SLE patients.

The terms "gene", "gene transcript", and "transcript" are used somewhat interchangeable in the application. The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. "Transcript" or "gene transcript" is a sequence of RNA produced by transcription of a particular gene. Thus, the expression of the gene can be measured via the transcript.

The term "antisense DNA" is the non-coding strand complementary to the coding strand in double-stranded DNA.

The term "genomic DNA" as used herein means all DNA from a subject including coding and non-coding DNA, and DNA contained in introns and exons.

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an antiparallel hybrid).

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA which codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct" or "gene construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described herein.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

"Nucleic acid" refers to deoxyribonucleotides or ribonucleotides and polymers thereof in either single- or double-stranded form. The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, and carbamates) and with charged linkages (e.g., phosphorothioates, and phosphorodithioates). Polynucleotides may contain one or more additional covalently linked moieties, such as, for example, proteins (e.g., nucleases, toxins, antibodies, signal peptides, and poly-L-lysine), intercalators (e.g., acridine, and psoralen), chelators (e.g., metals, radioactive metals, iron, and oxidative metals), and alkylators. The polynucleotides may be derivatized by formation of a methyl or ethyl phosphotriester or an alkyl phosphoramidate linkage. Modifications of the ribose-phosphate backbone may be done to facilitate the addition of labels, or to increase the stability and half-life of such molecules in physiological environments. Nucleic acid analogs can find use in the methods of the invention as well as mixtures of naturally occurring nucleic acids and analogs. Furthermore, the polynucleotides herein may also be modified with a label capable of providing a detectable signal, either directly or indirectly. Exemplary labels include radioisotopes, fluorescent molecules, and biotin.

The term "polypeptide" as used herein means a compound of two or more amino acids linked by a peptide bond. "Polypeptide" is used herein interchangeably with the term "protein."

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Genes and Proteins Correlated to Clinical Outcomes of Systemic Lupus Erythematosus Patients with systemic lupus erythematosus (SLE) have variable manifestations and outcomes. This comprehensive molecular analysis of patients with SLE and healthy donors (HD) has identified subgroups of patients, primarily defined based on presence or absence of mRNA transcript signatures, and has described significant relationships between those patient groups, and clinical and serologic features of lupus. The results set forth herein for the first time provide biochemical and genetic biomarkers for clinical outcomes of SLE that will allow prediction of disease severity, which in turn allows for correct treatment choice at a much earlier stage in the disease, even before symptoms occur. Furthermore, these biochemical and genetic biomarkers will allow a complete understanding of the mechanism of SLE, and provide targets for testing new drugs and therapies for SLE.

Additionally, using the same data, biomarkers were also identified which correlate to disease activity, i.e., flare activity, and future flare activity.

As shown in the Examples 1-5, peripheral blood mononuclear cells (PBMC) and plasma samples from visits were collected longitudinally (up to 3 years) from numerous SLE patients and 5 healthy donors. PBMC mRNA profiles for each visit were established using Affymetrix GeneChips®. Plasma levels of 44 autoantibodies and 41 pro-inflammatory mediators were determined using Multi-Analyte Profiling technology. A linear mixed model was used to identify differentially expressed genes and clustering analysis was used for patient classification and transcript classification.

The gene signatures in SLE blood, type I interferon inducible genes (IFIG) and neutrophil granule genes, along with neutrophil-related genes, classified SLE patients into 5 distinct groups. Patients with neither signature had only mild disease, and no particular clinical manifestation. The other groups had more frequent flares, but were distinguishable based on gene expression, clinical manifestations, and cytokine profile.

Each group with its identifying signature and clinical manifestations is found in Table 1.

traps (NETs) (Brinkmann et al. 2004) has suggested potential relevance to lupus. This process may be important in the formation of anti-nuclear autoantibodies, endothelial damage and autoimmune inflammation. Immune complexes that include anti-RNP antibodies can induce NET formation and those NETs contribute to activation of endosomal TLRs and production of IFN-I by plasmacytoid dendritic cells (pDC) (Lande et al. 2011; Garcia-Romo et al. 2011).

Group B2 SLE patients showed differential expression of a less well-defined cluster of genes that includes TNFAIP6, FPR1, FPR2, LY96, CYP4F3, IL1R2, PRRG4, and DOCK4. This group of genes is denoted as neutrophil-related or neutrophil activation signature genes. Increased expression of representative transcripts in this cluster by group B2 patients was confirmed by real-time-PCR. Based on tissue expression analysis and literature review, a common theme among those transcripts is increased expression by neutrophils in peripheral blood (FIG. 2C), and thus, they represent a second neutrophil-related signature in SLE patients.

TNFAIP6 (Tumor necrosis factor-inducible gene 6 or TSG6), the gene transcript in this cluster that showed the greatest fold increase, is a member of the hyaluronan-binding protein family and is associated with inflammation

TABLE 1

Summary of Five Groups of SLE Patients

|  | IFIG | Neutrophil granule gene signature | Neutrophil-related gene signature | Increased TNFα, IL-8, IL-18 | Increased anti-SSA/Ro autoantibodies | Increased Flares | Increased severe flares | Mucocutaneous Involvement | Vascular Involvement |
|---|---|---|---|---|---|---|---|---|---|
| A |  |  |  |  |  |  |  |  |  |
| B1 | X |  |  | X |  |  |  | X |  |
| B2 | X |  | X | X |  | X |  | X |  |
| C1 |  | X |  |  | X | X | X |  | X |
| C2 | X | X |  |  | X | X | X |  | X |

The IFIG signature is a feature of groups B1, B2, and C2. Transcripts associated with the neutrophil granule gene signature represented the most striking differentiating signature associated with groups C1 and C2, suggesting an important pathogenic role for the products of neutrophil granules in those patient groups, and were also associated with flare. Neutrophil-specific transcripts were represented by genes encoding proteins present in primary azurophilic granules and expressed at highest level in the bone marrow during myelopoiesis (Nathan 2006).

A role for neutrophils in the pathogenesis of SLE has a long history, beginning with observations of so-called "Lupus Erythematosus (LE)" cells present in the bone marrow of most SLE patients (up to 80%) (Hargraves et al. 1948). The formation of LE cells is initiated when anti-nuclear autoantibodies penetrate neutrophils and interact with nuclear material, resulting in loss of nuclear structure. The degraded nuclei are engulfed by nearby polymorphonuclear leukocytes (Hargraves 1969). Later, Abramson and colleagues pointed to the capacity of lupus sera to induce neutrophil aggregation, particularly in patients with active central nervous system disease (Abramson et al. 1983).

The importance of neutrophils in SLE has re-emerged with the description of the presence of low-density granulocytes in blood preparations from many lupus patients and the recognition that those cells produce IFN and are associated with endothelial cell damage (Denny et al. 2010). The discovery of NETosis, the process in which neutrophils extrude intracellular material containing chromatin that forms web-like structures called neutrophil extracellular in arthritis models (Milner and Day 2003). Formyl peptide receptor 1 and 2 (FPR1 and FPR2) are G-protein-coupled receptors highly expressed on neutrophils that recognize damage-related mitochondrial peptides and DNA, as well as microbial peptides and acute phase protein serum amyloid A (SAA) (Forsman and Dahlgren 2010). Engagement of FPR1 or FPR2 by their ligands activates neutrophil granulation. Ly96, also known as MD-2, participates with TLR4 in binding of lipopolysaccharide (LPS) (Gray et al. 2010). Induction of CYP4F3, a cytochrome P450 enzyme, regulates leukotriene B(4) metabolism in neutrophils (Zhao et al. 2009). IL1R2 receptor, induced by oxygen radicals and other stimuli (Mantovani et al. 1998), is activated by inflammatory cytokines, binds IL-1 and plays an anti-inflammatory role. In addition to preferential expression of these neutrophil and inflammation-related transcripts, the plasma samples from patients in group C demonstrated strikingly elevated levels of TNFα. TNFα is known to induce expression of TNFAIP6 and is itself a product of activated neutrophils. At the same time interferon are capable to activate expression of many of those genes. This highlights a relationship between neutrophils physiology and interferon signaling in SLE patients.

More significantly, the SLE patient groups defined by gene expression analysis showed important differences in clinical and serological parameters. Patients who demonstrated both IFIG and neutrophil granule gene signatures (group C2) experienced higher rates of vascular involvement. Many of the patients in group C2 had a history of Raynaud's phenomenon and some had serious vascular manifestations. In addition, most group C2 patients had elevated levels of anti-SSA/Ro autoantibodies. Anti-SSA/Ro autoantibodies are common in patients with Sjogren's syndrome and are associated with Raynaud's phenomena (Garcia-Carrasco et al. 2002). Anti-SSA/Ro autoantibodies appear in 30-50% of SLE patients and have been associated with cutaneous vasculitis (Fukuda et al. 2009) and neutropenia (Kurien and Scofield 2006; Kurien et al. 2000). Anti-SSA/Ro autoantibodies cross-react with the 64 kDa autoantigen D1 protein on the neutrophil surface and may induce neutrophil activation, or alternatively cell death and neutropenia (Kurien et al. 2000). This data suggests that anti-SSA/Ro antibodies might promote NET formation, resulting in induction of the IFN-I pathway, along with damage to endothelial cells that results in vasculopathy (Hakkim et al. 2010; Villanueva et al. 2011).

Lupus patients whose gene expression data cluster with group B2 show bright IFIG and a signature that appears to be neutrophil-related but lacks high level expression of neutrophil granule genes. Clinically, group B2 patients had more mucocutaneous flares than patients in group A, and their plasma samples show increased levels of pro-inflammatory cytokines, particularly TNFα, IL-8, and IL-18. The molecular pattern described for group B2 patients suggests that mucocutaneous manifestations of SLE may be less dependent on contributions from low-density granulocytes and their products than are vascular manifestations.

This study provides new insights into the molecular mechanisms that account for the heterogeneity of clinical disease in lupus. By incorporating analysis of longitudinal biologic samples from SLE patients and HDs, along with consideration of points in time at which disease is either stable or flaring, five distinct patient groups with distinct clinical and serologic features have been identified. The high level neutrophil-granule signature and high prevalence of anti-SSA/Ro antibodies in group C2 suggest that induction of NETosis and its products might be relevant mechanisms in the vasculopathy seen in many patients with SLE. Additionally, this analysis provides novel insights into a distinct role for neutrophils and TNFα in the mucocutaneous disease experienced by some patients.

Additionally, as shown in Example 6, using K-mean clustering from the microarray data described in Example 1, functionally related clusters including previously described IFIG, and neutrophil granule, along with plasma cell genes, and plasma factors von Willebrand factor and IL-10, were correlated to lupus disease activity. A four gene panel, with genes representative of IFIG, neutrophil granule, and plasma cell, along with T cells/iNKT genes, were also indicative of current flare activity as well as future flare activity (Example 7).

Signature Genes

This data show for the first time biomarkers, in the form of signature genes, which correlate to the severity of SLE and its clinical manifestation. The expression of these genes can be specifically used to screen for, identify and/or predict the clinical manifestation and disease severity of subjects who have been diagnosed with SLE. These biomarkers include:

type I interferon inducible genes (IFIG);
neutrophil granule genes; and
neutrophil-related genes, associated with increased expression by neutrophils in peripheral blood.

Genes in the type I interferon inducible gene signature include those in Table 2.

Genes in the neutrophil granule gene signature include those in Table 3.

Genes in the neutrophil-related gene signature include those in Table 4.

TABLE 2

Type I Interferon Inducible (IFIG) genes

| Gene Symbol | Gene Title |
| --- | --- |
| ANKRD22 | ankyrin repeat domain 22 |
| BST2 | bone marrow stromal cell antigen 2 |
| CCR1 | chemokine (C—C motif) receptor 1 |
| CMPK2 | cytidine monophosphate (UMP-CMP) kinase 2, mitochondrial |
| CXCL11 | chemokine (C—X—C motif) ligand 11 |
| DDX58 | DEAD (Asp-Glu-Ala-Asp) box polypeptide 58 |
| DDX60 | DEAD (Asp-Glu-Ala-Asp) box polypeptide 60 |
| DDX60L | DEAD (Asp-Glu-Ala-Asp) box polypeptide 60-like |
| DTX3L | deltex 3-like (*Drosophila*) |
| EIF2AK2 | eukaryotic translation initiation factor 2-alpha kinase 2 |
| EPSTI1 | epithelial stromal interaction 1 (breast) |
| ETV7 | ets variant 7 |
| FBXO6 | F-box protein 6 |
| FLJ42418 | FLJ42418 protein |
| GBP1 | guanylate binding protein 1, interferon-inducible, 67 kDa |
| GPR84 | G protein-coupled receptor 84 |
| H1F0 | H1 histone family, member 0 |
| HERC5 | hect domain and RLD 5 |
| HERC6 | hect domain and RLD 6 |
| IFI27 | interferon, alpha-inducible protein 27 |
| IFI35 | interferon-induced protein 35 |
| IFI44 | Interferon-induced protein 44 |
| IFIH1 | Interferon induced with helicase C domain 1 |
| IFIT1 | interferon-induced protein with tetratricopeptide repeats 1 |
| IFIT2 | interferon-induced protein with tetratricopeptide repeats 2 |
| IFIT3 | interferon-induced protein with tetratricopeptide repeats 3 |
| IFIT5 | interferon-induced protein with tetratricopeptide repeats 5 |
| IFITM1 | interferon induced transmembrane protein 1 (9-27) |
| IFITM3 | interferon induced transmembrane protein 3 (1-8U) |
| IL1RN | interleukin 1 receptor antagonist |
| IRF7 | interferon regulatory factor 7 |
| ISG15 | ISG15 ubiquitin-like modifier |
| JUP | junction plakoglobin |

TABLE 2-continued

Type I Interferon Inducible (IFIG) genes

| Gene Symbol | Gene Title |
|---|---|
| KLHDC7B | kelch domain containing 7B |
| KMO | kynurenine 3-monooxygenase (kynurenine 3-hydroxylase) |
| LAMP3 | lysosomal-associated membrane protein 3 |
| LAP3 | leucine aminopeptidase 3 |
| LGALS3BP /// | lectin, galactoside-binding, soluble, 3 binding protein /// similar to |
| LOC100133842 | lectin, galactoside-binding, soluble, 3 binding protein |
| LIPA | lipase A, lysosomal acid, cholesterol esterase |
| LOC100128718 | Hypothetical protein LOC100128718 |
| LOC147645 | hypothetical protein LOC147645 |
| LOC203274 | Hypothetical protein LOC203274 |
| LOC26010 | viral DNA polymerase-transactivated protein 6 |
| LY6E | lymphocyte antigen 6 complex, locus E |
| MS4A4A | membrane-spanning 4-domains, subfamily A, member 4 |
| MT2A | metallothionein 2A |
| MX1 | myxovirus (influenza virus) resistance 1, interferon-inducible protein p78 (mouse) |
| MX2 | myxovirus (influenza virus) resistance 2 (mouse) |
| NEXN | nexilin (F actin binding protein) |
| OAS1 | 2',5'-oligoadenylate synthetase 1, 40/46 kDa |
| OAS2 | 2'-5'-oligoadenylate synthetase 2, 69/71 kDa |
| OAS3 | 2'-5'-oligoadenylate synthetase 3, 100 kDa |
| OASL | 2'-5'-oligoadenylate synthetase-like |
| ODF3B | outer dense fiber of sperm tails 3B |
| PARP12 | poly (ADP-ribose) polymerase family, member 12 |
| PARP9 | poly (ADP-ribose) polymerase family, member 9 |
| PLSCR1 | phospholipid scramblase 1 |
| RGL1 | ral guanine nucleotide dissociation stimulator-like 1 |
| RSAD2 | radical S-adenosyl methionine domain containing 2 |
| RTP4 | receptor (chemosensory) transporter protein 4 |
| SAMD4A | sterile alpha motif domain containing 4A |
| SAMD9 | sterile alpha motif domain containing 9 |
| SAMD9L | sterile alpha motif domain containing 9-like |
| SCO2 | SCO cytochrome oxidase deficient homolog 2 (yeast) |
| SIGLEC1 | sialic acid binding Ig-like lectin 1, sialoadhesin |
| SP100 | SP100 nuclear antigen |
| SP110 | SP110 nuclear body protein |
| SPTLC2 | Serine palmitoyltransferase, long chain base subunit 2 |
| STAT1 | signal transducer and activator of transcription 1, 91 kDa |
| STAT2 | signal transducer and activator of transcription 2, 113 kDa |
| TAP1 | transporter 1, ATP-binding cassette, sub-family B (MDR/TAP) |
| TLR7 | toll-like receptor 7 |
| TNFSF10 | tumor necrosis factor (ligand) superfamily, member 10 |
| TNFSF13B | tumor necrosis factor (ligand) superfamily, member 13b |
| TRIM22 | tripartite motif-containing 22 |
| TRIM5 | tripartite motif-containing 5 |
| TRIP6 | thyroid hormone receptor interactor 6 |
| TYMP | thymidine phosphorylase |
| UBE2L6 | ubiquitin-conjugating enzyme E2L 6 |
| USP18 | ubiquitin specific peptidase 18 |
| XAF1 | XIAP associated factor 1 |
| ZBP1 | Z-DNA binding protein 1 |
| ZCCHC2 | zinc finger, CCHC domain containing 2 |

TABLE 3

Neutrophil Granule Genes

| Gene Symbol | Gene Title |
|---|---|
| ANXA3 | annexin A3 |
| ARG1 | arginase, liver |
| BPI | bactericidal/permeability-increasing protein |
| CAMP | cathelicidin antimicrobial peptide |
| CD24 | CD24 molecule |
| CEACAM1 | carcinoembryonic antigen-related cell adhesion molecule 1 (biliary glycoprotein) |
| CEACAM6 | carcinoembryonic antigen-related cell adhesion molecule 6 (non-specific cross reacting antigen) |
| CEACAM8 | carcinoembryonic antigen-related cell adhesion molecule 8 |
| CHI3L1 | chitinase 3-like 1 (cartilage glycoprotein-39) |
| CRISP3 | cysteine-rich secretory protein 3 |
| DEFA1 | defensin, alpha 1 |
| DEFA4 | defensin, alpha 4, corticostatin |
| ERG | v-ets erythroblastosis virus E26 oncogene homolog (avian) |
| HP /// HPR | haptoglobin /// haptoglobin-related protein |
| LCN2 | lipocalin 2 |
| LTF | lactotransferrin |
| MMP8 | matrix metallopeptidase 8 (neutrophil collagenase) |
| MMP9 | matrix metallopeptidase 9 (gelatinase B, 92 kDa gelatinase, 92 kDa type IV collagenase) |
| MPO | myeloperoxidase |
| OLFM4 | olfactomedin 4 |
| OLR1 | oxidized low density lipoprotein (lectin-like) receptor 1 |
| RNASE3 | ribonuclease, RNase A family, 3 (eosinophil cationic protein) |

TABLE 3-continued

Neutrophil Granule Genes

| Gene Symbol | Gene Title |
| --- | --- |
| SLC2A5 | solute carrier family 2 (facilitated glucose/fructose transporter), member 5 |
| TCN1 | transcobalamin I (vitamin B12 binding protein, R binder family) |

TABLE 4

Neutrophil-Related Genes

| Gene Symbol | Gene Title |
| --- | --- |
| ABCA1 | ATP-binding cassette, sub-family A (ABC1), member 1 |
| ADM | adrenomedullin |
| AQP9 | aquaporin 9 |
| CYP4F3 | cytochrome P450, family 4, subfamily F, polypeptide 3 |
| DDX60L | DEAD (Asp-Glu-Ala-Asp) box polypeptide 60-like |
| DHRS9 | dehydrogenase/reductase (SDR family) member 9 |
| DOCK4 | Dedicator of cytokinesis 4 |
| FFAR2 | free fatty acid receptor 2 |
| FPR1 | formyl peptide receptor 1 |
| FPR2 | formyl peptide receptor 2 |
| HECW2 | HECT, C2 and WW domain containing E3 ubiquitin protein ligase 2 |
| IL1R2 | interleukin 1 receptor, type II |
| KCNJ15 | potassium inwardly-rectifying channel, subfamily J, member 15 |
| LIMK2 | LIM domain kinase 2 |
| LRG1 | leucine-rich alpha-2-glycoprotein 1 |
| Ly96 | Lymphocyte antigen 96 |
| MANSC1 | MANSC domain containing 1 |
| PRRG4 | Proline rich GLA 4 |
| SLC22A4 | solute carrier family 22 (organic cation/ergothioneine transporter), member 4 |
| TNFAIP6 | tumor necrosis factor, alpha-induced protein 6 |
| TNFRSF10C | tumor necrosis factor receptor superfamily, member 10c, decoy without an intracellular domain |
| TRPM6 | transient receptor potential cation channel, subfamily M, member 6 |
| VNN3 | vanin 3 |

By using these biomarkers, alone or preferably in conjunction, important predictions and determinations can be made regarding the course of an SLE patient's progression. While tests for these biomarkers can be performed at any time after a diagnosis of SLE, preferably such tests would be performed as soon as possible after a positive diagnosis of SLE is made by a clinician. In that manner, the valuable insight into the clinical manifestations of the disease can be utilized in both choice of therapy as well as the determination for the amount and timing needed for monitoring by a health care provider, often time prior to any noticeable symptoms occur.

In the one embodiment of the present invention, a test for type I interferon inducible genes (IFIG) could be done and a positive result could indicate at least that the subject is at an increased risk for flares. This would indicate to a clinician or health care provider at least increased monitoring was needed for this subject, and perhaps more aggressive therapy.

In another embodiment, a test for neutrophil granule genes could be done and a positive result could indicate at least that the subject is at an increased risk for flares, including severe flares, and increased vascular manifestation. This would indicate to a clinician or health care provider increased monitoring was needed for this subject, and perhaps more aggressive therapy focused on vascular indications.

In another embodiment, a test for neutrophil-related genes could be done and a positive result could indicate at least that the subject is at an increased risk for flares, including severe flare, and increased mucocutaneous manifestation. This would indicate to a clinician or health care provider increased monitoring was needed for this subject, and perhaps more aggressive therapy focused on mucocutaneous indications.

Tests for any combination of the three clusters of genes can also be performed. For example, in a further embodiment, the subject would be tested for both IFIG and neutrophil granule signature genes. A positive result of both signatures would indicate an increased risk for flares, including severe flares, as well as increased vascular involvement. Subjects who have both these signatures also have the most renal involvements and have the most active diseases. SLE subjects who tested positive for both these signatures would greatly benefit from early therapeutic intervention, as well as increased monitoring. Moreover, the therapeutic intervention would be more focused on vascular and renal etiologies. Additionally, a subject who tested positive for the neutrophil granule genes and negative for IFIG would also be at an increased risk of flares, including severe flares, as well as increased vascular involvement, although the disease is not as active in these patients who test positive for only the neutrophil-granule-related genes.

In yet a further embodiment, a subject would be tested for IFIG and neutrophil-related signature genes. A positive result of both of these signatures would indicate an increased risk of flares and mucocutaneous involvement, with an active disease. This would indicate to a clinician that increased monitoring and therapy focused on mucocutaneous manifestations of SLE should be started early in the disease. A negative result on the neutrophil-related signature genes but positive on the IFIG may indicate a less active disease.

A positive result for a particular gene signature would be considered an increase in gene expression of at least one gene in the signature as compared to the expression of the same gene in a healthy donor, preferably an increase in gene expression of at least two genes in the signature as compared to the expression of the same gene in a healthy donor, preferably an increase in gene expression of at least five genes in the signature as compared to the expression of the same gene in a healthy donor, preferably an increase in gene expression in at least ten genes in the signature as compared to the expression of the same gene in a healthy donor, and most preferably an increase in gene expression in at least twenty genes in the signature as compared to the expression of the same gene in a healthy donor.

A negative result for a particular gene signature would be considered either a decrease in or the same gene expression of at least one gene in the signature as compared to the expression of the same gene in a healthy donor, preferably either a decrease in or the same gene expression of at least two genes in the signature as compared to the expression of the same gene in a healthy donor, preferably either a decrease in or the same gene expression of at least five genes in the signature as compared to the expression of the same gene in a healthy donor, preferably either a decrease in or the same gene expression of at least ten genes in the signature as compared to the expression of the same gene in a healthy donor, and most preferably either a decrease in or the same gene expression of at least twenty genes in the signature as compared to the expression of the same gene in a healthy donor.

A preferred embodiment is testing a subject for all three gene signatures as soon as possible after a positive diagnosis of SLE so that predictions can be made regarding the activity and severity of the disease as well as the areas that therapies should be focused. Any single gene or any combination of genes from each signature can be used in the method and assays of the invention. A summary of the clinical indications of a positive result for each gene signature is found in Table 1.

Any one of the preferred or additional IFIG genes or any combination of more than one up to all 83 differentially expressed signature IFIG genes can be used in the methods and assays of the present invention. Preferred IFIG signature genes to be use in the method of the invention are IF127, IFIT1 and IFIT3.

Any one neutrophil granule signature gene or any combination of more than one up to all 24 differentially expressed signature neutrophil granule genes can be used in the methods and assays of the present invention. Preferred neutrophil granule signature genes for use in the methods and assays of the invention are OLFM4, CRISP3, IF127, DEFA4, MMP8, ANXA3, ARG1, MPO, DEFA1, LTF, and CEACAM6, with the two most preferred neutrophil granule signature genes being CEACAM6 and LTF.

Likewise, any one neutrophil-related signature gene or any combination of more than one up to all 23 differentially expressed signature neutrophil related genes can be used in the methods and assays of the present invention. Preferred neutrophil-related signature genes for use in the methods and assays of the invention are TNFAIP6, FPR1, FPR2, LY96, CYP4F3, IL1R2, PRRG4, and DOCK4, with TNFAIP6, CYP4F3 and FPR1 being more preferred and TNFAIP6 being most preferred.

A preferred embodiment is found in Example 4 where seven genes were chosen from the three gene signatures, and with those seven genes, the five groups with varying clinical manifestations and disease activity were classified. These genes were IFIT1 and IFIT3 which represented the IFIG signature, CEACAM6 and LTF which represented the neutrophil granules gene signature and TNFAIP6, CYP4F3 and FPR1 which represented the neutrophil-related gene signature.

Additional gene biomarkers have also been identified that correlate to disease activity, i.e., flare, and predict and identify those SLE subjects who are at risk for more frequent flares while they are not flaring.

These biomarkers include:
type I interferon inducible genes (IFIG) found in Table 2;
neutrophil granule genes found in Table 3;
Immunoglobulin/plasma cell genes found in Table 5; and
T-cells/iNKT genes found in Table 6.

TABLE 5

Immunoglobulin/plasma cell genes

| Gene Symbol | Gene Title |
| --- | --- |
| BHLHE41 | basic helix-loop-helix family, member e41 |
| CAV1 | caveolin 1, caveolae protein, 22 kDa |
| CD38 | CD38 molecule |
| DTNB | dystrobrevin, beta |
| ELL2 | elongation factor, RNA polymerase II, 2 |
| FAM20B | Family with sequence similarity 20, member B |
| FAM46C | family with sequence similarity 46, member C |
| GLDC | glycine dehydrogenase (decarboxylating) |
| IGF1 | insulin-like growth factor 1 (somatomedin C) |
| IGH@ /// IGHA1 /// IGHA2 /// IGHD /// IGHG1 /// IGHG3 /// IGHG4 /// IGHM /// IGHV4-31 /// LOC100126583 /// LOC642131 /// LOC652128 /// VSIG6 | immunoglobulin heavy locus /// immunoglobulin heavy constant alpha 1 /// immunoglobulin heavy constant alpha 2 (A2m marker) /// immunoglobulin heavy constant delta /// immunoglobulin heavy constant gamma 1 (G1m marker) /// immunoglobulin heavy constant gamma 3 (G3m marker) /// immunoglobulin heavy constant gamma 4 (G4m marker) /// immunoglobulin heavy constant mu /// immunoglobulin heavy variable 4-31 /// hypothetical LOC100126583 /// similar to hCG1812074 /// similar to Ig heavy chain V-II region ARH-77 precursor /// V-set and immunoglobulin domain containing 6 |
| IGH@ /// IGHA1 /// IGHA2 /// IGHG1 /// IGHG2 /// IGHG3 /// IGHM /// IGHV4-31 /// LOC100126583 /// LOC652494 | immunoglobulin heavy locus /// immunoglobulin heavy constant alpha 1 /// immunoglobulin heavy constant alpha 2 (A2m marker) /// immunoglobulin heavy constant gamma 1 (G1m marker) /// immunoglobulin heavy constant gamma 2 (G2m marker) /// immunoglobulin heavy constant gamma 3 (G3m marker) /// immunoglobulin heavy constant mu /// immunoglobulin heavy variable 4-31 /// hypothetical LOC100126583 /// similar to Ig heavy chain V-III region VH26 precursor |
| IGH@ /// IGHA1 /// IGHA2 /// LOC100126583 | immunoglobulin heavy locus /// immunoglobulin heavy constant alpha 1 /// immunoglobulin heavy constant alpha 2 (A2m marker) /// hypothetical LOC100126583 |
| IGH@ /// IGHA1 /// IGHG1 /// IGHG3 /// IGHM /// IGHV3-23 /// IGHV4-31 | immunoglobulin heavy locus /// immunoglobulin heavy constant alpha 1 /// immunoglobulin heavy constant gamma 1 (G1m marker) /// immunoglobulin heavy constant gamma 3 (G3m marker) /// immunoglobulin heavy constant mu /// immunoglobulin heavy variable 3-23 /// immunoglobulin heavy variable 4-31 |
| IGH@ /// IGHG1 /// IGHG2 /// IGHM /// IGHV4-31 | immunoglobulin heavy locus /// immunoglobulin heavy constant gamma 1 (G1m marker) /// immunoglobulin heavy constant gamma 2 (G2m marker) /// immunoglobulin heavy constant mu /// immunoglobulin heavy variable 4-31 |
| IGHA1 /// IGHD /// IGHG1 /// IGHG3 /// | immunoglobulin heavy constant alpha 1 /// immunoglobulin heavy constant delta /// immunoglobulin heavy constant gamma |

TABLE 5-continued

Immunoglobulin/plasma cell genes

| Gene Symbol | Gene Title |
|---|---|
| IGHM /// IGHV3-23 /// IGHV4-31 /// LOC100126583 | 1 (G1m marker) /// immunoglobulin heavy constant gamma 3 (G3m marker) /// immunoglobulin heavy constant mu /// immunoglobulin heavy variable 3-23 /// immunoglobulin heavy variable 4-31 /// hypothetical LOC100126583 |
| IGHA1 /// IGHD /// IGHG1 /// IGHM /// IGHV3-23 /// IGHV4-31 | immunoglobulin heavy constant alpha 1 /// immunoglobulin heavy constant delta /// immunoglobulin heavy constant gamma 1 (G1m marker) /// immunoglobulin heavy constant mu /// immunoglobulin heavy variable 3-23 /// immunoglobulin heavy variable 4-31 |
| IGHD | immunoglobulin heavy constant delta |
| IGHG1 | Immunoglobulin heavy constant gamma 1 (G1m marker) |
| IGHM | immunoglobulin heavy constant mu |
| IGJ | immunoglobulin J polypeptide, linker protein for immunoglobulin alpha and mu polypeptides |
| IGK@ /// IGKC | immunoglobulin kappa locus /// immunoglobulin kappa constant |
| IGK@ /// IGKC /// IGKV3-20 /// IGKV3D-11 /// IGKV3D-15 /// LOC440871 | immunoglobulin kappa locus /// immunoglobulin kappa constant /// immunoglobulin kappa variable 3-20 /// immunoglobulin kappa variable 3D-11 /// immunoglobulin kappa variable 3D-15 (gene/pseudogene) /// similar to hCG2043206 |
| IGK@ /// IGKC /// LOC647506 /// LOC650405 /// LOC652493 | immunoglobulin kappa locus /// immunoglobulin kappa constant /// similar to Ig kappa chain V-I region HK101 precursor /// similar to Ig kappa chain V-I region HK102 precursor /// similar to Ig kappa chain V-I region HK102 precursor |
| IGKC | Immunoglobulin kappa constant |
| IGKC | immunoglobulin kappa constant |
| IGKC /// IGKV1-5 /// LOC100130100 /// LOC647506 /// LOC650405 /// LOC652493 /// LOC652694 | immunoglobulin kappa constant /// immunoglobulin kappa variable 1-5 /// similar to hCG26659 /// similar to Ig kappa chain V-I region HK101 precursor /// similar to Ig kappa chain V-I region HK102 precursor /// similar to Ig kappa chain V-I region HK102 precursor /// similar to Ig kappa chain V-I region HK102 precursor |
| IGKC /// IGKV1-5 /// LOC647506 /// LOC652694 | immunoglobulin kappa constant /// immunoglobulin kappa variable 1-5 /// similar to Ig kappa chain V-I region HK101 precursor /// similar to Ig kappa chain V-I region HK102 precursor |
| IGKV1OR15-118 | immunoglobulin kappa variable 1/OR15-118 pseudogene |
| IGKV4-1 | immunoglobulin kappa variable 4-1 |
| IGL@ | Immunoglobulin lambda locus |
| IGL@ /// IGLC1 /// IGLV2-11 /// IGLV2-18 /// IGLV2-23 | immunoglobulin lambda locus /// immunoglobulin lambda constant 1 (Mcg marker) /// immunoglobulin lambda variable 2-11 /// immunoglobulin lambda variable 2-18 /// immunoglobulin lambda variable 2-23 |
| IGL@ /// IGLV1-36 /// IGLV1-44 | immunoglobulin lambda locus /// immunoglobulin lambda variable 1-36 /// immunoglobulin lambda variable 1-44 |
| IGL@ /// LOC96610 | immunoglobulin lambda locus /// BMS1 homolog, ribosome assembly protein (yeast) pseudogene |
| IGLJ3 | immunoglobulin lambda joining 3 |
| IGLL3 | immunoglobulin lambda-like polypeptide 3 |
| IGLV2-11 /// IGLV2-18 /// IGLV2-23 | immunoglobulin lambda variable 2-18 /// immunoglobulin lambda variable 2-23 |
| IGLV3-19 | immunoglobulin lambda variable 3-19 |
| LOC100130100 | similar to hCG26659 |
| LOC652493 | similar to Ig kappa chain V-I region HK102 precursor |
| LOC91316 | glucuronidase, beta/immunoglobulin lambda-like polypeptide 1 pseudogene |
| MGC29506 | hypothetical protein MGC29506 |
| RGS13 | regulator of G-protein signaling 13 |
| SSPN | sarcospan (Kras oncogene-associated gene) |
| TNFRSF17 | tumor necrosis factor receptor superfamily, member 17 |
| TXNDC5 | thioredoxin domain containing 5 (endoplasmic reticulum) |

TABLE 6

T-cells/iNKT genes

| Gene Symbol | Gene Title |
|---|---|
| BEX5 | brain expressed, X-linked 5 |
| CCR3 | chemokine (C—C motif) receptor 3 |
| CD1C | CD1c molecule |
| CLIC5 | chloride intracellular channel 5 |
| EPHA4 | EPH receptor A4 |
| GATA2 | GATA binding protein 2 |
| IL4 | interleukin 4 |
| IL5RA | interleukin 5 receptor, alpha |
| ISM1 | isthmin 1 homolog (zebrafish) |
| KLRB1 | killer cell lectin-like receptor subfamily B, member 1 |

TABLE 6-continued

T-cells/iNKT genes

| Gene Symbol | Gene Title |
|---|---|
| MAF | v-maf musculoaponeurotic fibrosarcoma oncogene homolog (avian) |
| NAP1L2 | nucleosome assembly protein 1-like 2 |
| NAP1L3 | nucleosome assembly protein 1-like 3 |
| RORC | RAR-related orphan receptor C |
| ST6GALNAC1 | ST6 (alpha-N-acetyl-neuraminyl-2,3-beta-galactosyl-1,3)-N-acetylgalactosaminide alpha-2,6-sialyltransferase 1 |
| ST8SIA1 | ST8 alpha-N-acetyl-neuraminide alpha-2,8-sialyltransferase 1 |
| TMEM176B | transmembrane protein 176B |
| TNFRSF10D | tumor necrosis factor receptor superfamily, member 10d, decoy with truncated death domain |
| TRPC1 | transient receptor potential cation channel, subfamily C, member 1 |
| USP53 | ubiquitin specific peptidase 53 |

By using these biomarkers, in conjunction, important predictions and determinations can be made regarding the course of an SLE patient's progression. While tests for these biomarkers can be performed at any time after a diagnosis of SLE, preferably such tests would be performed as soon as possible after a positive diagnosis of SLE is made by a clinician. In that manner, the valuable insight into the clinical manifestations of the disease can be utilized in both choice of therapy as well as the determination for the amount and timing needed for monitoring by a health care provider, often time prior to any noticeable symptoms occur.

In the one embodiment of the present invention, a test for one or more genes from these four signatures would be done and a positive result would indicate that a subject is at an increased risk for flares. This would indicate to a clinician increased monitoring of the patient as well as more aggressive earlier therapy. A positive result is an increase in the IFIG gene, an increase in the neutrophil granule gene, an increase in the immunoglobulin/plasma cell gene but a decrease in the T-cells/iNKT genes. Preferred genes to be used in the panel are: IFIT3, MMP8, CD38, and KLRB1.

All of these genes in all five signatures found in Tables 2, 3, 4, 5, and 6, can also be used as targets for developing therapies and research tools.

Assays and Methods to Detect and Measure Signature Genes

In order to detect any of these transcripts or genes, a sample of biological tissue or fluid from a subject who has been positively diagnosed with SLE is obtained and prepared and analyzed for the presence of the IFIG, neutrophil granule, neutrophil-related, immunoglobulin/plasma cell, and/or T-cells/iKNT signature genes, This can be achieved in numerous ways, by a diagnostic laboratory, and/or a health care provider.

Most methods start with obtaining a sample of biological tissue or fluid from the subject with SLE and extracting, isolating and/or purifying the nucleic acid (e.g., genomic DNA, cDNA, RNA) from the tissue or fluid.

The nucleic acid can be obtained from any biological tissue. Preferred biological tissues include, but are not limited to, epidermal, whole blood, and plasma.

The nucleic acid can be obtained from any biological fluid. Preferred fluids include, but are not limited to, plasma, saliva, and urine.

In a preferred method, the nucleic acid is obtained from peripheral blood mononuclear cells.

The nucleic acid is extracted, isolated and purified from the cells of the tissue or fluid by methods known in the art.

If required, a nucleic acid sample having the signature gene sequence(s) are prepared using known techniques. For example, the sample can be treated to lyse the cells, using known lysis buffers, sonication, electroporation, with purification and amplification occurring as needed, as will be understood by those in the skilled in the art. In addition, the reactions can be accomplished in a variety of ways. Components of the reaction may be added simultaneously, or sequentially, in any order. In addition, the reaction can include a variety of other reagents which can be useful in the methods and assays and would include but is not limited to salts, buffers, neutral proteins, such albumin, and detergents, which may be used to facilitate optimal hybridization and detection, and/or reduce non-specific or background interactions. Also reagents that otherwise improve the efficiency of the assay, such as protease inhibitors, nuclease inhibitors, and anti-microbial agents, can be used, depending on the sample preparation methods and purity.

Once prepared, mRNA or other nucleic acids are analyzed by methods known to those of skill in the art. The nucleic acid sequence corresponding to a signature gene can be any length, with the understanding that longer sequences are more specific. Preferably a nucleic acid corresponding to a signature gene is at least 20 nucleotides in length. Preferred ranges are from 20 to 100 nucleotides in length, with from 30 to 60 nucleotides being more preferred, and from 40 to 50 being most preferred.

In addition, when nucleic acids are to be detected preferred methods utilize cutting or shearing techniques to cut the nucleic acid sample containing the target sequence into a size that will facilitate handling and hybridization to the target. This can be accomplished by shearing the nucleic acid through mechanical forces, such as sonication, or by cleaving the nucleic acid using restriction endonucleases, or any other methods known in the art. However, in most cases, the natural degradation that occurs during archiving results in "short" oligonucleotides. In general, the methods and assays of the invention can be done on oligonucleotides as short as 20-100 base pairs, with from 20 to 50 being preferred, and between 40 and 50, including 44, 45, 46, 47, 48 and 49 being the most preferred.

A preferred method of the invention is performing gene expression profiling of the sample. Gene expression profiling refers to examining expression of one or more RNAs in a cell, preferably mRNA. Often at least or up to 10, 100, 100, 10,000 or more different mRNAs are examined in a single experiment.

In a preferred method and assay of the invention, the gene expression of the mRNA or other nucleic acid obtained from the subject with SLE is compared to the gene expression of a healthy donor. Typically expression is compared to expression of a consistently expressed housekeeping gene transcript, the relative expression determined, and then the expression of the subject is compared to the expression of the healthy control. The reference fold changes of each gene listed in Tables 2-6 as compared to healthy controls is listed in Table 9.

In a preferred method to determine which group a subject with SLE would be classified as, the expression of 1 to 83 of IFIG signature genes is determined. In another preferred method, 1 to 24 of the neutrophil granule genes is determined, and in another preferred method, 1 to 23 of the neutrophil-related genes is determined. In a preferred embodiment, the expression of at least gene from each signature is determined, and in a most preferred embodiment, the expression of the genes, IFIT1, IFIT3, CEACAM6, LTF, TNFAIP6, CYP4F3 and FPR1 are determined.

In a method to determine future flares in a subject with SLE, the expression of 1 to 83 of IFIG signature genes is determined, 1 to 24 of the neutrophil granule genes is determined, 1 to 45 of the immunoglobulin/plasma cell genes is determined, and 1 to 20 of the T-cell/iKNT genes is determined. In a preferred embodiment, the expression of IFIT3, KLRB1, CD38, and MMP8 are determined.

Methods for examining gene expression, are often hybridization based, and include, Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

Alternatively, the level of protein product of the genes can be measured from a protein sample from the biological tissue or fluid using methods described below.

For a general description of these techniques, see also Sambrook et al. 1989; Kriegler 1990; and Ausebel et al. 1990.

The preferred method for the detection of the transcripts is the use of arrays or microarrays. These terms are used interchangeably and refer to any ordered arrangement on a surface or substrate of different molecules, referred to herein as "probes." Each different probe of any array is capable of specifically recognizing and/or binding to a particular molecule, which is referred to herein as its "target" in the context of arrays. Examples of typical target molecules that can be detected using microarrays include mRNA transcripts, cRNA molecules, cDNA, PCR products, and proteins.

Microarrays are useful for simultaneously detecting the presence, absence and quantity of a plurality of different target molecules in a sample. The presence and quantity, or absence, of the probe's target molecule in a sample may be readily determined by analyzing whether and how much of a target has bound to a probe at a particular location on the surface or substrate.

In a preferred embodiment, arrays used in the present invention are "addressable arrays" where each different probe is associated with a particular "address."

The arrays used in the present invention are preferable nucleic acid arrays that comprise a plurality of nucleic acid probes immobilized on a surface or substrate. The different nucleic acid probes are complementary to, and therefore can hybridize to, different target nucleic acid molecules in a sample. Thus, each probe can be used to simultaneously detect the presence and quantity of a plurality of different genes, e.g., the presence and abundance of different mRNA molecules, or of nucleic acid molecules derived therefrom (for example, cDNA or cRNA).

The arrays are preferably reproducible, allowing multiple copies of a given array to be produced and the results from each easily compared to one another. Preferably microarrays are small, and made from materials that are stable under binding conditions. A given binding site or unique set of binding sites in the microarray will specifically bind to the target. It will be appreciated that when cDNA complementary to the RNA of a cell is made and hybridized to a microarray under suitable conditions, the level or degree of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding a nucleic acid product of the gene) that is not transcribed in the cell will have little or no signal, while a gene for which mRNA is highly prevalent will have a relatively strong signal.

By way of example, GeneChip® (Affymetrix, Santa Clara, Calif.), generates data for the assessment of gene expression profiles and other biological assays. Oligonucleotide expression arrays simultaneously and quantitatively "interrogate" thousands of mRNA transcripts. Each transcript can be represented on a probe array by multiple probe pairs to differentiate among closely related members of gene families. Each probe contains millions of copies of a specific oligonucleotide probe, permitting the accurate and sensitive detection of even low-intensity mRNA hybridization patterns. After hybridization data is captured, using a scanner or optical detection systems, software can be used to automatically calculate the intensity values for each probe cell. Probe cell intensities can be used to calculate an average intensity for each gene, which correlates with mRNA abundance levels. Expression data can be quickly sorted based on any analysis parameter and displayed in a variety of graphical formats for any selected subset of genes.

Further examples of microarrays that can be used in the assays and methods of the invention are microarrays synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591.

Other exemplary arrays that are useful for use in the invention include, but are not limited to, Sentrix® Array or Sentrix® BeadChip Array available from Illumina®, Inc. (San Diego, Calif.) or others including beads in wells such as those described in U.S. Pat. Nos. 6,266,459; 6,355,431; 6,770,441; and 6,859,570. Arrays that have particle on the surface can also be used and include those described in U.S. Pat. Nos. 6,489,606; 7,106,513; 7,126,755; and 7,164,533.

An array of beads in a fluid format, such as a fluid stream of a flow cytometer or similar device, can also be used in methods for the invention. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

A spotted microarray can also be used in a method of the invention. An exemplary spotted microarray is a CodeLink™ Array available from Amersham Biosciences.

Another microarray that is useful in the invention is one that is manufactured using inkjet printing methods such as SurePrint™ Technology available from Agilent Technologies. Other microarrays that can be used in the invention include, without limitation, those described in U.S. Pat. Nos.

5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751.

DASL can be used for quantitative measurements of RNA target sequences as well as for DNA target sequences. DASL is described, for example, in Fan et al. 2004.

Additional techniques for rapid gene sequencing and analysis of gene expression include, SAGE (serial analysis of gene expression). For SAGE, a short sequence tag (typically about 10-14 bp) contains sufficient information to uniquely identify a transcript. These sequence tags can be linked together to form long serial molecules that can be cloned and sequenced. Quantitation of the number of times a particular tag is observed proves the expression level of the corresponding transcript (see, e.g., Velculescu et al. 1995; Velculescu et al. 1997; and de Waard et al. 1999).

Screening and diagnostic method of the current invention may involve the amplification of the target loci. A preferred method for target amplification of nucleic acid sequences is using polymerases, in particular polymerase chain reaction (PCR). PCR or other polymerase-driven amplification methods obtain millions of copies of the relevant nucleic acid sequences which then can be used as substrates for probes or sequenced or used in other assays.

Amplification using polymerase chain reaction is particularly useful in the embodiments of the current invention. PCR is a rapid and versatile in vitro method for amplifying defined target DNA sequences present within a source of DNA. Usually, the method is designed to permit selective amplification of a specific target DNA sequence(s) within a heterogeneous collection of DNA sequences (e.g. total genomic DNA or a complex cDNA population). To permit such selective amplification, some prior DNA sequence information from the target sequences is required. This information is used to design two oligonucleotide primers (amplimers) which are specific for the target sequence and which are often about 15-25 nucleotides long.

Mutation detection using the 5'→3' exonuclease activity of Taq DNA polymerase (TaqMan™ assay) can also be used as a screening and diagnostic method of the current invention. Such an assay involves hybridization of three primers, the third primer being intended to bind just downstream of one of the conventional primers which should be allele-specific. The additional primer carries a blocking group at the 3' terminal nucleotide so that it cannot prime new DNA synthesis and at its 5' end carries a labeled group. In modern versions of the assay, the label is a fluorogenic group and the third primer also carries a quencher group. If the upstream primer which is bound to the same strand is able to prime successfully, Taq DNA polymerase will extend a new DNA strand until it encounters the third primer in which case its 5'→3' exonuclease will degrade the primer causing release of separate nucleotides containing the dye and the quencher, and an observable increase in fluorescence.

PCR with melting curve analysis can also be used. PCR with melting curve analysis is an extension of PCR where the fluorescence is monitored over time as the temperature changes. Duplexes melt as the temperature increases and the hybridization of both PCR products and probes can be monitored. The temperature-dependent dissociation between two DNA-strands can be measured using a DNA-intercalating fluorophore such as SYBR green, EvaGreen or fluorophore-labelled DNA probes. In the case of SYBR green (which fluoresces 1000-fold more intensely while intercalated in the minor groove of two strands of DNA), the dissociation of the DNA during heating is measurable by the large reduction in fluorescence that results. Alternatively, juxtapositioned probes (one featuring a fluorophore and the other, a suitable quencher) can be used to determine the complementarity of the probe to the target sequence. This technique is sensitive enough to detect single-nucleotide polymorphisms (SNP) and can distinguish between various alleles by virtue of the dissociation patterns produced.

PCR with mass spectrometry uses mass spectrometry to detect the end product. Primer pairs are used and tagged with molecules of known masses, known as MassCodes. If DNA from any of the agent of primer panel is present, it will be amplified. Each amplified product will carry its specific Masscodes. The PCR product is then purified to remove unbound primers, dNTPs, enzyme and other impurities. Finally, the purified PCR products are subject of ultraviolet as the chemical bond with nucleic acid and primers are photolabile. As the Masscodes are liberated from PCR products they are detected with a mass spectrometer.

When a probe is to be used to detect the presence of IFIG, neutrophil granule, neutrophil-related, immunoglobulin/plasma cell and/or T-cell/iNKT nucleic acids, the biological sample that is to be analyzed must be treated to extract the nucleic acids. The nucleic acids to be targeted usually need to be at least partially single-stranded in order to form a hybrid with the probe sequence. If the nucleic acid is single stranded, no denaturation is required. However, if the nucleic acid to be probed is double stranded, denaturation must be performed by any method known in the art.

The nucleic acid to be analyzed and the probe are incubated under conditions which promote stable hybrid formation of the target sequence in the probe and the target sequence in the nucleic acid. The desired stringency of the hybridization will depend on factors such as the uniqueness of the probe in the part of the genome being targeted, and can be altered by washing procedure, temperature, probe length and other conditions known in the art, as set forth in Sambrook et al. 1989.

Labeled probes are, used to detect the hybrid, or alternatively, the probe is bound to a ligand which labeled either directly or indirectly. Suitable labels and methods for labeling are known in the art, and include biotin, fluorescence, chemiluminescence, enzymes, and radioactivity.

Assays using such probes include Southern blot analysis. In such an assay, a patient sample is obtained, the DNA processed, denatured, separated on an agarose gel, and transferred to a membrane for hybridization with a probe. Following procedures known in the art (e.g., Sambrook et al. 1989), the blots are hybridized with a labeled probe and a positive band indicates the presence of the target sequence. Southern blot hybridization can also be used to screen for the polymorphisms. In this method, the target DNA is digested with one or more restriction endonucleases, size-fractionated by agarose gel electrophoresis, denatured and transferred to a nitrocellulose or nylon membrane for hybridization. Following electrophoresis, the test DNA fragments are denatured in strong alkali. As agarose gels are fragile, and the DNA in them can diffuse within the gel, it is usual to transfer the denatured DNA fragments by blotting on to a durable nitrocellulose or nylon membrane, to which single-stranded DNA binds readily. The individual DNA fragments become immobilized on the membrane at positions which are a faithful record of the size separation achieved by agarose gel electrophoresis. Subsequently, the immobilized single-stranded target DNA sequences are allowed to associate with labeled single-stranded probe DNA. The probe will bind only to related DNA sequences in the target DNA, and their position on the membrane can be related back to the original gel in order to estimate their size.

Northern blots, done in the same fashion, but utilizing RNA, can also be used.

Dot-blot hybridization can also be used to screen for the IFIG, neutrophil granule, neutrophil-related, immunoglobulin/plasma cell and/or T-cell/iNKT nucleic acids. Nucleic acid including genomic DNA, cDNA and RNA is obtained from the subject with SLE, denatured and spotted onto a nitrocellulose or nylon membrane and lowed to dry. The membrane is exposed to a solution of labeled single stranded probe sequences and after allowing sufficient time for probe-target heteroduplexes to form, the probe solution is removed and the membrane washed, dried and exposed to an autoradiographic film. A positive spot is an indication of the target sequence in the DNA of the subject and a no spot an indication of the lack of the target sequence in the DNA of the subject.

Probes and Primers

The expression patterns for signature genes are determined based on quantitative detection of nucleic acids or oligonucleotides corresponding to the signature genes, which means at least two nucleotides covalently linked together. Thus, the invention also provides a collection of nucleic acids and oligonucleotides that correspond to a signature gene or a set of signature genes, i.e., IFIG signature, neutrophil granule signature, neutrophil-related signature, immunoglobulin/plasma cell signature and/or T-cell/iNKT signature. A nucleic acid useful in the methods and assays of the invention is defined above.

The nucleic acids corresponding to signature genes can be single stranded or double stranded, as specified, or contain portions of both double stranded or single stranded sequence. The nucleic acid can be DNA, both genomic and cDNA, RNA or a hybrid, where the nucleic acid contains any combination of deoxyribo- and ribo-nucleotides, and any combination of bases, including, for example, uracil, adenine, thymine, cytosine, guanine, inosine, xanthine hypoxanthine, isocytosine, isoguanine. A nucleic acid sequence corresponding to a signature gene can be a portion of the gene, a regulatory sequence, genomic DNA, cDNA, RNA including mRNA and rRNA, or others.

A nucleic acid sequence corresponding to a signature gene can be derived from a biological sample, or from a secondary source such as a product of a reaction such as, for example, a detection sequence from an invasive cleavage reaction, a ligated probe from an OLA or DASL reaction, an extended probe from a PCR reaction, or PCR amplification product, ("amplicon").

A complementary nucleic acid sequence useful in the methods of the invention can take many forms and probes are made to hybridize to nucleic acid sequences to determine the presence or absence of the signature gene in a sample. In a preferred embodiment, a plurality of nucleic acid sequences is detected. As used herein, "plurality" or grammatical equivalents herein refers to at least 2, 10, 20, 25, 50, 100 or 200 different nucleic sequences, while at least 500 different nucleic sequences is preferred. More preferred is at least 1000, with more than 5000 or 10,000 particularly preferred and more than 50,000 or 100,000 most preferred. Detection can be performed on a variety of platforms such as those set forth above.

The expression level of a signature gene in a tissue sample can be determined by contacting nucleic acid molecules derived from the tissue sample with a set of probes under conditions where perfectly complementary probes form a hybridization complex with the nucleic acid sequences corresponding to the signature genes, each of the probes including at least two universal priming sites and a signature gene target-specific sequence; amplifying the probes forming the hybridization complexes to produce amplicons; and detecting the amplicons, wherein the detection of the amplicons indicates the presence of the nucleic acid sequences corresponding to the signature gene in the tissue sample; and determining the expression level of the signature gene.

In the context of the present invention, multiplexing refers to the detection, analysis or amplification of a plurality of nucleic acid sequences corresponding to the signature genes. In one embodiment multiplex refers to the number of nucleic acid sequences corresponding to a signature gene to be analyzed in a single reaction, vessel or step. The multiplexing method is useful for detection of a single nucleic acid sequence corresponding to a signature gene as well as a plurality of nucleic acid sequences corresponding to a set of signature genes.

The expression level of nucleic acid sequences corresponding to a set of signature genes in a tissue sample can be determined by contacting nucleic acid molecules derived from the tissue sample with a set of probes under conditions where complementary probes form a hybridization complex with the signature gene-specific nucleic acid sequences, each of the probes including at least two universal priming sites and a signature gene-specific nucleic acid sequence; amplifying the probes forming the hybridization complexes to produce amplicons; detecting the amplicons, wherein the detection of the amplicons indicates the presence of the nucleic acid sequences corresponding to the set of signature genes in the tissue sample; and determining the expression level of the target sequences, wherein the expression of at least two, at least three, at least five signature gene-specific sequences is detected.

The presence of one, two or a plurality of nucleic acid sequences corresponding to a set of signature genes can be determined in a biological sample using single, double or multiple probe configurations. In addition, mRNA signature samples can initially be subjected to a "complexity reduction" step, whereby the presence of a particular target is confirmed by adding probes that are enzymatically modified in the presence of the signature gene-specific nucleic acid sequence. The modified probes are then amplified and detected in a wide variety of ways. Preferred embodiments draw on multiplexing methods, which allow for the simultaneous detection of a number of nucleic acid sequences, for example, corresponding to a set of signature genes, as well as multiplexing amplification reactions, for example by using universal priming sequences to do multiplex PCR reactions. If desired, the initial step also can be both a complexity reduction and an amplification step.

Probes contemplated for use in the assays and methods of the present invention can be made by any method known in the art, including the procedures outlined below.

In standard nucleic acid hybridization assays, probe must be is labeled in some way, and must be single stranded. Oligonucleotide probes are short (typically 15-50 nucleotides) single-stranded pieces of DNA made by chemical synthesis: mononucleotides are added, one at a time, to a starting mononucleotide, conventionally the 3' end nucleotide, which is bound to a solid support. Generally, oligonucleotide probes are designed with a specific sequence chosen in response to prior information about the target DNA. Oligonucleotide probes are often labeled by incorporating a $^{32}P$ atom or other labeled group at the 5' end.

Conventional DNA probes are isolated by cell-based DNA cloning or by PCR. In the former case, the starting DNA may range in size from 0.1 kb to hundreds of kilobases in length and is usually (but not always) originally double-stranded. PCR-derived DNA probes have often been less than 10 kb long and are usually, but not always, originally double-stranded.

DNA probes are usually labeled by incorporating labeled dNTPs during an in vitro DNA synthesis reaction by many different methods including nick-translation, random primed labeling, PCR labeling or end-labeling.

Labels can be radioisotopes such as $^{32}$P, $^{33}$P, $^{35}$S and $^{3}$H, which can be detected specifically in solution or, more commonly, within a solid specimen, such as autoradiography. $^{32}$P has been used widely in Southern blot hybridization, and dot-blot hybridization.

Nonisotopic labeling systems which use nonradioactive probes can also be used in the current invention. Two types of non-radioactive labeling include direct nonisotopic labeling, such as one involving the incorporation of modified nucleotides containing a fluorophore. The other type is indirect nonisotopic labeling, usually featuring the chemical coupling of a modified reporter molecule to a nucleotide precursor. After incorporation into DNA, the reporter groups can be specifically bound by an affinity molecule, a protein or other ligand which has a very high affinity for the reporter group. Conjugated to the latter is a marker molecule or group which can be detected in a suitable assay. This type of labeling would include biotin-streptavidin and digoxigenin.

The invention also includes a collection of isolated probes specific for the IFIG signature genes including any subset of the 83 genes in Table 2.

The invention also includes a collection of isolated probes specific for the neutrophil granule signature genes including any subset of the 24 genes in Table 3.

The invention also includes a collection of isolated probes specific for the neutrophil-related signature genes including any subset of the 23 genes in Table 4.

The invention also includes a collection of isolated probes specific for the genes, IFIT1, IFIT3, CEACAM6, LTF, TNFAIP6, CYP4F3 and FPR1.

The invention also includes a collection of isolated probes specific for the immunoglobulin/plasma cell genes including any subset of the 45 genes in Table 5.

The invention also includes a collection of isolated probes specific for the T-cell/iNKT signature genes including any subset of the 20 genes in Table 6.

The invention also includes a collection of isolated probes specific for the flare prediction signature genes comprising probes specific for IFIT3, KLRB1, CD38, and MMP8

Primers for use in the various assays of the present invention are also an embodiment of the present invention. The specificity of amplification depends on the extent to which the primers can recognize and bind to sequences other than the intended target DNA sequences. For complex DNA sources, such as total genomic DNA from a mammalian cell, it is often sufficient to design two primers about 20 nucleotides long. This is because the chance of an accidental perfect match elsewhere in the genome for either one of the primers is extremely low, and for both sequences to occur by chance in close proximity in the specified direction is normally exceedingly low. Although conditions are usually chosen to ensure that only strongly matched primer-target duplexes are stable, spurious amplification products can nevertheless be observed. This can happen if one or both chosen primer sequences contain part of a repetitive DNA sequence, and primers are usually designed to avoid matching to known repetitive DNA sequences, including large runs of a single nucleotide After the primers are added to denatured template DNA, they bind specifically to complementary DNA sequences at the target site. In the presence of a suitably heat-stable DNA polymerase and DNA precursors (the four deoxynucleoside triphosphates, dATP, dCTP, dGTP and dTTP), they initiate the synthesis of new DNA strands which are complementary to the individual DNA strands of the target DNA segment, and which will overlap each other Proteins Correlated to Clinical Manifestations of SLE As stated above, and shown in Examples 3, certain genes were associated with increased levels of certain anti-inflammatory proteins and with an increase in anti-SSA/Ro autoantibodies. Specifically, those subjects with SLE and the neutrophil-related gene signature also had an increase in TNF-α, IL-8, and IL-18, while those who had the neutrophil granule signature had an increase in anti-SSA/Ro autoantibodies. Thus, in order to confirm the clinical manifestations and disease activity associated with each of the gene signatures, additional tests for these proteins can be done on the subject with SLE, in conjunction with the tests detecting the signature genes.

A positive result of these biomarkers along with the gene biomarkers can confirm the activity and severity of the disease as well as the clinical manifestations. More specifically, a positive result of TNF-α, IL-8, and IL-18 with a positive result for IFIG and neutrophil-related gene would indicate an increase in flares as well as mucocutaneous involvement. A positive result of TNF-α.IL-8, and IL-18 along with an increase in IFIG only would indicate mucocutaneous involvement.

Patients can also be tested for anti-SSA/Ro autoantibodies. A positive result for the antibodies along with a positive result for IFIG and neutrophil granule signature genes, would confirm a prediction of the most serious active disease state of SLE with vascular involvement. A positive result for the antibodies with a positive result of the neutrophil granule signature genes only would confirm an increase in flares and activity of SLE along with vascular involvement.

As shown in Example 6, IL-10 and more significantly, vWF are increased during high disease activity, i.e., flares. These protein biomarkers can be used in conjunction with the four gene signature biomarkers, and more preferably, with the IFIG, neutrophil granule, and plasma cell gene signatures, to monitor a patient's response to treatment, either in regular care or in clinical trials.

These biomarkers, in addition to being useful for clinicians to predict disease activity, are also useful as targets for developing therapies and research tools.

Assays and Methods to Detect Proteins

A sample of biological tissue or bodily fluid from a subject with SLE, is obtained.

The protein sample can be obtained from any biological tissue. Preferred biological tissues include, but are not limited to, epidermal, whole blood, and plasma.

The protein sample can be obtained from any biological fluid. Preferred fluids include, but are not limited to, plasma, saliva, and urine.

Protein is isolated and/or purified from the sample using any method known in the art, including but not limited to immunoaffinity chromatography.

Any method known in the art can be used, but preferred methods for detecting and measuring increase levels of the proteins in a protein sample include quantitative Western blot, immunoblot, quantitative mass spectrometry, enzyme-linked immunosorbent assays (ELISAs), radioimmunoassays (RIA), immunoradiometric assays (IRMA), and immunoenzymatic assays (IEMA) and sandwich assays using monoclonal and polyclonal antibodies.

Antibodies are a preferred method of detecting and measuring the inflammatory proteins in a sample. Such antibodies are available commercially or can be made by conventional methods known in the art. Such antibodies can be monoclonal or polyclonal and fragments thereof, and immunologic binding equivalents thereof. The term "antibody" means both a homologous molecular entity as well as a mixture, such as a serum product made up of several homologous molecular entities.

In a preferred embodiment, such antibodies will immunoprecipitate the inflammatory proteins from a solution as well as react with inflammatory proteins on a Western blot, immunoblot, ELISA, and other assays listed above.

Antibodies for use in these assays can be labeled covalently or non-covalently with an agent that provides a detectable signal. Any label and conjugation method known in the art can be used. Labels, include but are not limited to, enzymes, fluorescent agents, radiolabels, substrates, inhibitors, cofactors, magnetic particles, and chemiluminescent agents.

Methods of Treatment and Monitoring and Targeting Treatment

Current treatments for systemic lupus erythematosus are guided by the individual patient's manifestations, and include non-steroidal anti-inflammatory agents, anti-malarial agents, corticosteroid agents, and immunosuppressants. Fever, rash, musculoskeletal manifestations, and serositis generally respond to treatment with hydroxychloroquine, nonsteroidal anti-inflammatory drugs (NSAIDS), and steroids in low to moderate doses, as necessary, for acute flares. Medications such as methotrexate may be useful in chronic lupus arthritis, and azathioprine and mycophenolate have been widely used in lupus of moderate severity.

Nonsteroidal anti-inflammatory agents (NSAIDS) provide symptomatic relief for arthralgias, fever, headache, and mild serositis. NSAIDS include: ibuprofen, naproxen, and diclofenac.

Anti-malarial agents work with subtle immunomodulation without causing overt immunosuppression. These drugs are useful in preventing and treating lupus skin rashes, constitutional symptoms, arthralgias, and arthritis. Anti-malarials also help to prevent lupus flares and have been associated with reduced morbidity and mortality in SLE patients followed in observational trials. Anti-malarial drugs include hydroxychloroquine.

Corticosteroid agents are used predominantly for anti-inflammatory activity and as immunosuppressants. Preparations include oral, intravenous, topical, and intra-articular injections. Corticosteroids include methylprednisolone, which is used for acute organ-threatening exacerbations.

Prednisone is the most common immunosuppressant for treatment of autoimmune disorders and is the steroid most commonly prescribed for lupus. Low-dose oral prednisone can be used for milder SLE, but more severe involvement necessitates high doses of oral or intravenous therapy Prednisone is usually given as tablets that come in 1, 5, 10, or 20 milligram (mg) doses. Pills may be taken as often as 4 times a day or as infrequently as once every other day. Usually, a low dose of prednisone is less than 20 mg/day, a medium dose is between 7.5 and 30 mg per day, and a dose of more than 30 mg qualifies as a high dose.

Lupus flares can be treated with an intra-muscular (IM) injection of a drug called Triamcinolone.

Disease-modifying anti-rheumatic drugs (DMARDS) are immunomodulatory agents that act as immunosuppressives and cytotoxic and anti-inflammatory medications. The specific agent selection is generally indicated by the patient's organ involvement and disease severity. Due to toxicity, cyclophosphamide is reserved for severe organ-threatening disease. At the other end of the spectrum, methotrexate or azathioprine may be helpful for milder arthritis or skin disease. DMARDS can be used in patients whose condition has had an inadequate response to glucocorticoids.

Cyclophosphamide is used for immunosuppression in cases of serious SLE organ involvement, especially severe CNS involvement, vasculitis, and lupus nephritis.

Methotrexate is used for managing arthritis, serositis, cutaneous, and constitutional symptoms. It blocks purine synthesis and 5-aminoimidazole-4-carboxamide ribonucleotide (AICAR), thus increasing anti-inflammatory adenosine concentration at sites of inflammation. Methotrexate ameliorates symptoms of inflammation and is particularly useful in arthritis treatment.

Azathioprine is an immunosuppressant and a less toxic alternative to cyclophosphamide. It is used as a steroid-sparing agent in nonrenal disease.

Mycophenolate is useful for maintenance in lupus nephritis and other serious lupus cases. This agent inhibits inosine monophosphate dehydrogenase (IMPDH) and suppresses de novo purine synthesis by lymphocytes, thereby inhibiting their proliferation. Mycophenolate also inhibits antibody production.

Intravenous immune globulin is used for immunosuppression in serious SLE flares.

Belimumab inhibits the biologic activity of B-lymphocyte stimulator (BLyS), a naturally occurring protein required for survival and for development of B-lymphocyte cells into mature plasma B cells that produce antibodies. In autoimmune diseases, elevated BLyS levels are thought to contribute to production of autoantibodies. This agent is indicated for active, autoantibody-positive SLE in patients in whom standard therapy, including corticosteroids, antimalarials, immunosuppressives, and nonsteroidal anti-inflammatory drugs, is failing.

Additionally, medications are often used by doctors to treat other conditions that commonly occur in patients with lupus. Although these drugs do not specifically address the underlying cause of lupus, they are used to treat other conditions that may be compounded or indirectly caused by lupus.

Aspirin—Low doses of aspirin are often recommended for lupus patients who have antiphospholipid antibodies and may reduce the risk of heart attack and stroke.

Antiplatelet Medications (Platelet Antagonists)—Some lupus patients are at an increased risk for blood clots due to the prevalence of a condition known as antiphospholipid antibody syndrome (APS). Platelet antagonists help prevent these clots and in doing so, also help to prevent heart attack, stroke, and other complications.

Osteoporosis Medications (Bisphosphonates)

Anti-hypertensives—25-30% of people with lupus experience hypertension. The most common causes of high blood pressure in people with lupus are kidney disease and long-term steroid use.

Anticoagulants—Anticoagulants are important to prevent and treat thromboembolisms, a condition associated with anti-phospholipid antibodies.

Gastrointestinal Medications

Statins—Studies have shown that people with lupus are more likely to have clogged arteries that can lead to heart attack and stroke at a younger age.

Thyroid Medications—Autoimmune thyroid disease is common in lupus. It is believed that about 6% of people with lupus have hypothyroidism (underactive thyroid) and about 2% have hyperthyroidism (overactive thyroid).

Fibromyalgia Medications

Restasis

Patients diagnosed with SLE are counseled to see their clinician or health care provider at least quarterly for monitoring and testing.

The current invention provides methods for providing treatment based upon valid predictions as to the severity of SLE as well as the clinical manifestations. In this manner, a subject diagnosed with SLE can be treated more effectively with agents that target the particular clinical manifestations and the severity of the disease. Using the biomarkers provided herein for the first time allows clinicians and health care providers to tailor treatment more specifically based upon the profile of the patient.

By way of example, a clinician or health care provider treating a subject, who after testing is categorized in group A, the group most similar to the healthy donors, would most likely treat the subject less aggressively. Treatment options may include low doses of prednisone, and NSAIDs, or optionally no treatment and normal monitoring, i.e., quarterly.

A clinician or health care provider treating a subject, who after testing is categorized in group C1 or C2, would most likely treat the subject very aggressively, with agents that target vascular and renal manifestations, and severe flares, even if the subject has not manifested overt symptoms. These agents would include, but are not limited to, corticosteroids such as prednisone in a medium to high dose (7.5 to over 30 mg/day) or intravenous methylprednisolone in a high doses (known as pulse therapy, using greater than 50 mg/day for 1-3 days); cytotoxic drugs, such as cyclophosphamide; immunosuppressive drugs, such as mycophenolate mofetil or azathioprine; biologic agents, such as rituximab; and anti-malarial drugs, such as hydroxychloroquine, as well as agents targeting the vascular system, including but not limited to anti-hypertensive drugs, statins, and anti-coagulants such as aspirin and coumarin. Additionally, the subject would be monitored more frequently than normal, e.g., monthly or weekly. These subjects would also be counseled to maintain habits that promote good vascular health, such as regular exercise, a low-fat diet, and no smoking.

A clinician or health care provider treating a subject, who after testing is categorized in group B1 or B2 would most likely treat the subject aggressively, with agents that target mucocutaneous manifestations of SLE, and increased flares. These agents would include, but are not limited to, corticosteroids, such as prednisone in a low to medium dose (less than 20 mg/day); anti-malarial medications, such as hydroxychloroquine, and immunosuppressive agents, such as azathioprine, dapsone, and thalidomide, as well as topical agents that target mucocutaneous disorders, including but not limited to, topical corticosteroids. These subjects would typically be monitored less than monthly, e.g., quarterly, and would be especially counseled to avoid sunlight.

A clinician or health care provider treating a subject, who after testing is determined to be likely to have future flares, would most likely treat the subject aggressively, with agents including but not limited to, corticosteroids, such as prednisone in a medium to high dose (7.5 to over 30 mg/day), or intravenous methylprednisolone in a high doses (known as pulse therapy, using greater than 50 mg/day for 1-3 days); cytotoxic drugs, such as cyclophosphamide; immunosuppressive drugs, such as mycophenolate, mofetil or azathioprine; biologic agents, such as rituximab; and anti-malarial drugs, such as hydroxychloroquine, as well as increasing the dose of any therapeutic agents currently be used by the subject, and monitoring the subject more frequently than normal, e.g., monthly or more frequently.

A clinician or health care provider treating a subject who determines that the subject is in a current flare, would likely focus the treatment on targets including, genes from the IFIG signature, the neutrophil granule signature, the plasma cell signature, the T-cell/iNKT signature, vWF and/or IL-10. Therapeutic agents that target vWF include, but are not limited to, ARC-1779 aptamer (Archemix-Baxter, Deerfield, Ill.), ALX-0081 Nanobody (Ablynx, Belgium), and rPGP 290 (Aarvon Bioscience, Woburn, Mass.).

The current invention also provides methods for monitoring subjects and their responses to treatment, e.g, administration of agents, both oral and topical, life style alterations such as diet and exercise, and non-traditional treatment such as acupuncture. This is useful in both patient care as well as clinical trials. Such a method comprises obtaining the expression of at least one gene in at least one gene signature in a subject prior to any treatment. After a course of treatment at a particular time period that a person of skill in the art can determine, the measurement of expression of the same gene or genes is measured, and a decrease in expression would indicate the agent is effectively treating or ameliorating the subject's SLE. The expression of at least one gene in at least one gene signature would be measured before and after treatment. In a preferred embodiment at least one gene from each gene signature would be measured. Genes in any of the five signatures can be used. In a more preferred embodiment, more than one gene from each signature would be measured. In treatments that are to target vascular manifestations of disease, genes from the IFIG and neutrophil granule signature would be used, along with anti-SSA/Ro antibodies. For treatments that are to target mucocutaneous manifestations of the disease, genes from the IFIG and neutrophil-related signature, along with TNF-α, IL-8, and IL-18 would be used.

In a preferred embodiment, one gene from each of the IFIG, neutrophil granule, and the neutrophil-related signature would be measured, and in a more preferred embodiment, IFIT1, IFIT3, ANXA3, ARG1, MPO, DEFA1, LTF, CEACAM6, TNFAIP6, FPR1, FPR2, LY96, CYP4F3, IL1R2, PRRG4, and DOCK4, would be measured before and after treatment. In another embodiment, TNF-α, IL-8, IL-18, and anti-SSA/Ro antibodies are also measured before and after treatment.

In another preferred embodiment, genes from each of the IFIG, neutrophil granule, and plasma cell signature would be measured, and in a more preferred embodiment, IFIT3, MMP8, and CD38 are measured. In a preferred embodiment, vWF and/or IL-10 are also measured before and after treatment. These biomarkers would monitor the effectiveness of a treatment for active disease.

The present invention also provides a method for determining target genes or proteins for drug development. For example, a clinical trial that has been determined to target vascular manifestations of SLE would target genes in the IFIG signature, and the neutrophil signature, as well as anti-SSA/Ro antibodies. A clinical trial that has been determined to target mucocutaneous manifestations would target genes in the IFIG signature and the neutrophil-related signature, along with TNF-α, IL-8, and IL-18. A clinical trial that has been determined to target the active stages of the disease, i.e., flares, would target genes from the IFIG, neutrophil granule, plasma cell, and T-cell/iNKT signature as well as vWF and IL-10.

The invention also contemplates that the protein products of any of the genes in the gene signatures found in Tables 2-6 would also be potential therapeutic targets for either monitoring or drug development.

Kits

It is contemplated that all of the assays disclosed herein can be in kit form for use by a health care provider and/or a diagnostic laboratory.

Assays for the detection and quantitation of one or more of the gene signatures can be incorporated into kits. Such kits would include probes for one or more of the genes from one or more signatures, i.e., IFIG, neutrophil granule, neutrophil-related, immunoglobulin/plasma cell signature and T-cell/iNKT, reagents for isolating and purifying nucleic acids from biological tissue or bodily fluid, reagents for performing assays on the isolated and purified nucleic acid, instructions for use, and reference values or the means for obtaining reference values in a control sample for the included genes.

A preferred kit for patient classification with regard to disease activity and clinical manifestations would include probes for at least one gene from each of the three signatures, IFIG, neutrophil granule and neutrophil-related. A more preferred embodiment would include probes for IFIT1, IFIT3, CEACAM6, TNFAIP6, CYP4F3 and FPR1.

In a further embodiment, the kit would include reagents for testing for TNF-α, IL-8, and IL-18, and/or anti-SSA/Ro autoantibodies. Such a kit could include antibodies that recognize the peptide of interest, reagents for isolating and/or purifying protein from a biological tissue or bodily fluid, reagents for performing assays on the isolated and purified protein, instructions for use, and reference values or the means for obtaining reference values for the quantity or level of peptides in a control sample.

A preferred kit for monitoring treatment to disease activity would include probes from at least one gene from each of the three signatures, IFIG, neutrophil granule, and, immunoglobulin/plasma cell, and reagents for testing for vWF and IL-10. Such a kit could include antibodies that recognize the peptide of interest, reagents for isolating and/or purifying protein from a biological tissue or bodily fluid, reagents for performing assays on the isolated and purified protein, instructions for use, and reference values or the means for obtaining reference values for the quantity or level of peptides in a control sample.

A preferred kit for predicting future flares would include probes for at least one gene from each of the four signatures, IFIG, neutrophil granule, immunoglobulin/plasma cell signature and T-cell/iNKT. A more preferred embodiment would include probes for IFIT3, KLRB1, CD38, and MMP8.

A preferred embodiment of these kits would have the probes attached to a solid state. A most preferred embodiment would have the probes in a microarray format wherein nucleic acid probes for one or more of the genes from one or more of the gene signatures would be in an ordered arrangement on a surface or substrate.

Drug Screening Assays and Research Tools

All of the biomarkers disclosed herein can be used as the basis for drug screening assays and research tools.

In one embodiment, polypeptides and proteins encoded by the transcripts in the gene signatures, IFIG, neutrophil granule, neutrophil-related, plasma cell, and T-cells/iNKT, as well as vWF, IL-10, TNF-α, IL-8 and IL-18, can be used in drug screening assays, free in solution, or affixed to a solid support. All of these forms can be used in binding assays to determine if agents being tested form complexes with the peptides, proteins or fragments, or if the agent being tested interferes with the formation of a complex between the peptide or protein and a known ligand.

Thus, the present invention provides for methods and assays for screening agents for treatment of SLE, comprising contacting or incubating the test agent with a polypeptide or protein encoded by a gene in one of the gene signatures listed in Tables 2, 3, 4, 5, or 6, or vWF, IL-10, TNF-α, IL-8 and IL-18, and detecting the presence of a complex between the polypeptide and the agent or the presence of a complex between the polypeptide and a ligand, by methods known in the art. In such competitive binding assays, the polypeptide or fragment is typically labeled. Free polypeptide is separated form that in the complex, and the amount of free or uncomplexed polypeptide is measured. This measurement indicates the amount of binding of the test agent to the polypeptide or its interference with the binding of the polypeptide to a ligand.

High throughput screening can also be used to screen for therapeutic agents. Small peptides or molecules can be synthesized and bound to a surface and contacted with the polypeptides encoded by the gene signature transcripts, and washed. The bound peptide is visualized and detected by methods known in the art.

Antibodies to the polypeptides can also be used in competitive drug screening assays. The antibodies compete with the agent being tested for binding to the polypeptides. The antibodies can be used to find agents that have antigenic determinants on the polypeptides, which in turn can be used to develop monoclonal antibodies that target the active sites of the polypeptides.

The invention also provides for polypeptides to be used for rational drug design where structural analogs of biologically active polypeptides can be designed. Such analogs would interfere with the polypeptide in vivo, such as by non-productive binding to target. In this approach the three-dimensional structure of the protein is determined by any method known in the art including but not limited to x-ray crystallography, and computer modeling. Information can also be obtained using the structure of homologous proteins or target-specific antibodies.

Using these techniques, agents can be designed which act as inhibitors or antagonists of the polypeptides, or act as decoys, binding to target molecules non-productively and blocking binding of the active polypeptide.

Polypeptides encoded by any of the differentially expressed transcripts of the gene signatures found in Tables 2, 3, 4, 5, and 6 can be used. Additionally, testing can be done as described above using the proteins or fragments of the proteins vWF, IL-10, TNF-α, 11-8, and IL-18, as well as anti-SS/Ro antibodies.

A further embodiment of the present invention is gene constructs comprising any one of the differentially expressed transcripts and a vector. These gene construct can be used for testing of therapeutic agents as well as basic research regarding SLE. These gene constructs can also be used to transform host cells can be transformed by methods known in the art.

The resulting transformed cells can be used for testing for therapeutic agents as well as basic research regarding SLE. Specifically, cells can be transformed with any one of the differentially expressed transcripts, and contacted with a test agent. The resulting expression of the transcript can be detected and compared to the expression of the transcript in the cell before contact with the agent.

The expression of the transcripts in host cells can be detected and measured by any method known in the art, including but not limited to, reporter gene assays.

These gene constructs as well as the host cells transformed with these gene constructs can also be the basis for transgenic animals for testing both as research tools and for therapeutic agents. Such animals would include but are not limited to, nude mice. Phenotypes can be correlated to the genes and looked at in order to determine the genes effect on the animals as well as the change in phenotype after administration or contact with a potential therapeutic agent.

The gene constructs and host cells transformed with the gene constructs can also be administered to murine models of SLE, for analyzing test agents as well as basic research.

Any of the differentially expressed transcripts of the gene signatures found in Tables 2, 3, 4, 5, and 6 can be used.

EXAMPLES

The present invention may be better understood by reference to the following non-limiting examples, which are presented in order to more fully illustrate the preferred embodiments of the invention. They should in no way be construed to limit the broad scope of the invention.

Example 1

Patients and Methods

Study Subjects

All patients fulfilled at least four of the American College of Rheumatology (ACR) criteria for SLE (Tan et al. 1982). Two cohorts of SLE patients were studied: a training set of 23 SLE patients, and a validation set of 58 SLE patients. Demographic and clinical data of the study patients are summarized in Table 7.

Episodes of mild/moderate and severe flare were established based on the Safety of Estrogens in Lupus Erythematosus: National Assessment—SLE Disease Activity Index [SELENA-SLEDAI (SLEDAI)] score (American College of Rheumatology Ad Hoc Committee on Systemic Lupus Erythematosus Response Criteria 2004). Mild or moderate flares were defined as an increase in SLEDAI score of more than 3 points from the previous visit. Severe flare was defined as change in SLEDAI to greater than 12. New organ flares or requirement for medical intervention were also considered flares. Longitudinal clinical data, along with PBMC and plasma samples, were obtained over an average of 9 visits (range 2-26) for SLE patients and 5 visits for HD. The duration of study follow-up for individual patients, averaged 860 days and ranged from 63 to 1941 days.

Biologic Sample Collection

Blood samples from HD and SLE patients were processed within one hour of phlebotomy. Peripheral blood mononuclear cells ("PBMC") were purified using Ficoll-Paque™Plus (GE Healthcare Life Sciences, Piscataway, N.J.) gradient centrifugation and preserved in RNeasy lysis buffer (QIAGEN, Inc., Valencia, Calif.). Samples were stored at −70° C. until RNA extraction.

RNA Isolation, Amplification, and Hybridization

RNA was isolated from 169 PBMC samples using the RNeasy kit (QIAGEN) and quality assessed using the Agilent 2100 Bioanalyzer. Fifty nanograms of total RNA was used to prepare targets by Two-Cycle Target labeling kit (Affymetrix, Santa Clara, Calif., USA) following the manufacturer's instructions and hybridized onto Human Genome U133 Plus 2.0 GeneChips® (Affymetrix) at 45° C. overnight. Chips were scanned in a GeneChip® scanner 3000 (Affymetrix).

Proteomic Study of Plasma Proteins

Plasma levels of 44 autoantibodies (autoimmune serology panel) and 41 inflammatory biomarkers (human inflammation panels ver1.0) were evaluated using the multi-analyte profiling (MAP) technology (Rules-Based Medicine, Austin, Tex.). The protein analytes included in this assay are listed in Table 8.

Microarray Data Analysis and Quality.

Data from the Affymetrix U133 Plus 2.0 gene arrays (CEL files) were uploaded to GeneSpring GX11 software (Agilent Technologies, Santa Clara, Calif.), processed using the robust multiarray analysis algorithm (Irizarry et al. 2003) and log-transformed. Each *.CEL file represents an individual subject's visit. Affymetrix Expression Console software ver 1.1 was used to generate a detection p-value, which indicates the reliability of detection of the transcripts above background on the array. Probe-sets with a detection p-value greater than 0.05 in more than 30% of HDs or SLE patients were excluded from the analysis.

Proteomics Data Analysis.

Analytes below the detectable level in more than 50% of the SLE samples were excluded from analysis. The remaining low data points were adjusted to the least detectable level. All data are presented as a mean±standard deviation. Serology results were calculated as a ratio of the median fluorescence intensity (MFI) of reactivity with a specific antigen to a negative control. Data were normalized to the mean of each parameter, log2 transformed for data visualization as well as for statistical and clustering analysis. P-values less than 0.05 were considered significant after multiple samples correction (5% FDR). Fold change differences were calculated between geometric means and therefore were lower compared to fold change differences between arithmetic means. Fold change of more than 1.5 was considered significant.

Statistical Analysis of Microarray and Proteomics Data

A linear mixed effects model was used to analyze gene expression and proteomics data that included repeated measurements over time in individual patients and HDs, permitting estimation of variability among patient groups and based on flare status.

In experiments with a repeated measurements design it is possible to accurately estimate the variability for expression of each gene between groups using a linear mixed model (Karlovich et al. 2009).

The simplest model would include two sources of variation in measured gene intensities: patient to patient variability and within patient variability. Let $Y_{jt}$ be the base 2 algorithm of normalized gene intensities of a particular gene transcript, i the studied groups [HD or SLE], j the donor [j=1, . . . , 28], and t refers to time points. A linear model for the type of analysis herein is:

$$Y_{jt} = \mu + \text{Time}_{jt} + \text{Group}_j + T_{jt} + P_j + \epsilon_{jt} \qquad (1)$$

where µ=the grand mean, $\text{Time}_{jt}$=average deviance from µ due to effect of time, $\text{Group}_j$=average deviance from µ due to effect of disease, Tjt and $P_j$=random effect of time and donor correspondingly and $\epsilon_{jt}$=are the additive stochastic errors.

The model could be extended with the addition of the effect of SLE flares. In that case the additional fixed effect of flares should be added.

$$Y_{jt} = \mu + \text{Time}_{jt} + \text{Group}_j + \text{Flarejt} + T_{jt} + P_j + \epsilon_{jt} \qquad (2)$$

Flarej=the effect of flares (non-flaring or flaring).

Such models are both examples of generalized linear models and could be written in terms of the equation:

$$Y = X\beta + Z\mu + \epsilon \quad (3)$$

Where Y is a vector of n observations, β is a vector of fixed effect, μ is a vector of random effect (equal to the number of patients), ε is a vector of residual errors, X and Z are incidence matrices for the fixed and random effects.

The model is fitted to the data employing R(R Development Core Team, 2012) and package lme4 (Bates and Maechler, 2009) under the important assumption that the residuals and patient p terms are normally distributed. Quantitatively, the hypothesis that the residual terms are normally distributed may be tested with the Shapiro normality test ($p<0.1$).

To assess the validity of the mixed effect analyses, likelihood ratio tests were performed comparing the model with fixed effect to the null models with only random effect from donors. Results in which the model including fixed effects did not differ from the null model were rejected.

For each gene, fold change difference between groups was calculated based on log-means level for each donor. For each gene a generalized F-test was performed based on the described model and the corresponding p-values were obtained. Alternatively, because it is debated whether the degree of freedom is a meaningful concept for linear mixing models, p-values based on log likelihood ratio testing were obtained (shown in tables). Whenever it was possible, the model followed by Markov chain sampling was used for more exact p values. Because numerous F-tests were performed, a multiple testing correction procedure to control erroneously identified genes was applied.

Hierarchical Clustering

Clustering of patients based on transcripts or analytes was performed using R package function hclust. The program's parameters used included Pearson's centered, ward for patient classification based on differentially expressed transcripts, and Euclidian centered, centroid for classification based on autoantibodies. The results of the hierarchical clustering are represented using "heatmap" plots, with the orange color indicating high expression and blue corresponding to low expression of transcripts. In some cases, due to the repetitive nature of experiments, average levels of all time points for each transcript/analyte per patient was calculated before clustering analysis.

TABLE 7

General subject demographic and clinical characteristics

|  | HD | SLE (training) | SLE (validation) |
|---|---|---|---|
| Total subjects | 5 | 23 | 58 |
| Male | 2 (40%) | 4 (17%) | 7 (12%) |
| Median Age, years (Range) | 38 (35-44) | 27 (14-50) | 28 (17-57) |
| Asian Americans (%) | 1 (20%) | 3 (13%) | 4 (7%) |
| Black Americans (%) | 0 (0%) | 6 (26%) | 24 (41%) |
| Hispanic Americans (%) | 2 (40%) | 8 (35%) | 19 (33%) |
| European Americans (%) | 1 (20%) | 5 (22%) | 10 (17%) |
| Other/Mix (%) | 1 (20%) | 1 (4%) | 1 (2%) |
| Median disease duration, years (range) |  | 7 (0-16) | 3 (0-24) |
| Median ACR Score, (range) |  | 6 (3-9) | 6 (2-9) |
| SLEDAI (at study initiation), Median, (range) |  | 6 (0-25) | 4 (0-16) |
| SLEDAI (at study endpoint), Median, (range) |  | 4 (0-18) | 4 (0-18) |
| BILAG (at study initiation), Median, (range) |  | 7 (1-34) | 5 (0-16) |
| BILAG (at study endpoint), Median, (range) |  | 1 (0-14) | 2 (0-15) |

TABLE 8

Analytes studied in proteomics assay

|  | Analytes | Units | Least Detectable Dose (LDD) | Low Plasma Range | High Plasma Range | Samples below LDD in HD (25) | Samples below LDD in SLE (144) | % Low in HD | % Low in SLE |
|---|---|---|---|---|---|---|---|---|---|
| 1 | Alpha-2 Macroglobulin | mg/mL | 0.017 | 0.13 | 1 | 0 | 0 | 0% | 0% |
| 2 | Alpha-1 Antitrypsin | mg/mL | <0.0029 | 1.2 | 3.1 | 0 | 0 | 0% | 0% |
| 3 | Beta-2 Microglobulin | ug/mL | 0.24 | 1.2 | 6.2 | 0 | 3 | 0% | 2% |
| 4 | Brain-Derived Neurotrophic | ng/mL | 0.044 | 0.32 | 16 | 0 | 2 | 0% | 1% |
| 5 | Complement 3 | mg/mL | <0.0024 | 0.76 | 2.1 | 0 | 0 | 0% | 0% |
| 6 | C Reactive Protein | ug/mL | 0.038 | 0.25 | 50 | 0 | 0 | 0% | 0% |
| 7 | Eotaxin | pg/mL | 118 |  | 177 | 0 | 2 | 0% | 1% |
| 8 | Factor VII | ng/mL | 9 | 106 | 443 | 0 | 0 | 0% | 0% |
| 9 | Ferritin | ng/mL | 3.3 | 5 | 552 | 0 | 0 | 0% | 0% |
| 10 | Fibrinogen | mg/mL | 0.0052 | 2.2 | 8 | 0 | 2 | 0% | 1% |
| 11 | Haptoglobin | mg/mL | 0.0061 | 0.047 | 7.6 | 0 | 11 | 0% | 8% |
| 12 | ICAM-1 | ng/mL | 2.7 | 42 | 213 | 0 | 0 | 0% | 0% |
| 13 | IL-10 | pg/mL | 5.4 | 1.8 | 38 | 1 | 0 | 4% | 0% |
| 14 | IL-12p70 | pg/mL | 50 |  | 165 | 18 | 63 | 72% | 44% |
| 15 | IL-15 | ng/mL | 0.2 |  | 4.6 | 9 | 37 | 36% | 26% |
| 16 | IL-18 | pg/mL | 20 | 72 | 1020 | 0 | 0 | 0% | 0% |
| 17 | IL-1ra | pg/mL | 38 | 17 | 622 | 0 | 0 | 0% | 0% |
| 18 | IL-23 | ng/mL | 1.2 |  | 30 | 3 | 8 | 12% | 6% |
| 19 | IL-6 | pg/mL | 5.9 |  | 25 | 13 | 4 | 52% | 3% |
| 20 | IL-8 | pg/mL | 3.3 |  | 59 | 1 | 0 | 4% | 0% |
| 21 | MCP-1 | pg/mL | 8.8 | 35 | 401 | 0 | 0 | 0% | 0% |
| 22 | MIP-1alpha | pg/mL | 11 |  | 89 | 14 | 42 | 56% | 29% |
| 23 | MIP-1beta | pg/mL | 21 | 25 | 595 | 0 | 0 | 0% | 0% |

TABLE 8-continued

Analytes studied in proteomics assay

| | Analytes | Units | Least Detectable Dose (LDD) | Low Plasma Range | High Plasma Range | Samples below LDD in HD (25) | Samples below LDD in SLE (144) | % Low in HD | % Low in SLE |
|---|---|---|---|---|---|---|---|---|---|
| 24 | MMP-3 | ng/mL | 0.21 | | 1.8 | 0 | 0 | 0% | 0% |
| 25 | RANTES | ng/mL | 0.28 | 2.6 | 83 | 0 | 0 | 0% | 0% |
| 26 | Stem Cell Factor | pg/mL | 74 | | 281 | 0 | 0 | 0% | 0% |
| 27 | TIMP-1 | ng/mL | 7 | 59 | 192 | 0 | 0 | 0% | 0% |
| 28 | TNF-alpha | pg/mL | 3.6 | | 27 | 18 | 34 | 72% | 24% |
| 29 | TNF RII | ng/mL | 0.3 | 3.1 | 79 | 0 | 0 | 0% | 0% |
| 30 | VCAM-1 | ng/mL | 5.4 | 284 | 1310 | 0 | 0 | 0% | 0% |
| 31 | VDBP (Vitamin D Binding) | ug/mL | 4.9 | Pending | Pending | 0 | 0 | 0% | 0% |
| 32 | VEGF | pg/mL | 28 | 91 | 1790 | 0 | 0 | 0% | 0% |
| 33 | von Willebrand Factor | ug/mL | 0.43 | 5.3 | 74 | 0 | 0 | 0% | 0% |
| 34 | B-Lymphocyte Chemoattractant (BLC) | pg/ml | 55 | pending | pending | 1 | 0 | 4% | 0% |
| 35 | IP-10 (Inducible Protein-10) | pg/ml | 30 | pending | pending | 0 | 0 | 0% | 0% |
| 36 | MCP-2 | pg/ml | 15 | pending | pending | 1 | 0 | 4% | 0% |
| 37 | Gamma-Interferon-induced Monokine | pg/ml | 100 | pending | pending | 0 | 0 | 0% | 0% |
| 38 | Prolactin | ng/ml | 0.5 | 0.88 | 42 | 0 | 0 | 0% | 0% |
| 39 | BAFF | pg/ml | 11 | | | 0 | 0 | 0% | 0% |
| 40 | ITAC | pg/ml | 7.5 | | | 0 | 0 | 0% | 0% |
| 41 | MIP-3b | pg/ml | 14 | | | 0 | 0 | 0% | 0% |
| 42 | GM-CSF | pg/mL | 19 | | 152 | 25 | 143 | 100% | 99% |
| 43 | IFN-gamma | pg/mL | 3.6 | | 9.5 | 23 | 123 | 92% | 85% |
| 44 | IL-12p40 | ng/mL | 0.55 | | 2.7 | 25 | 144 | 100% | 100% |
| 45 | IL-17 | pg/mL | 8.5 | 14 | 80 | 25 | 144 | 100% | 100% |
| 46 | IL-1alpha | ng/mL | 0.0062 | | 0.35 | 25 | 103 | 100% | 72% |
| 47 | IL-1beta | pg/mL | 2 | | 8.7 | 19 | 100 | 76% | 69% |
| 48 | IL-2 | pg/mL | 14 | | 61 | 25 | 144 | 100% | 100% |
| 49 | IL-3 | ng/mL | 0.032 | | 1.2 | 25 | 144 | 100% | 100% |
| 50 | IL-4 | pg/mL | 12 | | 103 | 5 | 87 | 20% | 60% |
| 51 | IL-5 | pg/mL | 6.9 | | 62 | 18 | 118 | 72% | 82% |
| 52 | IL-7 | pg/mL | 16 | 3.7 | 125 | 25 | 144 | 100% | 100% |
| 53 | MMP-2 | ng/mL | 15 | 183 | 3070 | 25 | 129 | 100% | 90% |
| 54 | MMP-9 | ng/mL | 8.3 | | 1050 | 17 | 105 | 68% | 73% |
| 55 | TNF-beta | pg/mL | 8.9 | | 120 | 25 | 144 | 100% | 100% |
| 56 | MCP-3 | pg/mL | 17 | pending | pending | 25 | 111 | 100% | 77% |

Example 2

PBMC mRNA Transcripts Differentially Expressed Between SLE Patients and HDs Define Three Patient Groups Based on the statistical method described in Example 1, 433 differentially expressed probe-sets between HDs and SLE patients were identified (fold change (FC)>1.5, p<0.05, 5% false detection rate (FDR)), along with 9 transcripts due to the effect of flare status. See Table 9.

As SLE patients are known to exhibit activation of type 1 interferon genes in the PBMC, the present of interferon inducible genes ("IFIG") using the INTERFEROME database (Samarajiwa et al. 2009) was tested. The transcripts most highly expressed in SLE compared to HD samples were dominated by IFN-1-induced genes (IFIG) and neutrophil granule genes, consistent with previous reports. Approximately one quarter of transcripts (total number 112) were identified as interferon regulated genes, with the majority being regulated by type I interferon (96 genes by Type I versus 74 genes by Type II and 48 genes by Type III interferons).

Machine learning analysis is widely used for grouping transcripts showing similar expression pattern. An unsupervised hierarchical clustering was performed to classify both transcripts deregulated in SLE samples and HDs who participated in the study. For simplicity and gene visualization, the mean expression value for each transcript over all visits for each SLE patient and HD was used.

Top three clusters of genes, shown on the left side of dendrogram (FIG. 1), were suspected to be enriched with transcripts related to IFIG, neutrophil-granule genes and neutrophil related genes respectively. The presence of low-density granulocytes in blood preparations of lupus patients has been shown earlier (Denny et al. 2010).

FIG. 2 depicts the database and methods on how the functionality for corresponding clusters was assigned. FIG. 2A shows that the presence of IFIG within the assigned cluster (the top of FIG. 1) as determined using the INTERFEROME database.

FIG. 2B shows that genes with expression associated with primary, secondary and tertiary neutrophil granules transcripts were identified based on previously published microarray analysis of bone marrow and peripheral blood neutrophils by Theiland-Munch 2005. Some genes were specific for promyelocytes and metamyelocytes and not observed in peripheral blood. According to this analysis of second from the top cluster (NG as shown on FIG. 1) was enriched with neutrophil granules genes.

FIG. 2C shows using the Gene Enrichment Profiler, containing data from human normal primary tissues (126 tissues represented by 557 microarrays), it was determined the likely source of the transcripts deemed as neutrophil related (NR, third cluster from the top on FIG. 1). Expression profiles were processed to identify tissue specificity which was measured by an enrichment score. The resulting heat map demonstrates high enrichment of selected gene transcripts among human peripheral blood neutrophils. It should be noted that part of the neutrophil-granule genes and neutrophil related genes, based on INTERFEROME database analysis, are also interferon inducible genes and therefore assumed to be largely expressed on neutrophils compared to other.

The list of differentially expressed transcripts, their median intensity across all visits in SLE patients and HDs, their fold difference in expression in SLE patients compared to HDs and their level of significance are presented in Table 9.

Based on the heatmap shown in FIG. 1, HDs are clearly distinct from SLE patients. Hierarchical clustering classified SLE patients into three principal groups (A, B and C). Group A consisted of six patients that were placed close to the HDs. Group A patients generally hold levels of IFIG and neutrophil-granule transcripts similar to HD. The most populated group, C, included 12 patients. The majority of patients in group C show elevated expression of both IFIG and neutrophil-granule genes. Group B demonstrated prominent IFIG but lacks the neutrophil granule signature. Instead, a set of neutrophil related transcripts was increased.

In general this analysis confirmed the prominent overexpression of IFIG observed previously in PBMC of SLE patients (Crow et al. 2007; Crow et al. 2003; Lovgren et al. 2004; Barrat et al. 2005; Crow et al. 2003) and also demonstrated expression of neutrophil-granule transcripts in a distinct patient group C. Many of the latter genes have previously been detected in PBMC from pediatric lupus patients (Bennett et al. 2003). In addition, this analysis detected overexpression of neutrophil related transcripts within group B lupus patients.

The elevated levels of IFIG and neutrophil granule transcripts highlight their significance in distinguishing SLE patients from HDs. However, some of the differentially expressed transcripts, particularly those derived from samples collected at times of disease flare, may represent an acute-phase reaction rather than a characteristic feature of lupus. Linear mixed model analysis of gene expression data from all individual visits of all study subjects was used to identify those transcripts that reflect lupus disease as well as those that are associated with lupus flare. Using that approach, 131 probe-sets were identified with a significant effect related to lupus disease and lupus flares ($p<0.05$, 5% FDR). Those probe-sets are highlighted in bold in Table 9.

Of interest, well known IFIGs do not appear among those probe-sets associated with flare. Instead, a number of transcripts related to neutrophil granule genes as well as neutrophil related transcripts, including TNFAIP6, were among the 131 probe-sets identified by this analytical approach. In addition, lupus flares change the level of 9 probe-sets, which were normally expressed when patient was during non-flaring state (identified by an asterisk in Table 9.

Taken together, these analyses, based on multiple longitudinal PBMC samples from SLE patients and HDs, indicate that representative transcripts of the IFIG and neutrophil granule signatures was sufficient to define at least three distinct patient groups.

TABLE 9

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 202411_at | IFI27 | interferon, alpha-inducible protein 27 | 3429 | 22.00 | 21.1 | 1076.5 | 4.493 | 0.0002 | −0.028 | 0.9973 |
| 204439_at | IFI44L | interferon-induced protein 44-like | 10964 | 12.94 | 391.1 | 6548.2 | 3.708 | 0.0002 | −0.036 | 0.9594 |
| 213797_at | RSAD2 | radical S-adenosyl methionine domain containing 2 | 91543 | 11.35 | 128.9 | 1936.1 | 3.603 | 0.0002 | 0.160 | 0.7699 |
| 242625_at | RSAD2 | radical S-adenosyl methionine domain containing 2 | 91543 | 11.21 | 352.1 | 5038.5 | 3.556 | 0.0002 | 0.118 | 0.8528 |
| 203153_at | IFIT1 | interferon-induced protein with tetratricopeptide repeats 1 | 3434 | 8.87 | 492.1 | 5337.9 | 3.249 | 0.0002 | 0.172 | 0.7738 |
| 231688_at | MMP8 | matrix metallopeptidase 8 (neutrophil collagenase) | 4317 | 7.33 | 62.1 | 745.9 | 3.469 | 0.0002 | 1.160 | 0.0034 |
| 219519_s_at | SIGLEC1 | sialic acid binding Ig-like lectin 1, sialoadhesin | 6614 | 6.96 | 44.2 | 459.5 | 2.990 | 0.0002 | 0.118 | 0.8528 |
| 202018_s_at | LTF | lactotransferrin | 4057 | 6.59 | 678.9 | 4618.3 | 3.134 | 0.0002 | 0.818 | 0.0176 |
| 229450_at | IFIT3 | interferon-induced protein with tetratricopeptide repeats 3 | 3437 | 6.54 | 1095.4 | 7952.2 | 2.806 | 0.0002 | 0.144 | 0.7215 |
| 226702_at | CMPK2 | cytidine monophosphate (UMP-CMP) kinase 2, mitochondrial | 129607 | 6.02 | 726.8 | 4887.1 | 2.651 | 0.0002 | 0.095 | 0.7956 |
| 219211_at | USP18 | ubiquitin specific peptidase 18 | 11274 | 5.85 | 114.5 | 831.3 | 2.565 | 0.0002 | −0.054 | 0.9269 |
| 205483_s_at | ISG15 | ISG15 ubiquitin-like modifier | 9636 | 5.78 | 365.4 | 2470.2 | 2.624 | 0.0002 | 0.060 | 0.8948 |
| 207802_at | CRISP3 | cysteine-rich secretory protein 3 | 10321 | 5.75 | 45.9 | 408.2 | 2.991 | 0.0002 | 1.028 | 0.0125 |
| 202086_at | MX1 | myxovirus (influenza virus) resistance 1 ... | 4599 | 5.56 | 1051.0 | 6717.4 | 2.536 | 0.0002 | 0.048 | 0.8972 |
| 204415_at | IFI6 | interferon, alpha-inducible protein 6 | 2537 | 5.47 | 200.6 | 1292.1 | 2.567 | 0.0002 | 0.098 | 0.7595 |
| 204747_at | IFIT3 | interferon-induced protein with tetratricopeptide repeats 3 | 3437 | 5.16 | 143.2 | 914.6 | 2.516 | 0.0002 | 0.240 | 0.5221 |
| 205569_at | LAMP3 | lysosomal-associated membrane protein 3 | 27074 | 5.11 | 97.5 | 532.7 | 2.110 | 0.0002 | −0.374 | 0.0793 |
| 214453_s_at | IFI44 | interferon-induced protein 44 | 10561 | 4.99 | 900.2 | 4995.8 | 2.381 | 0.0002 | 0.056 | 0.8610 |
| 44673_at | SIGLEC1 | sialic acid binding Ig-like lectin 1, sialoadhesin | 6614 | 4.78 | 108.3 | 691.9 | 2.443 | 0.0002 | 0.111 | 0.8164 |
| 214059_at | IFI44 | Interferon-induced protein 44 | 10561 | 4.65 | 137.7 | 755.0 | 2.387 | 0.0002 | 0.213 | 0.5166 |
| 212768_s_at | OLFM4 | olfactomedin 4 | 10562 | 4.62 | 173.0 | 1550.3 | 2.820 | 0.0003 | 1.173 | 0.0084 |
| 212531_at | LCN2 | lipocalin 2 | 3934 | 4.61 | 217.3 | 1335.1 | 2.664 | 0.0002 | 0.860 | 0.0084 |
| 206177_s_at | ARG1 | arginase, liver | 383 | 4.24 | 87.1 | 645.5 | 2.653 | 0.0002 | 1.178 | 0.0034 |
| 218400_at | OAS3 | 2',5'-oligoadenylate synthetase 3, 100 kDa | 4940 | 4.21 | 394.9 | 1943.3 | 2.170 | 0.0002 | 0.105 | 0.7778 |
| 203757_s_at | CEACAM6 | carcinoembryonic antigen-related cell adhesion molecule 6 | 4680 | 4.13 | 138.1 | 988.3 | 2.530 | 0.0002 | 1.012 | 0.0025 |
| 227609_at | EPSTI1 | epithelial stromal interaction 1 (breast) | 94240 | 4.07 | 777.8 | 3444.3 | 2.079 | 0.0002 | 0.045 | 0.8913 |
| 207269_at | DEFA4 | defensin, alpha 4, corticostatin | 1669 | 3.99 | 440.8 | 2209.3 | 2.380 | 0.0003 | 0.784 | 0.0279 |
| 231455_at | FLJ42418 | FLJ42418 protein | 400941 | 3.98 | 16.1 | 93.0 | 1.967 | 0.0002 | −0.195 | 0.5637 |
| 219863_at | HERC5 | hect domain and RLD 5 | 51191 | 3.96 | 870.5 | 3782.4 | 2.054 | 0.0002 | 0.099 | 0.7441 |
| 200923_at | LGALS3BP | lectin, galactoside-binding, soluble, 3 binding protein ... | 100133842 /// 3959 | 3.88 | 303.5 | 1375.4 | 2.008 | 0.0003 | −0.012 | 0.9973 |
| 202145_at | LY6E | lymphocyte antigen 6 complex, locus E | 4061 | 3.78 | 295.2 | 1297.0 | 2.032 | 0.0002 | 0.104 | 0.7183 |
| 211657_at | CEACAM6 | carcinoembryonic antigen-related cell adhesion molecule 6 (non-specific cross reacting antigen) | 4680 | 3.72 | 119.7 | 760.5 | 2.325 | 0.0002 | 0.936 | 0.0034 |
| 202869_at | OAS1 | 2',5'-oligoadenylate synthetase 1, 40/46 kDa | 4938 | 3.57 | 533.3 | 1969.3 | 1.892 | 0.0002 | 0.016 | 0.9973 |
| 217502_at | IFIT2 | interferon-induced protein with tetratricopeptide repeats 2 | 3433 | 3.51 | 180.6 | 798.3 | 2.067 | 0.0002 | 0.320 | 0.3115 |
| 209369_at | ANXA3 | annexin A3 | 306 | 3.50 | 199.9 | 1023.4 | 2.318 | 0.0002 | 1.097 | 0.0034 |
| 209498_at | CEACAM1 | carcinoembryonic antigen-related cell adhesion molecule 1 (biliary glycoprotein) | 634 | 3.41 | 86.2 | 369.6 | 2.099 | 0.0002 | 0.739 | 0.0025 |
| 203936_s_at | MMP9 | matrix metallopeptidase 9 (gelatinase B, 92 kDa gelatinase) | 4318 | 3.39 | 185.8 | 999.3 | 2.308 | 0.0002 | 1.151 | 0.0025 |
| 226757_at | IFIT2 | interferon-induced protein with tetratricopeptide repeats 2 | 3433 | 3.33 | 2374.3 | 8287.7 | 1.835 | 0.0002 | 0.173 | 0.5410 |
| 205552_s_at | OAS1 | 2',5'-oligoadenylate synthetase 1, 40/46 kDa | 4938 | 3.32 | 322.5 | 1155.4 | 1.801 | 0.0002 | 0.094 | 0.7738 |
| 204972_at | OAS2 | 2',5'-oligoadenylate synthetase 2, 69/71 kDa | 4939 | 3.20 | 689.7 | 2410.2 | 1.711 | 0.0002 | 0.046 | 0.8637 |
| 204187_at | GMPR | guanosine monophosphate reductase | 2766 | 3.18 | 179.2 | 675.6 | 1.537 | 0.0002 | −0.195 | 0.4156 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 206133_at | XAF1 | XIAP associated factor 1 | 54739 | 3.17 | 830.4 | 2798.0 | 1.712 | 0.0002 | -0.026 | 0.9536 |
| 238439_at | ANKRD22 | ankyrin repeat domain 22 | 118932 | 3.12 | 56.5 | 201.0 | 1.802 | 0.0002 | 0.127 | 0.7549 |
| 201015_s_at | JUP | junction plakoglobin | 3728 | 3.11 | 117.5 | 388.0 | 1.727 | 0.0002 | 0.004 | 0.9017 |
| 219410_at | TMEM45A | transmembrane protein 45A | 55076 | 3.09 | 16.9 | 95.1 | 2.061 | 0.0002 | 0.781 | 0.0025 |
| 222154_s_at | LOC26010 | viral DNA polymerase-transactivated protein 6 | 26010 | 3.06 | 498.4 | 1700.3 | 1.684 | 0.0002 | 0.069 | 0.7915 |
| 224225_s_at | ETV7 | ets variant 7 | 51513 | 3.06 | 30.1 | 108.4 | 1.716 | 0.0002 | 0.144 | 0.5875 |
| 206025_s_at | TNFAIP6 | tumor necrosis factor, alpha-induced protein 6 | 7130 | 2.99 | 110.2 | 393.1 | 2.000 | 0.0002 | 0.754 | 0.0106 |
| 235276_at | EPSTI1 | Epithelial stromal interaction 1 (breast) | 94240 | 2.97 | 948.9 | 2947.6 | 1.588 | 0.0002 | 0.001 | 0.9973 |
| 208436_at | IRF7 | interferon regulatory factor 7 | 3665 | 2.87 | 384.0 | 1193.4 | 1.601 | 0.0002 | 0.034 | 0.8584 |
| 228617_at | XAF1 | XIAP associated factor 1 | 54739 | 2.87 | 1842.2 | 5575.4 | 1.526 | 0.0002 | -0.016 | 0.9972 |
| 236285_at | KLHDC7B | kelch domain containing 7B | 113730 | 2.87 | 222.4 | 733.7 | 1.544 | 0.0002 | -0.063 | 0.9027 |
| 205660_at | OASL | 2'-5'-oligoadenylate synthetase-like | 8638 | 2.79 | 198.4 | 614.9 | 1.664 | 0.0002 | 0.246 | 0.2650 |
| 205033_s_at | DEFA1 /// DEFA3 /// LOC728358 | defensin, alpha 1 /// defensin, alpha 3, neutrophil-specific /// defensin, alpha 1 | 1667 /// 1668 /// 728358 | 2.77 | 5368.5 | 13723.5 | 1.752 | 0.0012 | 0.570 | 0.0543 |
| 206515_at | CYP4F3 | cytochrome P450, family 4, subfamily F, polypeptide 3 | 4051 | 2.75 | 197.1 | 591.2 | 1.907 | 0.0006 | 0.978 | 0.0152 |
| 223220_x_at | PARP9 | poly (ADP-ribose) polymerase family, member 9 | 83666 | 2.75 | 852.6 | 2429.7 | 1.546 | 0.0002 | 0.082 | 0.6516 |
| 221748_s_at | TNS1 | tensin 1 | 7145 | 2.74 | 157.4 | 692.4 | 1.167 | 0.0024 | -0.292 | 0.4061 |
| 202430_s_at | PLSCR1 | phospholipid scramblase 1 | 5359 | 2.72 | 728.6 | 2005.0 | 1.554 | 0.0003 | 0.166 | 0.2419 |
| 210163_at | CXCL11 | chemokine (C—X—C motif) ligand 11 | 6373 | 2.71 | 8.9 | 34.9 | 1.330 | 0.0002 | -0.335 | 0.1473 |
| 230036_at | SAMD9L | sterile alpha motif domain containing 9-like | 219285 | 2.71 | 912.4 | 2554.3 | 1.476 | 0.0002 | 0.040 | 0.8553 |
| 204211_x_at | EIF2AK2 | eukaryotic translation initiation factor 2-alpha kinase 2 | 5610 | 2.70 | 207.7 | 583.0 | 1.438 | 0.0002 | 0.012 | 0.9511 |
| 219352_at | HERC6 | hect domain and RLD 6 | 55008 | 2.69 | 341.0 | 986.4 | 1.386 | 0.0002 | -0.119 | 0.5244 |
| 226103_at | NEXN | nexilin (F actin binding protein) | 91624 | 2.68 | 208.8 | 571.0 | 1.367 | 0.0002 | -0.141 | 0.5189 |
| 223599_at | TRIM6 | tripartite motif-containing 6 | 117854 | 2.67 | 31.1 | 103.6 | 1.718 | 0.0002 | 0.546 | 0.0034 |
| 204994_at | MX2 | myxovirus (influenza virus) resistance 2 (mouse) | 4600 | 2.65 | 1242.6 | 3443.9 | 1.469 | 0.0002 | 0.056 | 0.8173 |
| 211122_s_at | CXCL11 | chemokine (C—X—C motif) ligand 11 | 6373 | 2.64 | 14.3 | 55.8 | 1.311 | 0.0003 | -0.309 | 0.2033 |
| 1552309_a_at | NEXN | nexilin (F actin binding protein) | 91624 | 2.62 | 241.5 | 648.8 | 1.331 | 0.0002 | -0.131 | 0.4672 |
| 202446_s_at | PLSCR1 | phospholipid scramblase 1 | 5359 | 2.61 | 2283.9 | 6147.4 | 1.502 | 0.0002 | 0.145 | 0.2945 |
| 206553_at | OAS2 | 2'-5'-oligoadenylate synthetase 2, 69/71 kDa | 4939 | 2.56 | 70.8 | 191.8 | 1.419 | 0.0002 | 0.061 | 0.7810 |
| 266_s_at | CD24 | CD24 molecule | 100133941 | 2.53 | 357.7 | 1238.9 | 1.530 | 0.0002 | 0.466 | 0.0335 |
| 213294_at | EIF2AK2 | eukaryotic translation initiation factor 2-alpha kinase 2 | 5610 | 2.52 | 1076.3 | 2842.2 | 1.322 | 0.0002 | -0.044 | 0.8553 |
| 205557_at | BPI | bactericidal/permeability-increasing protein | 671 | 2.48 | 257.3 | 977.1 | 1.665 | 0.0003 | 0.746 | 0.0034 |
| 209395_at | CHI3L1 | chitinase 3-like 1 (cartilage glycoprotein-39) | 1116 | 2.48 | 187.5 | 522.0 | 1.837 | 0.0009 | 1.132 | 0.0025 |
| 216379_x_at | CD24 | CD24 molecule | 100133941 | 2.46 | 673.7 | 2203.1 | 1.487 | 0.0002 | 0.443 | 0.0442 |
| 243754_at | | | | 2.45 | 61.5 | 161.0 | 1.406 | 0.0002 | 0.124 | 0.3969 |
| 206851_at | RNASE3 | ribonuclease, RNase A family, 3 (eosinophil cationic protein) | 6037 | 2.43 | 114.7 | 438.9 | 1.556 | 0.0006 | 0.612 | 0.0140 |
| 209771_x_at | CD24 | CD24 molecule | 100133941 | 2.41 | 672.5 | 2150.0 | 1.459 | 0.0002 | 0.453 | 0.0334 |
| 219179_at | DACT1 | dapper, antagonist of beta-catenin, homolog 1 (Xenopus laevis) | 51339 | 2.41 | 68.4 | 177.1 | 1.064 | 0.0012 | -0.218 | 0.3832 |
| 219209_at | IFIH1 | interferon induced with helicase C domain 1 | 64135 | 2.39 | 731.3 | 1749.3 | 1.283 | 0.0002 | -0.003 | 0.9973 |
| 208650_s_at | CD24 | CD24 molecule | 100133941 | 2.39 | 82.0 | 293.8 | 1.426 | 0.0002 | 0.423 | 0.0584 |
| 239979_at | | | | 2.39 | 116.6 | 301.3 | 1.428 | 0.0002 | 0.154 | 0.5244 |
| 204858_s_at | TYMP | thymidine phosphorylase | 1890 | 2.38 | 694.3 | 1673.6 | 1.336 | 0.0002 | -0.012 | 0.9575 |
| 227807_at | PARP9 | poly (ADP-ribose) polymerase family, member 9 | 83666 | 2.38 | 356.2 | 894.9 | 1.291 | 0.0002 | 0.047 | 0.8584 |
| 208651_x_at | CD24 | CD24 molecule | 100133941 | 2.34 | 95.3 | 309.0 | 1.421 | 0.0002 | 0.473 | 0.0301 |
| 206371_at | FOLR3 | folate receptor 3 (gamma) | 2352 | 2.30 | 107.2 | 407.5 | 1.547 | 0.0003 | 0.654 | 0.0025 |
| 210797_s_at | OASL | 2'-5'-oligoadenylate synthetase-like | 8638 | 2.30 | 192.7 | 469.9 | 1.377 | 0.0002 | 0.236 | 0.2650 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 218943_s_at | DDX58 | DEAD (Asp-Glu-Ala-Asp) box polypeptide 58 | 23586 | 2.30 | 642.5 | 1495.7 | 1.278 | 0.0002 | 0.093 | 0.7353 |
| 218986_s_at | DDX60 | DEAD (Asp-Glu-Ala-Asp) box polypeptide 60 | 55601 | 2.29 | 906.9 | 2173.1 | 1.149 | 0.0002 | −0.062 | 0.8264 |
| 235643_at | SAMD9L | sterile alpha motif domain containing 9-like | 219285 | 2.28 | 132.4 | 327.8 | 1.336 | 0.0002 | 0.055 | 0.8972 |
| 206698_at | XK | X-linked Kx blood group (McLeod syndrome) | 7504 | 2.26 | 118.0 | 438.5 | 1.007 | 0.0326 | 0.050 | 0.9973 |
| AFFX-HUMISGF3A/M97935_MA_at | STAT1 | signal transducer and activator of transcription 1, 91 kDa | 6772 | 2.25 | 378.8 | 868.8 | 1.168 | 0.0002 | −0.043 | 0.8553 |
| 209969_s_at | STAT1 | signal transducer and activator of transcription 1, 91 kDa | 6772 | 2.25 | 1250.4 | 2874.8 | 1.180 | 0.0002 | −0.068 | 0.7183 |
| 219672_at | ERAF | erythroid associated factor | 51327 | 2.25 | 69.8 | 408.3 | 0.958 | 0.0439 | −0.021 | 0.9536 |
| 205003_at | DOCK4 | dedicator of cytokinesis 4 | 9732 | 2.24 | 52.2 | 125.4 | 1.372 | 0.0002 | 0.394 | 0.1192 |
| 219607_s_at | MS4A4A | membrane-spanning 4-domains, subfamily A, member 4 | 51338 | 2.23 | 298.5 | 694.1 | 1.232 | 0.0002 | 0.100 | 0.8185 |
| AFFX-HUMISGF3A/M97935_MB_at | STAT1 | signal transducer and activator of transcription 1, 91 kDa | 6772 | 2.22 | 276.7 | 619.6 | 1.096 | 0.0002 | −0.079 | 0.7448 |
| 203949_at | MPO | myeloperoxidase | 4353 | 2.22 | 187.5 | 637.6 | 1.433 | 0.0048 | 0.642 | 0.0465 |
| 221345_at | FFAR2 | free fatty acid receptor 2 | 2867 | 2.22 | 64.2 | 181.7 | 1.449 | 0.0003 | 0.542 | 0.0948 |
| 211372_s_at | IL1R2 | interleukin 1 receptor, type II | 7850 | 2.20 | 83.0 | 323.7 | 1.728 | 0.0006 | 1.164 | 0.0034 |
| 243271_at | | | | 2.19 | 347.6 | 795.2 | 1.205 | 0.0006 | 0.047 | 0.8972 |
| 209417_s_at | IFI35 | interferon-induced protein 35 | 3430 | 2.18 | 587.1 | 1360.4 | 1.201 | 0.0002 | −0.001 | 0.9973 |
| 203596_s_at | IFIT5 | interferon-induced protein with tetratricopeptide repeats 5 | 24138 | 2.16 | 532.4 | 1161.4 | 1.172 | 0.0002 | 0.102 | 0.5238 |
| 205513_at | TCN1 | transcobalamin I (vitamin B12 binding protein, R binder family) | 6947 | 2.16 | 473.3 | 1236.8 | 1.438 | 0.0003 | 0.716 | 0.0025 |
| 226603_at | SAMD9L | sterile alpha motif domain containing 9-like | 219285 | 2.15 | 1585.7 | 3453.4 | 1.141 | 0.0002 | 0.009 | 0.9941 |
| 237597_at | | | | 2.15 | 24.7 | 66.2 | 1.086 | 0.0006 | 0.027 | 0.9972 |
| 203595_s_at | IFIT5 | interferon-induced protein with tetratricopeptide repeats 5 | 24138 | 2.13 | 798.8 | 1794.7 | 1.202 | 0.0002 | 0.169 | 0.3020 |
| 206584_at | LY96 | lymphocyte antigen 96 | 23643 | 2.13 | 897.7 | 1704.5 | 1.226 | 0.0002 | 0.214 | 0.3060 |
| 240336_at | HBM | hemoglobin, mu | 3042 | 2.12 | 114.8 | 479.8 | 0.937 | 0.0374 | 0.123 | 0.8584 |
| 217933_s_at | LAP3 | leucine aminopeptidase 3 | 51056 | 2.10 | 2372.6 | 5113.5 | 1.104 | 0.0002 | −0.016 | 0.8972 |
| 212657_s_at | IL1RN | interleukin 1 receptor antagonist | 3557 | 2.09 | 1171.9 | 2512.4 | 1.267 | 0.0002 | 0.308 | 0.1908 |
| 1559585_at | DDX6OL | DEAD (Asp-Glu-Ala-Asp) box polypeptide 60-like | 91351 | 2.07 | 73.7 | 169.2 | 1.218 | 0.0002 | 0.333 | 0.1181 |
| 202688_at | TNFSF10 | tumor necrosis factor (ligand) superfamily, member 10 | 8743 | 2.02 | 3062.3 | 5883.6 | 1.071 | 0.0002 | 0.040 | 0.8948 |
| 212845_at | SAMD4A | sterile alpha motif domain containing 4A | 23034 | 2.02 | 229.6 | 507.4 | 0.986 | 0.0003 | −0.135 | 0.5490 |
| 231078_at | | | | 2.01 | 355.4 | 793.0 | 0.863 | 0.0186 | 0.180 | 0.7781 |
| 202687_s_at | TNFSF10 | tumor necrosis factor (ligand) superfamily, member 10 | 8743 | 2.00 | 1331.4 | 2506.5 | 1.075 | 0.0002 | 0.036 | 0.9369 |
| 206655_s_at | GP1BB /// SEPT5 | glycoprotein 1b (platelet), beta polypeptide /// septin 5 | 2812 /// 5413 | 2.00 | 156.0 | 411.7 | 0.986 | 0.0188 | 0.097 | 0.9042 |
| 208886_at | H1F0 | H1 histone family, member 0 | 3005 | 1.99 | 235.7 | 474.0 | 1.080 | 0.0002 | 0.163 | 0.3271 |
| 209930_s_at | NFE2 | nuclear factor (erythroid-derived 2), 45 kDa | 4778 | 1.99 | 313.0 | 599.0 | 1.165 | 0.0002 | 0.322 | 0.0930 |
| 222793_at | DDX58 | DEAD (Asp-Glu-Ala-Asp) box polypeptide 58 | 23586 | 1.99 | 393.3 | 762.0 | 1.042 | 0.0002 | 0.058 | 0.8903 |
| 233591_at | | | | 1.99 | 11.5 | 31.2 | 1.294 | 0.0002 | 0.662 | 0.0063 |
| 218332_at | BEX1 | brain expressed, X-linked 1 | 55859 | 1.98 | 81.0 | 233.6 | 1.232 | 0.0002 | 0.477 | 0.0063 |
| 224009_x_at | DHRS9 | dehydrogenase/reductase (SDR family) member 9 | 10170 | 1.98 | 128.3 | 273.5 | 1.199 | 0.0002 | 0.468 | 0.0176 |
| 203434_s_at | MME | membrane metallo-endopeptidase | 4311 | 1.97 | 49.3 | 129.6 | 1.232 | 0.0175 | 0.642 | 0.1357 |
| 222528_s_at | SLC25A37 | solute carrier family 25, member 37 | 51312 | 1.97 | 45.4 | 137.5 | 1.064 | 0.0062 | 0.406 | 0.2878 |
| 212203_x_at | IFITM3 | interferon induced transmembrane protein 3 (1-8U) | 10410 | 1.96 | 3964.6 | 8024.2 | 1.068 | 0.0002 | 0.113 | 0.4035 |
| 202708_s_at | HIST2H2BE | histone cluster 2, H2be | 8349 | 1.92 | 578.8 | 1263.6 | 0.991 | 0.0019 | 0.147 | 0.7998 |
| 204430_s_at | SLC2A5 | solute carrier family 2 (glucose/fructose), member 5 | 6518 | 1.92 | 93.4 | 244.9 | 1.142 | 0.0021 | 0.450 | 0.0422 |
| 205844_at | VNN1 | vanin 1 | 8876 | 1.92 | 614.2 | 1319.8 | 1.199 | 0.0006 | 0.495 | 0.0248 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 219691_at | SAMD9 | sterile alpha motif domain containing 9 | 54809 | 1.92 | 161.1 | 319.5 | 0.949 | 0.0002 | 0.040 | 0.8584 |
| 205241_at | SCO2 | SCO cytochrome oxidase deficient homolog 2 (yeast) | 9997 | 1.91 | 1823.5 | 3641.8 | 1.056 | 0.0002 | 0.080 | 0.8285 |
| 223952_x_at | DHRS9 | dehydrogenase/reductase (SDR family) member 9 | 10170 | 1.91 | 137.3 | 285.2 | 1.145 | 0.0002 | 0.448 | 0.0125 |
| 231769_at | FBXO6 | F-box protein 6 | 26270 | 1.91 | 365.9 | 729.7 | 1.042 | 0.0002 | 0.109 | 0.4164 |
| 1552639_at | KLHDC7B | kelch domain containing 7B | 113730 | 1.91 | 82.1 | 175.6 | 1.017 | 0.0002 | −0.004 | 0.9994 |
| 225782_at | MSRB3 | methionine sulfoxide reductase B3 | 253827 | 1.90 | 146.4 | 329.8 | 1.043 | 0.0006 | 0.357 | 0.1359 |
| 201601_x_at | IFITM1 | interferon induced transmembrane protein 1 (9-27) | 8519 | 1.89 | 4149.9 | 7925.0 | 0.941 | 0.0002 | 0.023 | 0.9269 |
| 215617_at | LOC26010 | viral DNA polymerase-transactivated protein 6 | 26010 | 1.89 | 12.1 | 25.0 | 1.013 | 0.0002 | 0.046 | 0.7988 |
| 231192_at | | | | 1.88 | 14.4 | 30.2 | 0.730 | 0.0006 | −0.324 | 0.0359 |
| 238327_at | ODF3B | outer dense fiber of sperm tails 3B | 440836 | 1.88 | 146.5 | 271.9 | 1.043 | 0.0002 | 0.117 | 0.5994 |
| 208792_s_at | CLU | clusterin | 1191 | 1.87 | 460.9 | 1103.4 | 0.871 | 0.0275 | 0.121 | 0.8551 |
| 239196_at | ANKRD22 | ankyrin repeat domain 22 | 118932 | 1.87 | 58.4 | 121.2 | 1.033 | 0.0002 | 0.124 | 0.5494 |
| 202589_at | TYMS | thymidylate synthetase | 7298 | 1.86 | 291.7 | 633.6 | 1.113 | 0.0002 | 0.270 | 0.1644 |
| 219799_s_at | DHRS9 | dehydrogenase/reductase (SDR family) member 9 | 10170 | 1.86 | 480.0 | 942.2 | 1.104 | 0.0002 | 0.428 | 0.0125 |
| 239988_at | | | | 1.86 | 109.2 | 207.7 | 0.900 | 0.0002 | −0.001 | 0.9972 |
| 204798_at | MYB | v-myb myeloblastosis viral oncogene homolog (avian) | 4602 | 1.85 | 264.5 | 517.9 | 0.992 | 0.0002 | 0.246 | 0.0638 |
| 219062_s_at | ZCCHC2 | zinc finger, CCHC domain containing 2 | 54877 | 1.84 | 644.6 | 1230.1 | 0.982 | 0.0002 | 0.120 | 0.3536 |
| 219684_at | RTP4 | receptor (chemosensory) transporter protein 4 | 64108 | 1.84 | 380.2 | 698.2 | 0.924 | 0.0002 | 0.017 | 0.9426 |
| 222816_s_at | ZCCHC2 | zinc finger, CCHC domain containing 2 | 54877 | 1.84 | 539.9 | 1032.6 | 1.047 | 0.0003 | 0.232 | 0.0886 |
| AFFX-HUMISGF3A/ M97935_3_at | STAT1 | signal transducer and activator of transcription 1, 91 kDa | 6772 | 1.83 | 3958.9 | 7262.2 | 0.835 | 0.0002 | −0.086 | 0.3773 |
| 217497_s_at | TYMP | thymidine phosphorylase | 1890 | 1.83 | 250.6 | 480.5 | 1.085 | 0.0002 | 0.207 | 0.3249 |
| 223770_x_at | CISH | cytokine inducible SH2-containing protein | 1154 | 1.83 | 660.9 | 1162.5 | 0.815 | 0.0009 | −0.144 | 0.6456 |
| 223767_at | GPR84 | G protein-coupled receptor 84 | 53831 | 1.83 | 71.6 | 156.6 | 1.181 | 0.0003 | 0.537 | 0.0152 |
| 228152_s_at | DDX60L | DEAD (Asp-Glu-Ala-Asp) box polypeptide 60-like | 91351 | 1.83 | 2160.1 | 3970.6 | 0.971 | 0.0002 | 0.143 | 0.2309 |
| 209761_s_at | SP110 | SP110 nuclear body protein | 3431 | 1.82 | 302.9 | 564.5 | 0.931 | 0.0002 | 0.073 | 0.6772 |
| 214329_x_at | TNFSF10 | tumor necrosis factor (ligand) superfamily, member 10 | 8743 | 1.82 | 1716.5 | 2817.4 | 0.914 | 0.0002 | 0.016 | 0.9575 |
| 214472_at | HIST1H2AD /// HIST1H3D | histone cluster 1, H2ad /// histone cluster 1, H3d | 3013 /// 8351 | 1.82 | 35.7 | 72.0 | 1.109 | 0.0002 | 0.530 | 0.0084 |
| 228607_at | OAS2 | 2′-5′-oligoadenylate synthetase 2, 69/71 kDa | 4939 | 1.82 | 385.7 | 723.3 | 0.913 | 0.0002 | 0.038 | 0.8972 |
| 210772_at | FPR2 | formyl peptide receptor 2 | 2358 | 1.81 | 289.9 | 536.2 | 1.103 | 0.0002 | 0.451 | 0.0415 |
| 218585_s_at | DTL | denticleless homolog (*Drosophila*) | 51514 | 1.81 | 69.5 | 148.1 | 1.052 | 0.0003 | 0.245 | 0.1978 |
| 219295_s_at | PCOLCE2 | procollagen C-endopeptidase enhancer 2 | 26577 | 1.81 | 20.7 | 64.2 | 1.130 | 0.0012 | 0.526 | 0.0272 |
| 220059_at | STAP1 | signal transducing adaptor family member 1 | 26228 | 1.81 | 378.7 | 720.4 | 0.747 | 0.0006 | −0.282 | 0.1036 |
| 201649_at | UBE2L6 | ubiquitin-conjugating enzyme E2L 6 | 9246 | 1.80 | 1856.7 | 3402.4 | 0.903 | 0.0002 | 0.025 | 0.8960 |
| 208791_at | CLU | clusterin | 1191 | 1.80 | 283.4 | 652.8 | 0.782 | 0.0372 | 0.067 | 0.9284 |
| 230422_at | FPR3 | formyl peptide receptor 3 | 2359 | 1.80 | 51.5 | 104.2 | 0.857 | 0.0024 | −0.176 | 0.3726 |
| 210119_at | KCNJ15 | potassium inwardly-rectifying channel, subfamily J, member 15 | 3772 | 1.79 | 259.8 | 548.8 | 1.271 | 0.0021 | 0.828 | 0.0034 |
| 203021_at | SLPI | secretory leukocyte peptidase inhibitor | 6590 | 1.78 | 151.1 | 332.0 | 1.140 | 0.0003 | 0.590 | 0.0025 |
| 212805_at | PRUNE2 | prune homolog 2 (*Drosophila*) | 158471 | 1.78 | 56.1 | 136.5 | 1.008 | 0.0003 | 0.339 | 0.0235 |
| 205306_x_at | KMO | kynurenine 3-monooxygenase (kynurenine 3-hydroxylase) | 8564 | 1.77 | 289.7 | 533.7 | 0.806 | 0.0002 | −0.137 | 0.4902 |
| 218974_at | SOBP | sine oculis binding protein homolog (*Drosophila*) | 55084 | 1.77 | 84.2 | 174.6 | 0.760 | 0.0006 | −0.187 | 0.4840 |
| 220945_x_at | MANSC1 | MANSC domain containing 1 | 54682 | 1.77 | 153.7 | 296.0 | 1.150 | 0.0009 | 0.798 | 0.0084 |
| 221541_at | CRISPLD2 | cysteine-rich secretory protein LCCL domain containing 2 | 83716 | 1.77 | 758.2 | 1401.5 | 1.054 | 0.0002 | 0.428 | 0.0207 |
| 222608_s_at | ANLN | anillin, actin binding protein | 54443 | 1.77 | 15.8 | 43.3 | 1.093 | 0.0012 | 0.463 | 0.0309 |
| 1554343_a_at | STAP1 | signal transducing adaptor family member 1 | 26228 | 1.77 | 157.5 | 298.5 | 0.724 | 0.0014 | −0.258 | 0.1703 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 201641_at | BST2 | bone marrow stromal cell antigen 2 | 684 | 1.76 | 853.3 | 1525.6 | 0.856 | 0.0002 | -0.020 | 0.8972 |
| 211889_x_at | CEACAM1 | carcinoembryonic antigen-related cell adhesion molecule 1 (biliary glycoprotein) | 634 | 1.76 | 42.5 | 82.1 | 1.029 | 0.0002 | 0.472 | 0.0025 |
| 211138_at | KMO | kynurenine 3-monooxygenase (kynurenine 3-hydroxylase) | 8564 | 1.75 | 329.3 | 599.3 | 0.806 | 0.0002 | -0.123 | 0.5579 |
| 221223_x_at | CISH | cytokine inducible SH2-containing protein | 1154 | 1.75 | 647.0 | 1086.6 | 0.757 | 0.0003 | -0.119 | 0.7013 |
| 204560_at | FKBP5 | FK506 binding protein 5 | 2289 | 1.74 | 98.4 | 220.2 | 0.978 | 0.0002 | 0.274 | 0.2309 |
| 224856_at | FKBP5 | FK506 binding protein 5 | 2289 | 1.74 | 1007.9 | 2151.7 | 0.928 | 0.0003 | 0.260 | 0.2886 |
| 200887_s_at | STAT1 | signal transducer and activator of transcription 1, 91 kDa | 6772 | 1.73 | 5386.4 | 9329.8 | 0.764 | 0.0002 | -0.071 | 0.3832 |
| 206157_at | PTX3 | pentraxin-related gene, rapidly induced by IL-1 beta | 5806 | 1.73 | 223.1 | 388.6 | 1.121 | 0.0014 | 0.608 | 0.0084 |
| 220615_s_at | FAR2 | fatty acyl CoA reductase 2 | 55711 | 1.73 | 213.3 | 401.1 | 1.071 | 0.0002 | 0.573 | 0.0025 |
| 222067_x_at | HIST1H2BD | histone cluster 1, H2bd | 3017 | 1.73 | 96.9 | 173.7 | 0.863 | 0.0002 | 0.181 | 0.2620 |
| 33304_at | ISG20 | interferon stimulated exonuclease gene 20 kDa | 3669 | 1.73 | 1982.5 | 3471.1 | 0.792 | 0.0002 | -0.053 | 0.7810 |
| 223939_at | SUCNR1 | succinate receptor 1 | 56670 | 1.72 | 33.1 | 68.4 | 0.937 | 0.0014 | 0.401 | 0.0422 |
| 205118_at | FPR1 | formyl peptide receptor 1 | 2357 | 1.71 | 105.4 | 200.1 | 1.135 | 0.0002 | 0.609 | 0.0248 |
| 212099_at | RHOB | ras homolog gene family, member B | 388 | 1.71 | 326.7 | 651.8 | 0.994 | 0.0002 | 0.219 | 0.4389 |
| 219918_s_at | ASPM | asp (abnormal spindle) homolog, microcephaly associated (Drosophila) | 259266 | 1.71 | 41.3 | 79.1 | 0.989 | 0.0006 | 0.287 | 0.1584 |
| 225056_at | SIPA1L2 | signal-induced proliferation-associated 1 like 2 | 57568 | 1.71 | 167.4 | 303.3 | 1.073 | 0.0002 | 0.519 | 0.0025 |
| 210001_s_at | SOCS1 | suppressor of cytokine signaling 1 | 8651 | 1.70 | 99.4 | 195.8 | 0.860 | 0.0002 | 0.087 | 0.7810 |
| 211883_x_at | CEACAM1 | carcinoembryonic antigen-related cell adhesion molecule 1 (biliary glycoprotein) | 634 | 1.70 | 44.5 | 86.8 | 1.055 | 0.0002 | 0.594 | 0.0025 |
| 218543_s_at | PARP12 | poly (ADP-ribose) polymerase family, member 12 | 64761 | 1.70 | 1736.3 | 3050.5 | 0.791 | 0.0002 | -0.042 | 0.8480 |
| 225415_at | DTX3L | deltex 3-like (Drosophila) | 151636 | 1.70 | 1486.0 | 2518.3 | 0.785 | 0.0002 | -0.003 | 0.9973 |
| 239033_at | | | | 1.70 | 116.9 | 204.6 | 0.886 | 0.0002 | 0.179 | 0.1277 |
| 203820_s_at | IGF2BP3 | insulin-like growth factor 2 mRNA binding protein 3 | 10643 | 1.69 | 179.0 | 318.1 | 0.694 | 0.0052 | -0.012 | 0.9302 |
| 224701_at | PARP14 | poly (ADP-ribose) polymerase family, member 14 | 54625 | 1.69 | 674.3 | 1169.2 | 0.865 | 0.0002 | 0.094 | 0.5702 |
| 201291_s_at | TOP2A | topoisomerase (DNA) II alpha 170 kDa | 7153 | 1.68 | 84.1 | 163.3 | 0.984 | 0.0012 | 0.345 | 0.0793 |
| 202284_s_at | CDKN1A | cyclin-dependent kinase inhibitor 1A (p21, Cip1) | 1026 | 1.68 | 609.2 | 988.9 | 0.765 | 0.0006 | -0.097 | 0.6341 |
| 210218_s_at | SP100 | SP100 nuclear antigen | 6672 | 1.68 | 240.9 | 398.2 | 0.752 | 0.0002 | 0.049 | 0.7595 |
| 1554624_a_at | SIRPB1 | signal-regulatory protein beta 1 | 10326 | 1.68 | 228.4 | 394.0 | 0.955 | 0.0002 | 0.346 | 0.0279 |
| 209762_x_at | SP110 | SP110 nuclear body protein | 3431 | 1.67 | 1272.0 | 2149.1 | 0.748 | 0.0002 | 0.045 | 0.7810 |
| 221680_s_at | ETV7 | ets variant 7 | 51513 | 1.67 | 65.4 | 110.2 | 0.787 | 0.0002 | 0.008 | 0.9375 |
| 223502_s_at | TNFSF13B | tumor necrosis factor (ligand) superfamily, member 13b | 10673 | 1.67 | 2637.7 | 4199.0 | 0.822 | 0.0002 | 0.137 | 0.4391 |
| 224707_at | C5orf32 | chromosome 5 open reading frame 32 | 84418 | 1.67 | 273.9 | 491.3 | 0.979 | 0.0002 | 0.499 | 0.0025 |
| 225655_at | UHRF1 | ubiquitin-like with PHD and ring finger domains 1 | 29128 | 1.67 | 45.0 | 86.9 | 0.965 | 0.0003 | 0.284 | 0.0829 |
| 238513_at | PRRG4 | Proline rich Gla (G-carboxyglutamic acid) 4 (transmembrane) | 79056 | 1.67 | 522.3 | 847.7 | 0.941 | 0.0002 | 0.439 | 0.0176 |
| 203535_at | S100A9 | S100 calcium binding protein A9 | 6280 | 1.66 | 7775.8 | 13005.9 | 0.960 | 0.0002 | 0.344 | 0.0034 |
| 202912_at | ADM | adrenomedullin | 133 | 1.65 | 1216.3 | 1896.3 | 1.010 | 0.0021 | 0.542 | 0.0192 |
| 210014_at | OLR1 | oxidized low density lipoprotein (lectin-like) receptor 1 | 4973 | 1.65 | 13.9 | 35.2 | 0.987 | 0.0038 | 0.570 | 0.0192 |
| 220528_at | VNN3 | vanin 3 | 55350 | 1.65 | 169.7 | 346.2 | 1.092 | 0.0077 | 0.730 | 0.0106 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 204961_s_at | LOC648998 /// NCF1 /// NCF1B /// NCF1C | similar to Neutrophil cytosol factor 1 (NCF-1), pseudogene | 648998 /// 653361 /// 654816 /// 654817 | 1.64 | 937.3 | 1524.6 | 0.887 | 0.0002 | 0.242 | 0.0755 |
| 1558549_s_at | VNN1 | vanin 1 | 8876 | 1.64 | 124.5 | 237.6 | 0.931 | 0.0014 | 0.433 | 0.0235 |
| 202252_at | RAB13 | RAB13, member RAS oncogene family | 5872 | 1.63 | 434.9 | 792.3 | 0.940 | 0.0003 | 0.448 | 0.0025 |
| 226152_at | TTC7B | tetratricopeptide repeat domain 7B | 145567 | 1.63 | 105.1 | 198.2 | 0.678 | 0.0303 | 0.108 | 0.8553 |
| 229893_at | FRMD3 | FERM domain containing 3 | 257019 | 1.63 | 167.8 | 274.3 | 0.671 | 0.0014 | 0.088 | 0.8135 |
| 231274_s_at | | | | 1.63 | 1449.4 | 2790.2 | 0.794 | 0.0237 | 0.413 | 0.1978 |
| 239108_at | FAR2 | Fatty acyl CoA reductase 2 | 55711 | 1.63 | 330.4 | 561.3 | 0.900 | 0.0002 | 0.415 | 0.0025 |
| 203355_s_at | PSD3 | pleckstrin and Sec7 domain containing 3 | 23362 | 1.62 | 36.9 | 65.7 | 0.561 | 0.0084 | -0.167 | 0.3366 |
| 203127_s_at | SPTLC2 | serine palmitoyltransferase, long chain base subunit 2 | 9517 | 1.61 | 681.2 | 1159.2 | 0.816 | 0.0002 | 0.164 | 0.1646 |
| 205931_s_at | CREB5 | cAMP responsive element binding protein 5 | 9586 | 1.61 | 151.5 | 265.2 | 1.073 | 0.0002 | 0.668 | 0.0025 |
| 216020_at | IFIH1 | Interferon induced with helicase C domain 1 | 64135 | 1.61 | 48.7 | 81.6 | 0.695 | 0.0009 | 0.058 | 0.8913 |
| 228531_at | SAMD9 | sterile alpha motif domain containing 9 | 54809 | 1.61 | 2238.0 | 3615.6 | 0.683 | 0.0002 | 0.003 | 0.9973 |
| 205098_at | CCR1 | chemokine (C—C motif) receptor 1 | 1230 | 1.60 | 2537.8 | 3772.3 | 0.848 | 0.0002 | 0.215 | 0.2152 |
| 205568_at | AQP9 | aquaporin 9 | 366 | 1.60 | 1315.7 | 2204.5 | 0.951 | 0.0009 | 0.549 | 0.0106 |
| 214022_at | IFITM1 | interferon induced transmembrane protein 1 (9-27) | 8519 | 1.60 | 6058.5 | 9686.7 | 0.706 | 0.0002 | 0.020 | 0.8972 |
| 219990_at | E2F8 | E2F transcription factor 8 | 79733 | 1.60 | 21.1 | 42.9 | 0.851 | 0.0033 | 0.305 | 0.0791 |
| 225095_at | SPTLC2 | Serine palmitoyltransferase, long chain base subunit 2 | 9517 | 1.60 | 443.9 | 728.8 | 0.780 | 0.0002 | 0.141 | 0.2544 |
| 228648_at | LRG1 | leucine-rich alpha-2-glycoprotein 1 | 116844 | 1.60 | 156.6 | 283.9 | 1.020 | 0.0012 | 0.720 | 0.0025 |
| 200678_x_at | GRN | granulin | 2896 | 1.59 | 4741.7 | 7605.6 | 0.817 | 0.0002 | 0.181 | 0.1223 |
| 205119_s_at | FPR1 | formyl peptide receptor 1 | 2357 | 1.59 | 4865.9 | 7350.1 | 0.863 | 0.0002 | 0.308 | 0.0778 |
| 205896_at | SLC22A4 | solute carrier family 22 (organic cation/ergothioneine transporter), member 4 | 6583 | 1.59 | 189.4 | 317.1 | 0.927 | 0.0014 | 0.561 | 0.0084 |
| 210705_s_at | TRIM5 | tripartite motif-containing 5 | 85363 | 1.59 | 399.8 | 649.7 | 0.687 | 0.0002 | 0.002 | 0.9575 |
| 213716_at | SECTM1 | secreted and transmembrane 1 | 6398 | 1.59 | 408.5 | 651.0 | 0.768 | 0.0002 | 0.114 | 0.5991 |
| 216041_x_at | GRN | granulin | 2896 | 1.59 | 4732.8 | 7620.2 | 0.825 | 0.0002 | 0.188 | 0.1161 |
| 216202_s_at | SPTLC2 | serine palmitoyltransferase, long chain base subunit 2 | 9517 | 1.59 | 197.3 | 337.7 | 0.804 | 0.0002 | 0.163 | 0.2807 |
| 219403_s_at | HPSE | heparanase | 10855 | 1.59 | 409.1 | 660.0 | 0.775 | 0.0002 | 0.074 | 0.8675 |
| 220146_at | TLR7 | toll-like receptor 7 | 51284 | 1.59 | 434.5 | 685.1 | 0.685 | 0.0026 | -0.045 | 0.8913 |
| 1558011_at | | | | 1.59 | 32.9 | 56.2 | 0.956 | 0.0002 | 0.443 | 0.0025 |
| 201315_x_at | IFITM2 | interferon induced transmembrane protein 2 (1-8D) | 10581 | 1.58 | 7660.0 | 12113.0 | 0.746 | 0.0002 | 0.127 | 0.2338 |
| 208012_x_at | SP110 | SP110 nuclear body protein | 3431 | 1.58 | 1621.6 | 2587.3 | 0.670 | 0.0002 | 0.045 | 0.7810 |
| 220000_at | SIGLEC5 | sialic acid binding Ig-like lectin 5 | 8778 | 1.58 | 168.7 | 290.3 | 0.870 | 0.0002 | 0.405 | 0.0034 |
| 233829_at | OR52K3P | olfactory receptor, family 52, subfamily K, member 3 pseudogene | 390035 | 1.58 | 220.1 | 346.7 | 0.891 | 0.0002 | 0.344 | 0.0449 |
| 201161_s_at | CSDA | cold shock domain protein A | 8531 | 1.57 | 941.1 | 1756.4 | 0.633 | 0.0029 | 0.077 | 0.8584 |
| 208392_x_at | SP110 | SP110 nuclear body protein | 3431 | 1.57 | 703.9 | 1111.6 | 0.695 | 0.0002 | 0.038 | 0.8135 |
| 210423_s_at | SLC11A1 | solute carrier family 11 (proton-coupled divalent metal ion transporters), member 1 | 6556 | 1.57 | 487.2 | 800.5 | 0.867 | 0.0002 | 0.318 | 0.0376 |
| 219298_at | ECHDC3 | enoyl Coenzyme A hydratase domain containing 3 | 79746 | 1.57 | 78.4 | 132.9 | 0.837 | 0.0002 | 0.299 | 0.0925 |
| 220005_at | P2RY13 | purinergic receptor P2Y, G-protein coupled, 13 | 53829 | 1.57 | 1408.3 | 1986.5 | 0.800 | 0.0002 | 0.297 | 0.1036 |
| 225869_s_at | UNC93B1 | unc-93 homolog B1 (C. elegans) | 81622 | 1.57 | 128.1 | 206.7 | 0.720 | 0.0002 | 0.117 | 0.4360 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 239205_s_at | CR1 /// CR1L | complement component (3b/4b) receptor 1 (Knops blood group) /// complement component (3b/4b) receptor 1-like | 1378 /// 1379 | 1.57 | 115.2 | 194.9 | 0.679 | 0.0012 | 0.107 | 0.7898 |
| 202974_at | MPP1 | membrane protein, palmitoylated 1, 55 kDa | 4354 | 1.56 | 1249.9 | 2112.4 | 0.589 | 0.0017 | 0.031 | 0.9973 |
| 204924_at | TLR2 | toll-like receptor 2 | 7097 | 1.56 | 2764.3 | 4247.6 | 0.841 | 0.0002 | 0.310 | 0.0623 |
| 209129_at | TRIP6 | thyroid hormone receptor interactor 6 | 7205 | 1.56 | 135.9 | 212.3 | 0.660 | 0.0002 | 0.011 | 0.8972 |
| 223553_s_at | DOK3 | docking protein 3 | 79930 | 1.56 | 752.2 | 1169.4 | 0.837 | 0.0002 | 0.329 | 0.0034 |
| 212185_x_at | MT2A | metallothionein 2A | 4502 | 1.55 | 890.6 | 1423.5 | 0.675 | 0.0002 | 0.017 | 0.9511 |
| 215043_s_at | LOC653188 /// SMA4 /// SMA5 | glucuronidase, beta pseudogene /// glucuronidase, beta pseudogene /// glucuronidase, beta pseudogene | 11039 /// 11042 /// 653188 | 1.55 | 141.3 | 241.7 | 0.941 | 0.0002 | 0.341 | 0.0272 |
| 218231_at | NAGK | N-acetylglucosamine kinase | 55577 | 1.55 | 2318.6 | 3515.9 | 0.697 | 0.0002 | 0.040 | 0.8972 |
| 224414_s_at | CARD6 | caspase recruitment domain family, member 6 | 84674 | 1.55 | 839.8 | 1262.7 | 0.753 | 0.0002 | 0.221 | 0.0580 |
| 224840_at | FKBP5 | FK506 binding protein 5 | 2289 | 1.55 | 4783.7 | 8195.6 | 0.714 | 0.0002 | 0.179 | 0.3121 |
| 232080_at | HECW2 | HECT, C2 and WW domain containing E3 ubiquitin protein ligase 2 | 57520 | 1.55 | 76.6 | 127.7 | 0.870 | 0.0003 | 0.459 | 0.0063 |
| 1556643_at | LOC100128718 | Hypothetical protein LOC100128718 | 100128718 | 1.55 | 362.2 | 567.6 | 0.619 | 0.0002 | -0.030 | 0.7998 |
| 1559034_at | SIRPB2 | signal-regulatory protein beta 2 | 284759 | 1.55 | 160.4 | 251.9 | 0.819 | 0.0003 | 0.256 | 0.1158 |
| 1561615_s_at | SLC8A1 | solute carrier family 8 (sodium/calcium exchanger), member 1 | 6546 | 1.55 | 55.5 | 92.9 | 0.843 | 0.0002 | 0.249 | 0.3143 |
| 202007_at | NID1 | nidogen 1 | 4811 | 1.54 | 232.3 | 342.0 | 0.536 | 0.0241 | -0.240 | 0.2425 |
| 202201_at | BLVRB | biliverdin reductase B (flavin reductase (NADPH)) | 645 | 1.54 | 759.1 | 1241.6 | 0.656 | 0.0003 | 0.042 | 0.9495 |
| 203505_at | ABCA1 | ATP-binding cassette, sub-family A (ABC1), member 1 | 19 | 1.54 | 308.8 | 468.3 | 0.820 | 0.0002 | 0.420 | 0.0063 |
| 229584_at | LRRK2 | leucine-rich repeat kinase 2 | 120892 | 1.54 | 762.3 | 1175.6 | 0.785 | 0.0002 | 0.312 | 0.0925 |
| 232375_at | | | | 1.54 | 281.5 | 461.9 | 0.770 | 0.0002 | 0.087 | 0.7738 |
| 235681_at | | | | 1.54 | 35.4 | 58.8 | 0.738 | 0.0002 | 0.290 | 0.0384 |
| 243934_at | ODF3B | Outer dense fiber of sperm tails 3B | 440836 | 1.54 | 85.4 | 139.5 | 0.890 | 0.0002 | 0.366 | 0.0260 |
| 1569401_at | CLEC12A | C-type lectin domain family 12, member A | 160364 | 1.54 | 236.4 | 373.8 | 0.785 | 0.0006 | 0.232 | 0.1584 |
| 203167_at | TIMP2 | TIMP metallopeptidase inhibitor 2 | 7077 | 1.53 | 611.5 | 934.1 | 0.797 | 0.0002 | 0.282 | 0.0835 |
| 204170_s_at | CKS2 | CDC28 protein kinase regulatory subunit 2 | 1164 | 1.53 | 372.0 | 557.7 | 0.663 | 0.0006 | 0.003 | 0.9511 |
| 208087_s_at | ZBP1 | Z-DNA binding protein 1 | 81030 | 1.53 | 168.5 | 266.7 | 0.720 | 0.0006 | 0.097 | 0.5826 |
| 228033_at | E2F7 | E2F transcription factor 7 | 144455 | 1.53 | 23.0 | 42.4 | 0.693 | 0.0057 | 0.105 | 0.5733 |
| 232283_at | TFEC | transcription factor EC | 22797 | 1.53 | 156.2 | 224.4 | 0.719 | 0.0116 | 0.116 | 0.7998 |
| 205099_s_at | CCR1 | chemokine (C—C motif) receptor 1 | 1230 | 1.52 | 659.6 | 950.1 | 0.821 | 0.0006 | 0.305 | 0.0925 |
| 205174_s_at | QPCT | glutaminyl-peptide cyclotransferase | 25797 | 1.52 | 717.2 | 1096.1 | 0.831 | 0.0002 | 0.483 | 0.0025 |
| 207926_at | GP5 | glycoprotein V (platelet) | 2814 | 1.52 | 79.4 | 117.4 | 0.396 | 0.0322 | -0.263 | 0.0335 |
| 218613_at | PSD3 | pleckstrin and Sec7 domain containing 3 | 23362 | 1.52 | 40.4 | 62.9 | 0.473 | 0.0029 | -0.144 | 0.2425 |
| 219259_at | SEMA4A | sema domain, immunoglobulin domain (Ig), transmembrane domain (TM) and short cytoplasmic domain, (semaphorin) 4A | 64218 | 1.52 | 449.9 | 670.5 | 0.740 | 0.0002 | 0.264 | 0.0152 |
| 222680_s_at | DTL | denticleless homolog (Drosophila) | 51514 | 1.52 | 58.0 | 103.5 | 0.797 | 0.0014 | 0.254 | 0.1476 |
| 227935_s_at | PCGF5 | polycomb group ring finger 5 | 84333 | 1.52 | 366.5 | 572.5 | 0.561 | 0.0029 | 0.021 | 0.9972 |
| 208121_s_at | PTPRO | protein tyrosine phosphatase, receptor type, O | 5800 | 1.51 | 206.3 | 313.2 | 0.584 | 0.0112 | -0.033 | 0.9511 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 213293_s_at | TRIM22 | tripartite motif-containing 22 | 10346 | 1.51 | 5473.7 | 8277.9 | 0.627 | 0.0002 | 0.027 | 0.8164 |
| 214084_x_at | LOC648998 | similar to Neutrophil cytosol factor 1 (NCF-1) (Neutrophil NADPH oxidase factor 1) (47 kDa neutrophil oxidase factor) (p47-phox) (NCF-47K) (47 kDa autosomal chronic granulomatous disease protein) (NOXO2) | 648998 | 1.51 | 1337.4 | 2025.4 | 0.783 | 0.0002 | 0.244 | 0.0517 |
| 241453_at | PTK2 | PTK2 protein tyrosine kinase 2 | 5747 | 1.51 | 19.0 | 30.5 | 0.522 | 0.0036 | -0.096 | 0.5293 |
| 1552553_a_at | NLRC4 | NLR family, CARD domain containing 4 | 58484 | 1.51 | 360.1 | 507.0 | 0.787 | 0.0009 | 0.348 | 0.0517 |
| 203329_at | PTPRM | protein tyrosine phosphatase, receptor type, M | 5797 | 0.66 | 231.6 | 158.3 | -0.662 | 0.0002 | -0.114 | 0.2472 |
| 204497_at | ADCY9 | adenylate cyclase 9 | 115 | 0.66 | 701.5 | 474.6 | -0.612 | 0.0002 | -0.029 | 0.7595 |
| 204688_at | SGCE | sarcoglycan, epsilon | 8910 | 0.66 | 49.2 | 34.1 | -0.726 | 0.0006 | -0.188 | 0.1788 |
| 204783_at | MLF1 | myeloid leukemia factor 1 | 4291 | 0.66 | 30.4 | 21.1 | -0.671 | 0.0002 | -0.122 | 0.2180 |
| 205758_at | CD8A | CD8a molecule | 925 | 0.66 | 4148.1 | 2966.3 | -0.710 | 0.0002 | -0.188 | 0.1117 |
| 205987_at | CD1C | CD1c molecule | 911 | 0.66 | 904.2 | 662.2 | -0.698 | 0.0009 | -0.241 | 0.0709 |
| 209469_at | GPM6A | glycoprotein M6A | 2823 | 0.66 | 49.7 | 36.6 | -0.701 | 0.0043 | -0.269 | 0.1006 |
| 213703_at | LOC150759 | hypothetical protein LOC150759 | 150759 | 0.66 | 293.7 | 202.8 | -0.635 | 0.0052 | -0.142 | 0.6238 |
| 217744_s_at | PERP | PERP, TP53 apoptosis effector | 64065 | 0.66 | 30.2 | 20.4 | -0.631 | 0.0002 | -0.157 | 0.1822 |
| 228030_at | | | | 0.66 | 1417.7 | 1017.5 | -0.563 | 0.0181 | 0.006 | 0.9972 |
| 228455_at | RBM15 | RNA binding motif protein 15 | 64783 | 0.66 | 250.4 | 172.9 | -0.693 | 0.0003 | -0.141 | 0.4840 |
| 229434_at | | | | 0.66 | 2225.0 | 1512.1 | -0.557 | 0.0024 | 0.007 | 0.9973 |
| 230713_at | | | | 0.66 | 312.0 | 214.1 | -0.600 | 0.0064 | -0.094 | 0.8336 |
| 232511_at | | | | 0.66 | 358.9 | 235.0 | -0.622 | 0.0101 | -0.090 | 0.8264 |
| 235203_at | | | | 0.66 | 302.3 | 208.6 | -0.718 | 0.0002 | -0.097 | 0.3383 |
| 235374_at | MDH1 | Malate dehydrogenase 1, NAD (soluble) | 4190 | 0.66 | 334.6 | 219.6 | -0.666 | 0.0002 | -0.141 | 0.4453 |
| 236999_at | | | | 0.66 | 42.6 | 27.3 | -0.567 | 0.0099 | 0.020 | 0.8972 |
| 239540_at | | | | 0.66 | 102.7 | 65.1 | -0.589 | 0.0002 | -0.018 | 0.9511 |
| 239654_at | CHD9 | Chromodomain helicase DNA binding protein 9 | 80205 | 0.66 | 182.3 | 128.8 | -0.498 | 0.0162 | 0.108 | 0.7233 |
| 241775_at | | | | 0.66 | 346.4 | 231.1 | -0.512 | 0.0118 | 0.070 | 0.8528 |
| 1556467_at | ZNF80 | Zinc finger protein 80 | 7634 | 0.66 | 114.1 | 72.6 | -0.633 | 0.0173 | -0.100 | 0.3941 |
| 1565852_at | | | | 0.66 | 213.4 | 143.4 | -0.475 | 0.0002 | 0.207 | 0.3878 |
| 203130_s_at | KIF5C | kinesin family member 5C | 3800 | 0.65 | 540.9 | 362.6 | -0.777 | 0.0006 | -0.183 | 0.1392 |
| 205419_at | GPR183 | G protein-coupled receptor 183 | 1880 | 0.65 | 4311.8 | 2955.9 | -0.726 | 0.0002 | -0.158 | 0.3020 |
| 210517_s_at | AKAP12 | A kinase (PRKA) anchor protein 12 | 9590 | 0.65 | 196.8 | 159.6 | -0.856 | 0.0081 | -0.315 | 0.0772 |
| 212609_s_at | AKT3 | V-akt murine thymoma viral oncogene homolog 3 (protein kinase B, gamma) | 10000 | 0.65 | 503.0 | 328.0 | -0.794 | 0.0002 | -0.226 | 0.0152 |
| 213534_s_at | PASK | PAS domain containing serine/threonine kinase | 23178 | 0.65 | 594.2 | 417.9 | -0.807 | 0.0014 | -0.222 | 0.1543 |
| 223093_at | ANKH | ankylosis, progressive homolog (mouse) | 56172 | 0.65 | 365.9 | 242.6 | -0.812 | 0.0002 | -0.239 | 0.0025 |
| 226627_at | 41160 | septin 8 | 23176 | 0.65 | 274.0 | 186.6 | -0.676 | 0.0002 | -0.090 | 0.1978 |
| 227755_at | | | | 0.65 | 1938.9 | 1271.2 | -0.677 | 0.0002 | -0.076 | 0.4840 |
| 229357_at | ADAMTS5 | ADAM metallopeptidase with thrombospondin type 1 motif, 5 | 11096 | 0.65 | 59.1 | 39.9 | -0.633 | 0.0104 | -0.010 | 0.9828 |
| 230120_s_at | PLGLB2 | plasminogen-like B2 | 5342 | 0.65 | 230.2 | 169.7 | -0.710 | 0.0068 | -0.138 | 0.5579 |
| 230230_at | | | | 0.65 | 304.4 | 189.3 | -0.780 | 0.0002 | -0.259 | 0.0456 |
| 230961_at | | | | 0.65 | 143.1 | 97.0 | -0.685 | 0.0017 | -0.091 | 0.8057 |
| 235651_at | | | | 0.65 | 437.2 | 270.0 | -0.682 | 0.0002 | -0.100 | 0.5994 |
| 235716_at | | | | 0.65 | 668.6 | 450.0 | -0.563 | 0.0003 | 0.001 | 0.9973 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 236621_at | RPS27 /// RPS27P13 /// RPS27P21 /// RPS27P23 /// RPS27P29 /// RPS27P6 /// RPS27P7 | ribosomal protein S27 /// ribosomal protein S27 pseudogene 13 /// ribosomal protein S27 pseudogene 21 /// ribosomal protein /// S27 pseudogene 23 /// ribosomal protein S27 pseudogene 29 /// ribosomal protein S27 pseudogene 6 /// ribosomal protein S27 pseudogene 7 | 100130070 /// 100130775 /// 100131787 /// 100131905 /// 100132291 /// 100132488 /// 6232 | 0.65 | 106.7 | 68.6 | −0.448 | 0.0421 | 0.127 | 0.7558 |
| 238568_s_at | S100A10 | S100 calcium binding protein A10 | 6281 | 0.65 | 123.7 | 82.3 | −0.581 | 0.0002 | 0.001 | 0.9973 |
| 238909_at | OFD1 | oral-facial-digital syndrome 1 | 8481 | 0.65 | 597.3 | 395.7 | −0.565 | 0.0017 | 0.047 | 0.8972 |
| 241751_at | | ribosomal protein | | 0.65 | 122.5 | 82.2 | −0.629 | 0.0075 | −0.044 | 0.9495 |
| 241845_at | | | | 0.65 | 128.3 | 85.6 | −0.675 | 0.0019 | −0.071 | 0.7998 |
| 242428_at | DCUN1D1 | DCN1, defective in cullin neddylation 1, domain containing 1 (S. cerevisiae) | 54165 | 0.65 | 90.4 | 60.1 | −0.556 | 0.0002 | 0.068 | 0.7586 |
| 242920_at | | | | 0.65 | 727.9 | 478.3 | −0.530 | 0.0247 | 0.117 | 0.7586 |
| 1556239_a_at | | | | 0.65 | 237.0 | 147.8 | −0.677 | 0.0002 | −0.109 | 0.3969 |
| 1569482_at | | | | 0.65 | 56.7 | 35.0 | −0.606 | 0.0012 | −0.039 | 0.8994 |
| 203913_s_at | HPGD | hydroxyprostaglandin dehydrogenase 15-(NAD) | 3248 | 0.64 | 110.9 | 69.5 | −0.679 | 0.0012 | 0.012 | 0.9779 |
| 204160_s_at | ENPP4 | ectonucleotide pyrophosphatase/phosphodiesterase 4 (putative function) | 22875 | 0.64 | 739.5 | 487.3 | −0.653 | 0.0003 | 0.060 | 0.7988 |
| 209030_s_at | CADM1 | cell adhesion molecule 1 | 23705 | 0.64 | 155.9 | 93.9 | −0.660 | 0.0002 | −0.051 | 0.7915 |
| 209750_at | NR1D2 | nuclear receptor subfamily 1, group D, member 2 | 9975 | 0.64 | 661.6 | 436.9 | −0.788 | 0.0002 | −0.273 | 0.0223 |
| 213268_at | CAMTA1 | calmodulin binding transcription activator 1 | 23261 | 0.64 | 53.4 | 37.6 | −0.733 | 0.0003 | −0.213 | 0.1966 |
| 215483_at | AKAP9 | A kinase (PRKA) anchor protein (yotiao) 9 | 10142 | 0.64 | 138.6 | 93.5 | −0.559 | 0.0415 | −0.032 | 0.9575 |
| 215567_at | FCF1 | FCF1 small subunit (SSU) processome component homolog (S. cerevisiae) | 51077 | 0.64 | 244.9 | 155.6 | −0.648 | 0.0003 | −0.020 | 0.9269 |
| 216945_x_at | PASK | PAS domain containing serine/threonine kinase | 23178 | 0.64 | 700.0 | 485.7 | −0.842 | 0.0009 | −0.262 | 0.0906 |
| 217506_at | LOC339290 | Hypothetical LOC339290 | 339290 | 0.64 | 179.1 | 117.1 | −0.738 | 0.0002 | −0.121 | 0.4871 |
| 224766_at | RPL37 | Ribosomal protein L37 | 6167 | 0.64 | 141.9 | 88.8 | −0.653 | 0.0002 | −0.122 | 0.3024 |
| 230722_at | BNC2 | basonuclin 2 | 54796 | 0.64 | 55.9 | 36.1 | −0.650 | 0.0003 | 0.056 | 0.7810 |
| 232166_at | KIAA1377 | KIAA1377 | 57562 | 0.64 | 61.4 | 38.3 | −0.697 | 0.0002 | −0.028 | 0.8553 |
| 232737_s_at | ENPP3 | ectonucleotide pyrophosphatase/phosphodiesterase 3 | 5169 | 0.64 | 26.6 | 17.6 | −0.768 | 0.0002 | −0.197 | 0.1114 |
| 235526_at | SOX6 | SRY (sex determining region Y)-box 6 | 55553 | 0.64 | 345.1 | 206.9 | −0.752 | 0.0024 | −0.042 | 0.9269 |
| 237054_at | ENPP5 | ectonucleotide pyrophosphatase/phosphodiesterase 5 (putative function) | 59084 | 0.64 | 93.1 | 61.4 | −0.725 | 0.0019 | −0.100 | 0.6284 |
| 238121_at | GK5 | glycerol kinase 5 (putative) | 256356 | 0.64 | 405.0 | 264.3 | −0.664 | 0.0002 | −0.019 | 0.8553 |
| 238623_at | | | | 0.64 | 189.4 | 127.3 | −0.757 | 0.0002 | −0.124 | 0.3624 |
| 239064_at | | | | 0.64 | 343.8 | 231.8 | −0.678 | 0.0002 | −0.012 | 0.9973 |
| 239635_at | | | | 0.64 | 328.9 | 217.3 | −0.559 | 0.0019 | 0.052 | 0.8553 |
| 239954_at | RBM14 | RNA binding motif protein 14 | 10432 | 0.64 | 262.5 | 170.3 | −0.681 | 0.0014 | −0.113 | 0.7190 |
| 242673_at | ZNF160 | zinc finger protein 160 | 90338 | 0.64 | 332.0 | 206.9 | −0.562 | 0.0177 | 0.036 | 0.9199 |
| 242693_at | | | | 0.64 | 411.8 | 274.5 | −0.557 | 0.0038 | 0.017 | 0.9779 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 1557828_a_at | C5orf28 | Chromosome 5 open reading frame 28 | 64417 | 0.64 | 246.4 | 163.3 | −0.672 | 0.0003 | −0.129 | 0.6418 |
| 1559413_at | TCP11L2 | t-complex 11 (mouse)-like 2 | 255394 | 0.64 | 437.3 | 279.9 | −0.595 | 0.0014 | 0.053 | 0.8675 |
| 1566608_at | | | | 0.64 | 232.6 | 144.4 | −0.636 | 0.0077 | −0.078 | 0.7998 |
| 202336_s_at | PAM | peptidylglycine alpha-amidating monooxygenase | 5066 | 0.63 | 2010.2 | 1338.0 | −0.641 | 0.0002 | 0.099 | 0.4315 |
| 206108_s_at | SFRS6 | splicing factor, arginine/serine-rich 6 | 6431 | 0.63 | 202.4 | 124.0 | −0.677 | 0.0116 | −0.074 | 0.7810 |
| 206279_at | PRKY | protein kinase, Y-linked | 5616 | 0.63 | 120.3 | 63.9 | −0.707 | 0.0014 | −0.107 | 0.5502 |
| 207723_s_at | KLRC3 | killer cell lectin-like receptor subfamily C, member 3 | 3823 | 0.63 | 260.4 | 183.3 | −0.851 | 0.0012 | −0.265 | 0.0990 |
| 211937_at | EIF4B | eukaryotic translation initiation factor 4B | 1975 | 0.63 | 2600.4 | 1729.4 | −0.799 | 0.0002 | −0.193 | 0.0334 |
| 212599_at | AUTS2 | autism susceptibility candidate 2 | 26053 | 0.63 | 1306.9 | 826.7 | −0.740 | 0.0002 | −0.138 | 0.2411 |
| 212958_x_at | PAM | peptidylglycine alpha-amidating monooxygenase | 5066 | 0.63 | 1457.7 | 980.9 | −0.629 | 0.0002 | 0.077 | 0.5826 |
| 216920_s_at | TARP /// TRGC2 | TCR gamma alternate reading frame protein /// T cell receptor gamma constant 2 | 445347 /// 6967 | 0.63 | 5181.8 | 3406.1 | −0.740 | 0.0002 | −0.160 | 0.1788 |
| 225127_at | TMEM181 | transmembrane protein 181 | 57583 | 0.63 | 895.8 | 567.2 | −0.671 | 0.0002 | −0.056 | 0.7158 |
| 225270_at | NEO1 | neogenin homolog 1 (chicken) | 4756 | 0.63 | 166.1 | 102.9 | −0.669 | 0.0002 | 0.113 | 0.2472 |
| 229692_at | | | | 0.63 | 320.3 | 210.0 | −0.655 | 0.0019 | −0.042 | 0.9284 |
| 232431_at | | | | 0.63 | 494.9 | 322.6 | −0.597 | 0.0066 | 0.055 | 0.8948 |
| 232521_at | PCSK7 | proprotein convertase subtilisin/kexin type 7 | 9159 | 0.63 | 433.6 | 285.3 | −0.666 | 0.0014 | −0.129 | 0.6500 |
| 232529_at | SP3 | Sp3 transcription factor | 6670 | 0.63 | 588.8 | 378.7 | −0.616 | 0.0003 | −0.009 | 0.9754 |
| 1565868_a_at | CD44 | CD44 molecule (Indian blood group) | 960 | 0.63 | 177.6 | 104.0 | −0.585 | 0.0026 | 0.012 | 0.9972 |
| 1566901_at | TGIF1 | TGFB-induced factor homeobox 1 | 7050 | 0.63 | 78.1 | 50.1 | −0.576 | 0.0045 | −0.037 | 0.8960 |
| 203803_at | PCYOX1 | prenylcysteine oxidase 1 | 51449 | 0.62 | 104.1 | 65.9 | −0.810 | 0.0002 | −0.122 | 0.3726 |
| 210121_at | B3GALT2 | UDP-Gal:betaGlcNAc beta 1,3-galactosyltransferase, polypeptide 2 | 8707 | 0.62 | 46.1 | 25.8 | −0.845 | 0.0050 | −0.248 | 0.3271 |
| 210879_s_at | RAB11FIP5 | RAB11 family interacting protein 5 (class I) | 26056 | 0.62 | 399.2 | 246.7 | −0.758 | 0.0002 | −0.118 | 0.2435 |
| 214247_s_at | DKK3 | **dickkopf homolog 3 (*Xenopus laevis*) | 27122 | 0.62 | 130.1 | 84.3 | −0.923 | 0.0002 | −0.309 | 0.0176** |
| 232483_s_t | MED17 | mediator complex subunit 17 | 9440 | 0.62 | 202.3 | 130.3 | −0.632 | 0.0003 | −0.076 | 0.7998 |
| 233480_at | TMEM43 | Transmembrane protein 43 | 79188 | 0.62 | 251.6 | 156.7 | −0.707 | 0.0003 | −0.022 | 0.9511 |
| 237542_at | | | | 0.62 | 67.7 | 41.5 | −0.652 | 0.0002 | 0.095 | 0.5994 |
| 238257_at | MLLT10 | Myeloid/lymphoid or mixed-lineage leukemia (trithorax homolog, *Drosophila*); translocated to, 10 | 8028 | 0.62 | 27.4 | 16.6 | −0.616 | 0.0031 | 0.016 | 0.9694 |
| 240859_at | ZFYVE16 | zinc finger, FYVE domain containing 16 | 9765 | 0.62 | 178.7 | 103.8 | −0.484 | 0.0144 | 0.301 | 0.1584 |
| 244425_at | | | | 0.62 | 376.3 | 237.2 | −0.741 | 0.0033 | −0.078 | 0.8913 |
| 1557300_s_at | | | | 0.62 | 386.7 | 245.6 | −0.694 | 0.0003 | −0.064 | 0.8960 |
| 1561973_at | SMARCC2 | SWI/SNF related, matrix associated, actin dependent regulator of chromatin, subfamily c, member 2 | 6601 | 0.62 | 80.8 | 52.1 | −0.614 | 0.0003 | 0.056 | 0.8528 |
| 204059_s_at | ME1 | malic enzyme 1, NADP(+)-dependent, cytosolic | 4199 | 0.61 | 211.3 | 142.0 | −0.573 | 0.0300 | 0.259 | 0.2945 |
| 206267_s_at | MATK | megakaryocyte-associated tyrosine kinase | 4145 | 0.61 | 523.0 | 335.2 | −0.807 | 0.0002 | −0.182 | 0.1279 |
| 206648_at | ZNF571 | zinc finger protein 571 | 51276 | 0.61 | 225.4 | 131.7 | −0.918 | 0.0002 | −0.317 | 0.0025 |
| 209733_at | MID2 | midline 2 | 11043 | 0.61 | 205.5 | 128.2 | −0.828 | 0.0002 | −0.101 | 0.4360 |
| 209813_x_at | TARP | TCR gamma alternate reading frame protein | 445347 | 0.61 | 2518.7 | 1634.9 | −0.786 | 0.0002 | −0.177 | 0.1511 |
| 215388_s_at | CFH /// CFHR1 | complement factor H /// complement factor H-related 1 | 3075 /// 3078 | 0.61 | 108.9 | 70.5 | −0.861 | 0.0002 | −0.169 | 0.3020 |
| 215806_x_at | TARP /// TRGC2 | TCR gamma alternate reading frame protein /// T cell receptor gamma constant 2 | 445347 /// 6967 | 0.61 | 2812.0 | 1798.5 | −0.805 | 0.0002 | −0.187 | 0.1220 |
| 232889_at | | | | 0.61 | 539.2 | 342.8 | −0.674 | 0.0075 | −0.024 | 0.9973 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 234165_at | PTGDR | prostaglandin D2 receptor (DP) | 5729 | 0.61 | 211.5 | 127.7 | -0.852 | 0.0002 | -0.142 | 0.3510 |
| 236419_at | | | | 0.61 | 304.1 | 190.6 | -0.652 | 0.0210 | 0.023 | 0.9284 |
| 239442_at | | | | 0.61 | 381.0 | 239.3 | -0.802 | 0.0002 | -0.161 | 0.4156 |
| 239808_at | CEP68 | centrosomal protein 68 kDa | 23177 | 0.61 | 502.0 | 321.2 | -0.763 | 0.0003 | -0.161 | 0.4871 |
| 1553311_at | C20orf197 | chromosome 20 open reading frame 197 | 284756 | 0.61 | 117.3 | 76.2 | -0.627 | 0.0002 | 0.219 | 0.1300 |
| 1561578_s_at | MCART6 | mitochondrial carrier triple repeat 6 | 401612 | 0.61 | 38.7 | 23.0 | -0.729 | 0.0002 | -0.035 | 0.8553 |
| 204161_s_at | ENPP4 | ectonucleotide pyrophosphatase/phosphodiesterase 4 (putative function) | 22875 | 0.60 | 370.7 | 233.8 | -0.798 | 0.0002 | 0.015 | 0.9511 |
| 210288_at | KLRG1 | killer cell lectin-like receptor subfamily G, member 1 | 10219 | 0.60 | 446.2 | 289.0 | -0.807 | 0.0002 | -0.134 | 0.1353 |
| 211144_x_at | TARP /// TRGC2 | TCR gamma alternate reading frame protein /// T cell receptor gamma constant 2 | 445347 /// 6967 | 0.60 | 2602.4 | 1670.0 | -0.811 | 0.0002 | -0.188 | 0.1502 |
| 211343_s_at | COL13A1 | collagen, type XIII, alpha 1 | 1305 | 0.60 | 55.0 | 30.5 | -0.863 | 0.0002 | -0.155 | 0.2862 |
| 219700_at | PLXDC1 | plexin domain containing 1 | 57125 | 0.60 | 168.9 | 111.1 | -1.002 | 0.0002 | -0.456 | 0.0034 |
| 220076_at | ANKH | ankylosis, progressive homolog (mouse) | 56172 | 0.60 | 77.0 | 46.2 | -0.885 | 0.0002 | -0.164 | 0.0791 |
| 225219_at | SMAD5 | SMAD family member 5 | 4090 | 0.60 | 527.2 | 324.5 | -0.779 | 0.0002 | -0.035 | 0.8948 |
| 226225_at | MCC | mutated in colorectal cancers | 4163 | 0.60 | 102.2 | 66.1 | -0.998 | 0.0003 | -0.348 | 0.0335 |
| 227273_at | | | | 0.60 | 108.6 | 66.3 | -0.844 | 0.0002 | -0.149 | 0.1074 |
| 230494_at | SLC20A1 | Solute carrier family 20 (phosphate transporter), member 1 | 6574 | 0.60 | 871.4 | 559.6 | -0.609 | 0.0002 | 0.128 | 0.5826 |
| 238478_at | BNC2 | basonuclin 2 | 54796 | 0.60 | 52.3 | 33.1 | -0.781 | 0.0002 | -0.020 | 0.8972 |
| 241018_at | TMEM59 | transmembrane protein 59 | 9528 | 0.60 | 181.6 | 110.9 | -0.751 | 0.0002 | 0.002 | 0.9973 |
| 241036_at | | | | 0.60 | 330.8 | 187.9 | -0.757 | 0.0003 | -0.076 | 0.7998 |
| 209710_at | GATA2 | GATA binding protein 2 | 2624 | 0.59 | 938.1 | 681.8 | -1.010 | 0.0012 | -0.385 | 0.0293 |
| 214163_at | HSPB11 | heat shock protein family B (small), member 11 | 51668 | 0.59 | 134.7 | 81.7 | -0.812 | 0.0002 | -0.097 | 0.6456 |
| 226665_at | AHSA2 | AHA1, activator of heat shock 90 kDa protein ATPase homolog 2 (yeast) | 130872 | 0.59 | 626.5 | 380.1 | -0.896 | 0.0002 | -0.223 | 0.1747 |
| 233019_at | CNOT7 | CCR4-NOT transcription complex, subunit 7 | 29883 | 0.59 | 578.8 | 352.8 | -0.821 | 0.0002 | -0.161 | 0.4453 |
| 233713_at | | | | 0.59 | 228.0 | 141.5 | -0.821 | 0.0019 | -0.150 | 0.6382 |
| 238026_at | RPL35A | ribosomal protein L35a | 6165 | 0.59 | 688.0 | 399.2 | -0.914 | 0.0002 | -0.212 | 0.0176 |
| 243915_at | | | | 0.59 | 276.9 | 179.9 | -0.721 | 0.0093 | -0.084 | 0.8675 |
| 206404_at | FGF9 | fibroblast growth factor 9 (glia-activating factor) | 2254 | 0.58 | 139.6 | 83.3 | -0.882 | 0.0002 | -0.150 | 0.1464 |
| 222073_at | COL4A3 | collagen, type IV, alpha 3 (Goodpasture antigen) | 1285 | 0.58 | 46.5 | 28.3 | -0.882 | 0.0002 | -0.095 | 0.6382 |
| 225147_at | CYTH3 | cytohesin 3 | 9265 | 0.58 | 618.8 | 364.7 | -0.841 | 0.0009 | -0.126 | 0.0896 |
| 226475_at | FAM118A | family with sequence similarity 118, member A | 55007 | 0.58 | 694.1 | 433.4 | -0.847 | 0.0002 | -0.111 | 0.3086 |
| 230543_at | | | | 0.58 | 412.7 | 255.9 | -0.800 | 0.0003 | 0.092 | 0.8892 |
| 236833_at | TTC16 | tetratricopeptide repeat domain 16 | 158248 | 0.58 | 201.2 | 116.1 | -0.817 | 0.0002 | -0.058 | 0.7233 |
| 239243_at | ZNF638 | Zinc finger protein 638 | 27332 | 0.58 | 285.5 | 164.2 | -0.783 | 0.0031 | 0.054 | 0.9199 |
| 243578_at | | | | 0.58 | 85.2 | 48.7 | -0.769 | 0.0077 | 0.226 | 0.3033 |
| 1563473_at | | | | 0.58 | 564.6 | 350.9 | -0.605 | 0.0057 | 0.004 | 0.9973 |
| 214470_at | KLRB1 | killer cell lectin-like receptor subfamily B, member 1 | 3820 | 0.57 | 5524.3 | 3359.6 | -0.678 | 0.0002 | -0.203 | 0.1433 |
| 216748_at | PYHIN1 | pyrin and HIN domain family, member 1 | 149628 | 0.57 | 213.5 | 123.2 | -0.992 | 0.0002 | -0.101 | 0.6003 |
| 225525_at | CTA-221G9.4 | KIAA1671 protein | 85379 | 0.57 | 705.0 | 409.6 | -0.816 | 0.0002 | -0.230 | 0.1258 |
| 229026_at | | | | 0.57 | 4993.3 | 2753.4 | -0.942 | 0.0002 | -0.144 | 0.3318 |
| 229147_at | | | | 0.57 | 101.1 | 50.5 | -0.901 | 0.0003 | -0.232 | 0.0939 |
| 230104_s_at | TPPP | tubulin polymerization promoting protein | 11076 | 0.57 | 141.2 | 77.6 | -0.892 | 0.0002 | -0.065 | 0.5309 |
| 233406_at | | | | 0.57 | 340.9 | 207.1 | -0.844 | 0.0002 | -0.051 | 0.8972 |
| 1566324_a_at | MAF | v-maf musculoaponeurotic fibrosarcoma oncogene homolog (avian) | 4094 | 0.57 | 67.7 | 36.4 | -0.795 | 0.0002 | 0.075 | 0.8553 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 202975_s_at | RHOBTB3 | Rho-related BTB domain containing 3 | 22836 | 0.56 | 87.6 | 49.5 | −0.870 | 0.0002 | 0.001 | 0.9880 |
| 226682_at | RORA | RAR-related orphan receptor A | 6095 | 0.56 | 4900.1 | 2815.3 | −0.961 | 0.0002 | −0.211 | 0.0405 |
| 226677_at | | | | 0.56 | 73.0 | 42.4 | −0.935 | 0.0002 | −0.076 | 0.6131 |
| 230563_at | RASGEF1A | RasGEF domain family, member 1A | 221002 | 0.56 | 690.7 | 403.9 | −0.744 | 0.0006 | 0.153 | 0.3020 |
| 1557459_at | | | | 0.56 | 55.2 | 31.9 | −0.778 | 0.0002 | 0.068 | 0.7998 |
| 207067_s_at | HDC | histidine decarboxylase | 3067 | 0.55 | 479.7 | 306.3 | −0.976 | 0.0006 | −0.244 | 0.1544 |
| 213222_at | PLCB1 | phospholipase C, beta 1 (phosphoinositide-specific) | 23236 | 0.55 | 731.1 | 439.8 | −0.860 | 0.0002 | 0.068 | 0.8960 |
| 213954_at | FAM169A | family with sequence similarity 169, member A | 26049 | 0.55 | 141.6 | 78.6 | −1.004 | 0.0002 | −0.268 | 0.0207 |
| 227722_at | RPS23 | ribosomal protein S23 | 6228 | 0.55 | 328.9 | 202.7 | −0.975 | 0.0002 | −0.100 | 0.6234 |
| 231776_at | EOMES | eomesodermin homolog (Xenopus laevis) | 8320 | 0.55 | 2196.9 | 1226.6 | −0.922 | 0.0002 | −0.094 | 0.6341 |
| 244726_at | | | | 0.55 | 216.7 | 119.4 | −0.730 | 0.0019 | 0.170 | 0.5410 |
| 1552283_s_at | ZDHHC11 | zinc finger, DHHC-type containing 11 | 79844 | 0.55 | 59.7 | 35.1 | −0.881 | 0.0002 | −0.062 | 0.8135 |
| 210095_s_at | IGFBP3 | insulin-like growth factor binding protein 3 | 3486 | 0.54 | 275.7 | 157.6 | −1.063 | 0.0002 | −0.222 | 0.1112 |
| 221646_s_at | ZDHHC11 | zinc finger, DHHC-type containing 11 | 79844 | 0.54 | 221.4 | 128.7 | −0.896 | 0.0002 | −0.050 | 0.8762 |
| 233813_at | PPP1R16B | protein phosphatase 1, regulatory (inhibitor) subunit 16B | 26051 | 0.54 | 406.9 | 216.2 | −0.886 | 0.0012 | −0.082 | 0.8528 |
| 204749_at | NAP1L3 | nucleosome assembly protein 1-like 3 | 4675 | 0.53 | 282.3 | 162.6 | −1.173 | 0.0002 | −0.307 | 0.0376 |
| 224657_at | ERRFI1 | ERBB receptor feedback inhibitor 1 | 54206 | 0.53 | 137.6 | 70.7 | −0.922 | 0.0002 | −0.003 | 0.9426 |
| 232752_at | | | | 0.53 | 169.6 | 90.5 | −1.128 | 0.0002 | −0.255 | 0.0702 |
| 1562255_at | SYTL3 | synaptotagmin-like 3 | 94120 | 0.53 | 308.5 | 168.5 | −0.812 | 0.0021 | 0.123 | 0.8528 |
| 204790_at | SMAD7 | SMAD family member 7 | 4092 | 0.52 | 577.2 | 298.0 | −1.004 | 0.0002 | −0.093 | 0.3624 |
| 211734_s_at | FCER1A | Fc fragment of IgE, high affinity I, receptor for; alpha polypeptide | 2205 | 0.52 | 1769.7 | 1227.5 | −1.379 | 0.0012 | −0.818 | 0.0025 |
| 221916_at | NEFL | neurofilament, light polypeptide | 4747 | 0.52 | 304.8 | 189.5 | −1.103 | 0.0002 | −0.272 | 0.1966 |
| 1562698_x_at | LOC339988 | hypothetical protein LOC339988 | 339988 | 0.52 | 915.6 | 512.5 | −1.008 | 0.0002 | −0.114 | 0.2347 |
| 213849_s_at | PPP2R2B | protein phosphatase 2 (formerly 2A), regulatory subunit B, beta isoform | 5521 | 0.51 | 547.2 | 294.9 | −1.017 | 0.0002 | −0.088 | 0.6199 |
| 200897_s_at | PALLD | palladin, cytoskeletal associated protein | 23022 | 0.49 | 646.1 | 345.5 | −1.101 | 0.0002 | −0.038 | 0.7549 |
| 225842_at | PHLDA1 | pleckstrin homology-like domain, family A, member 1 | 22822 | 0.49 | 281.6 | 129.4 | −1.028 | 0.0002 | 0.057 | 0.8528 |
| 226625_at | TGFBR3 | transforming growth factor, beta receptor III | 7049 | 0.49 | 5639.7 | 2976.8 | −1.109 | 0.0002 | −0.162 | 0.1788 |
| 1555579_s_at | PTPRM | protein tyrosine phosphatase, receptor type, M | 5797 | 0.49 | 471.4 | 246.0 | −1.076 | 0.0002 | −0.129 | 0.4268 |
| 277819_at | LGR6 | leucine-rich repeat-containing G protein-coupled receptor 6 | 59352 | 0.48 | 358.2 | 162.9 | −1.111 | 0.0002 | −0.174 | 0.1444 |
| 242463_x_at | ZNF600 | zinc finger protein 600 | 162966 | 0.48 | 1858.6 | 847.1 | −1.156 | 0.0002 | −0.200 | 0.1006 |
| 213906_at | MYBL1 | v-myb myeloblastosis viral oncogene homolog (avian)-like 1 | 4603 | 0.47 | 3612.2 | 1774.2 | −1.256 | 0.0002 | −0.353 | 0.0034 |
| 202458_at | PRSS23 | protease, serine, 23 | 11098 | 0.45 | 940.9 | 458.1 | −1.224 | 0.0003 | −0.171 | 0.3099 |
| 204731_at | TGFBR3 | transforming growth factor, beta receptor III | 7049 | 0.45 | 2468.6 | 1220.9 | −1.222 | 0.0002 | −0.144 | 0.2710 |
| 209031_at | CADM1 | cell adhesion molecule 1 | 23705 | 0.45 | 236.9 | 98.0 | −1.153 | 0.0002 | −0.029 | 0.9269 |
| 209883_at | GLT25D2 | glycosyltransferase 25 domain containing 2 | 23127 | 0.45 | 240.5 | 99.4 | −1.222 | 0.0002 | −0.148 | 0.1223 |
| 220231_at | C7orf16 | chromosome 7 open reading frame 16 | 10842 | 0.45 | 161.5 | 72.5 | −1.290 | 0.0002 | −0.030 | 0.9269 |
| 220952_s_at | PLEKHA5 | pleckstrin homology domain containing, family A, member 5 | 54477 | 0.45 | 291.2 | 154.1 | −1.279 | 0.0002 | −0.184 | 0.1155 |
| 225688_s_at | PHLDB2 | pleckstrin homology-like domain, family B, member 2 | 90102 | 0.45 | 451.0 | 211.9 | −1.221 | 0.0002 | −0.138 | 0.3079 |
| 232686_at | SIGLECP3 | sialic acid binding Ig-like lectin, pseudogene 3 | 284367 | 0.45 | 283.3 | 142.3 | −1.289 | 0.0002 | −0.160 | 0.1223 |

TABLE 9-continued

Gene Transcripts Differentially Expressed in SLE Patients

| Affymetrix ProbeSet ID | Gene Symbol | Gene Title | Entrez Gene | Fold Change | Mean Values HD | Mean Values SLE | Effect of disease Estimate | Effect of disease p-values | Effect of flares Estimate | Effect of flares p-values |
|---|---|---|---|---|---|---|---|---|---|---|
| 226603_at | KIF21A | kinesin family member 21A | 55605 | 0.44 | 701.9 | 325.9 | −1.310 | 0.0002 | −0.214 | 0.1474 |
| 228658_at | MIAT | myocardial infarction associated transcript (non-protein coding) | 440823 | 0.44 | 491.8 | 226.4 | −1.194 | 0.0002 | −0.100 | 0.7312 |
| 219629_at | FAM118A | family with sequence similarity 118, member A | 55007 | 0.43 | 467.9 | 225.4 | −1.182 | 0.0006 | −0.038 | 0.8553 |
| 230923_at | FAM19A1 | family with sequence similarity 19 (chemokine (C—C motif)-like), member A1 | 407738 | 0.43 | 267.2 | 124.5 | −1.417 | 0.0002 | −0.246 | 0.0935 |
| 204589_at | NUAK1 | NUAK family, SNF1-like kinase, 1 | 9891 | 0.41 | 78.3 | 29.2 | −1.314 | 0.0002 | −0.034 | 0.8553 |
| 231647_s_at | FCRL5 | Fc receptor-like 5 | 83416 | 0.41 | 129.2 | 74.4 | −1.273 | 0.0026 | −0.186 | 0.7586 |
| 204811_s_at | CACNA2D2 | calcium channel, voltage-dependent, alpha 2/delta subunit 2 | 9254 | 0.40 | 540.0 | 225.5 | −1.347 | 0.0002 | −0.107 | 0.3340 |
| 224901_at | SCD5 | stearoyl-CoA desaturase 5 | 79966 | 0.40 | 271.8 | 108.8 | −1.390 | 0.0002 | −0.138 | 0.1984 |
| 225496_s_at | SYTL2 | synaptotagmin-like 2 | 54843 | 0.39 | 1077.2 | 434.4 | −1.445 | 0.0002 | −0.124 | 0.3099 |
| 226279_at | PRSS23 | protease, serine, 23 | 11098 | 0.35 | 790.7 | 311.1 | −1.632 | 0.0002 | −0.168 | 0.3383 |
| 235874_at | PRSS35 | protease, serine, 35 | 167681 | 0.35 | 47.8 | 14.0 | −1.568 | 0.0002 | −0.054 | 0.7356 |
| 203216_s_at | MYO6 | myosin VI | 4646 | 0.32 | 88.0 | 27.9 | −1.726 | 0.0002 | −0.173 | 0.2419 |
| 203562_at | FEZ1 | fasciculation and elongation protein zeta 1 (zygin I) | 9638 | 0.29 | 263.0 | 86.1 | −1.894 | 0.0002 | −0.077 | 0.5981 |
| 1560263_at | | | | 0.28 | 182.8 | 73.5 | −1.756 | 0.0002 | 0.122 | 0.6274 |

OTE: Bolded are probesets showing significant effect from FLARE based on p-values obtained by Marcov chain Monte-Carlo sampling Example 3

Proteomic Patterns among Groups of SLE Patients

Autoantibodies in the form of immune complexes contribute to lupus pathology, and distinct autoantibody specificities have been associated with particular clinical manifestations of disease. The titer of 40 autoantibodies for each SLE visit was determined, using multiplex analysis of plasma samples. Five autoantibodies were significantly deregulated (FC>1.5; p<0.05, 5% FDR) between SLE patients and HDs based on linear mixed model analysis (Table 10). Plasma anti-dsDNA, anti-histone, anti-histone H2b and anti-RNP(c) antibodies increased significantly during the flares.

Figure 3A:
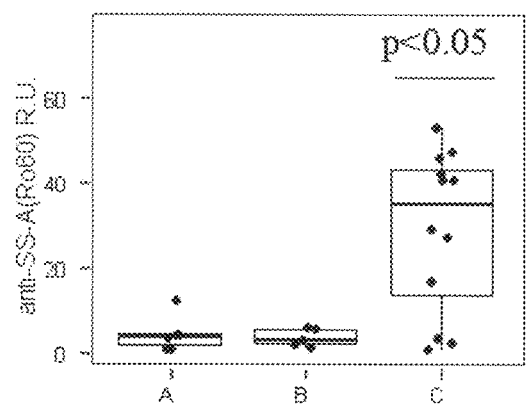
FIG. 3A shows relative units of anti-SS-A/Ro autoantibody.

There was also an observed significant and striking increase of anti-SSA/Ro autoantibodies in group C of SLE patients (p<0.05) (FIG. 3A).

Analysis of 41 inflammatory biomarkers identified 19 factors with significantly different plasma levels in SLE and HD samples (FC>1.5, p<0.05, 5% FDR) (Table 10). Among the inflammatory biomarkers identified, prolactin showed the greatest increase in SLE patients compared with HDs. Linear mixed model analysis demonstrated a significant effect of 14 analytes on lupus disease and an overlapping but not identical group of 13 plasma factors (p<0.05, 5% FDR) on lupus flares, as indicated in Table 10.

Figure 3B:
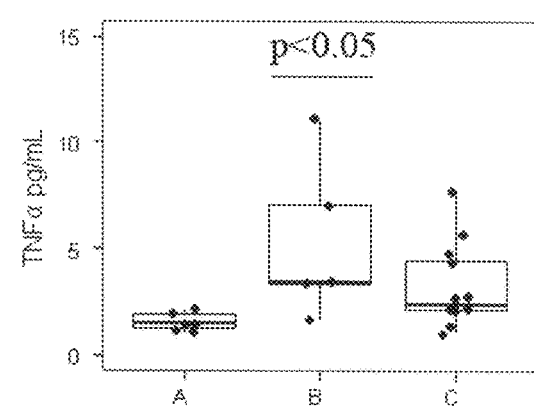
FIG. 3B shows concentrations of TNFα.
Figure 3C:
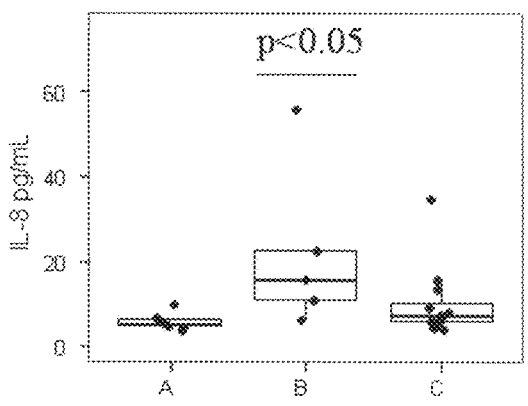
FIG. 3C shows concentrations of IL-8.
Figure 3D:
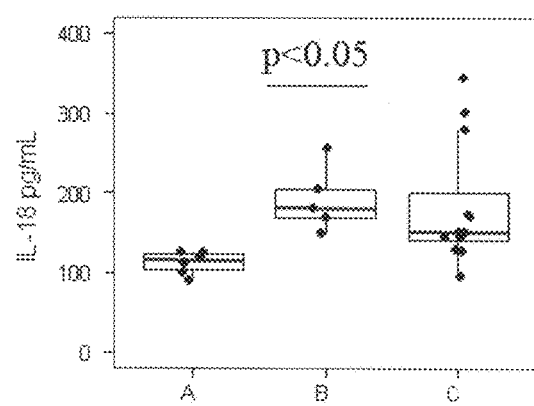
FIG. 3D show concentrations of IL-18, for lupus patients in groups A, B and C, defined based on clustering analysis of gene expression data. The vertical line indicates a significant difference (p<0.05) compared to other groups based on linear mixed model. Average levels from all visits were calculated for each patient in the study for data visualization and shown as black dots.

Inflammatory biomarker data were compared in the patient groups defined by gene expression analysis. Patients in group B showed a higher level of tumor necrosis factor α (TNF α), IL-8 and IL-18. (p<0.05 for all) (FIGS. 3B, C, and D).

The data herein demonstrated that three distinct groups of patients, defined by gene expression analysis of multiple patient peripheral blood and plasma samples collected over time, were associated with distinct autoantibody and cytokines profile in serum samples. Patients with the presence of IFIG and neutrophil-related signature were associated with higher plasma levels of TNFα, IL-8 and IL-18. Patients with neutrophil granule signature were associated with a high level of anti-SSA/Ro autoantibodies.

TABLE 10

Autoantibodies and plasma factors differentially expressed between SLE patients and healthy donors (minimum fold change 1.5; p < 0.05).

| Analyte | Fold Change | HD vs SLE Estimates | HD vs SLE p-values | Flare Estimates | Flare p-values |
|---|---|---|---|---|---|
| Autoantibodies | | | | | |
| Double Stranded DNA (ds DNA) Antibody# | 7.9 | 2.97 | 0.0037 | 0.86 | 0.0016 |
| SSA Antibody | 7.3 | 2.90 | 0.0166 | −0.22 | 0.2806 |
| RNP (c) Antibody# | 2.9 | 1.43 | 0.1136 | 0.65 | 0.0016 |
| Histone Antibody# | 1.5 | 0.49 | 0.1939 | 0.83 | 0.0000 |
| Histone H2b Antibody# | 1.5 | 0.46 | 0.0971 | 0.61 | 0.0016 |
| Plasma factors (inflammatory biomarkers) | | | | | |
| Prolactin | 3.6 | 1.90 | 0.0004 | −0.23 | 0.7343 |
| B-Lymphocyte Chemoattractant (BLC) | 3.2 | 1.71 | 0.0117 | 0.36 | 0.1030 |
| IL-10# | 2.5 | 1.26 | 0.0003 | 0.99 | 0.0002 |
| IP-10 (Inducible Protein-10)# | 2.4 | 1.46 | 0.0020 | 0.54 | 0.0212 |
| MIP-3b | 2.3 | 1.14 | 0.0050 | 0.15 | 0.5961 |
| TNF RII# | 2.0 | 0.96 | 0.0084 | 0.85 | 0.0000 |
| MIP-1beta | 2.0 | 0.91 | 0.0248 | 0.12 | 0.8073 |
| TNF-alpha# | 2.0 | 0.91 | 0.0248 | 0.78 | 0.0209 |
| IL-8# | 1.9 | 0.86 | 0.0272 | 0.93 | 0.0457 |
| BAFF | 1.8 | 0.81 | 0.0084 | 0.16 | 0.7343 |
| C Reactive Protein# | 1.7 | 0.49 | 0.5629 | 3.77 | 0.0000 |
| Beta-2 Microglobulin# | 1.7 | 0.68 | 0.0268 | 0.48 | 0.0000 |
| IL-18# | 1.6 | 0.69 | 0.0125 | 0.72 | 0.0002 |
| IL-6# | 1.6 | 0.66 | 0.0084 | 0.56 | 0.0212 |
| MCP-2 | 1.5 | 0.85 | 0.0188 | 0.23 | 0.3031 |
| von Willebrand Factor# | 1.5 | 0.43 | 0.1904 | 1.10 | 0.0000 |
| IL-23# | 1.5 | 0.47 | 0.2282 | −0.67 | 0.0406 |
| Eotaxin# | 0.6 | −0.38 | 0.5629 | −0.77 | 0.0002 |
| Ferritin# | 0.4 | −1.44 | 0.0855 | 2.41 | 0.0000 |

The effect of disease and flare on the level of autoantibodies is illustrated by fold increase and 5% FDR with corrected p-values.
identifies those autoantibodies and plasma factors that showed a significant effect from flares.

Example 4

Cross-Sectional Evaluation of PBMC Profiles in SLE Patients

Figure 4:
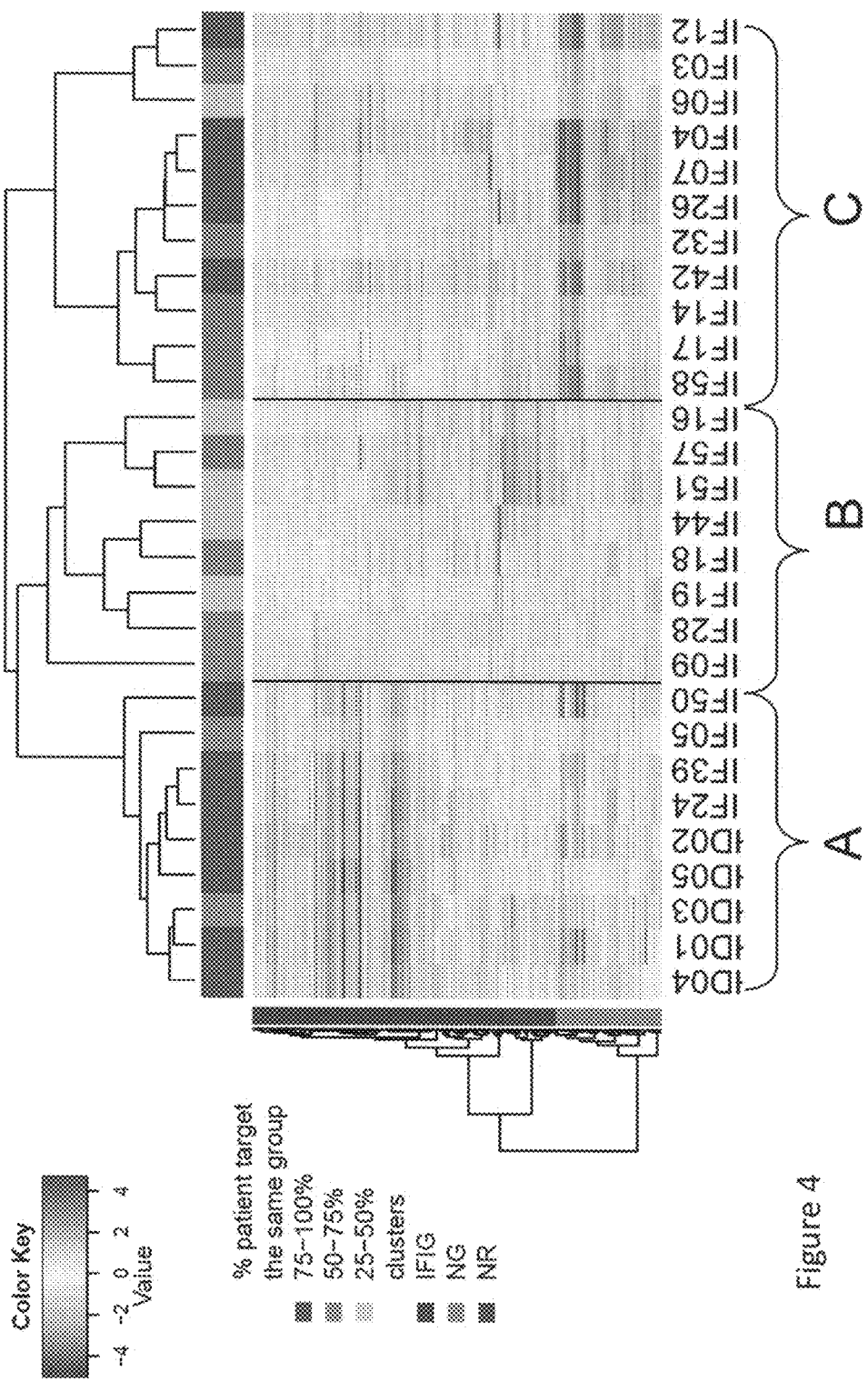
FIG. 4 is a heatmap and dendrogram showing the hierarchical clustering of SLE patients based on transcripts, selected as related to IFIG, neutrophil granule and neutrophil related signatures. The dendrogram depicts subjects (shown in columns) classified based on 195 mRNA transcripts, identified as interferon inducible genes, neutrophil-granules related and neutrophil-related genes (shown in the rows). The attached color code on top of heatmap illustrates how often individual subject target the same group when clustering was performed 500 times, each time selecting unique combination of visits. Deeper red color indicates stable position in selected group.

A new unsupervised hierarchical clustering was performed based on transcripts assigned to the top 3 clusters: IFIG, neutrophil granules and neutrophil related signatures and obtained similar classification of SLE patients (groups A, B and C) as shown in the dendrogram (FIG. 4). Based on linear mixed model the majority of those transcripts remain upregulated even during non-flaring visits, meaning that it is likely that cross-sectional analysis would also classify SLE patient into similar group. To evaluate this hypothesis, hierarchical clustering was performed 500 times, each time selecting a random visit for each patient. The attached color code in FIG. 4 indicates how often particular subject remained in the same group when the data from random visits were used instead of taking an average. It was clear that the majority of patients from category A and C remain in the same branches of dendrogram irrespective of visit. Patients from group B were less stable and more often were misclassified. However overall it remained possible to classify patients based on a single visit.

Figure 5:
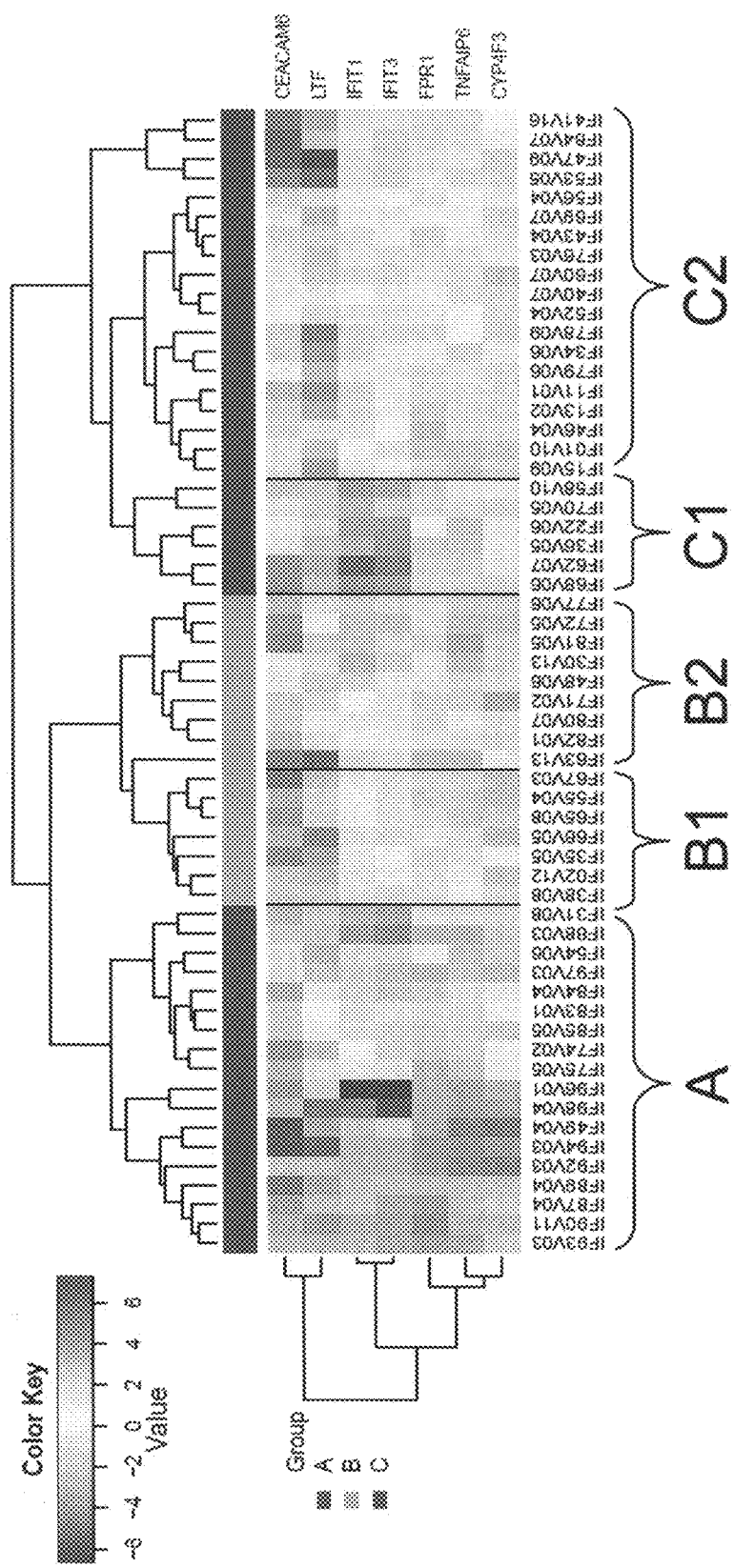
FIG. 5 is a heatmap and dendrograms that illustrate the classification of a validation set of 59 SLE patients. Level of mRNA transcripts was measured by quantitative real time PCR. Seven genes (in the rows), representing interferon inducible signature genes, neutrophil granule signature genes and neutrophil-related signature genes were chosen to classify SLE patients (in the columns). Three major groups of SLE patients A, B, and C, and five subgroups (A, B1, B2, C1, and C2) were observed.
Figure 6A:
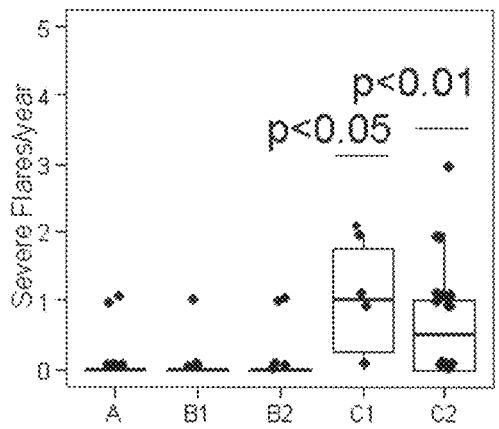
FIG. 6A shows frequency of severe flares.
Figure 6B:
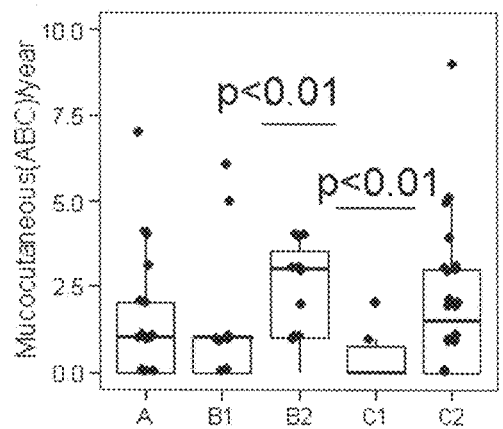
FIG. 6B shows frequency of visits with active mucocutaneus involvement.
Figure 6C:
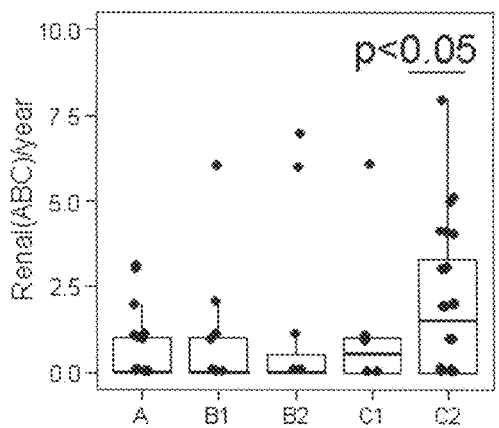
FIG. 6C shows frequency of visits with active renal involvement.
Figure 6D:
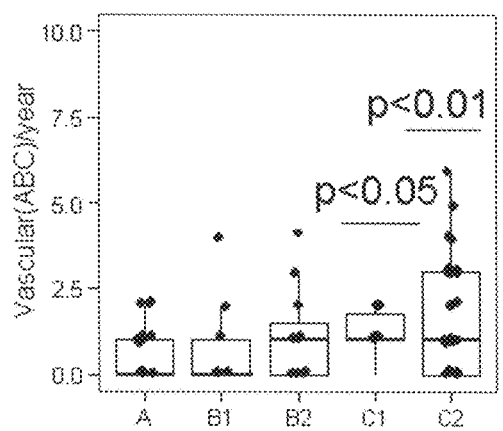
FIG. 6D shows frequency of visits with vascular involvement, based on BILAG score.

Quantitative real time PCR(RT-PCR) analysis was performed for an additional set of 59 SLE patients. Seven genes were chosen from top three clusters; IFIT1 and IFIT3 represented IFIG signature, CEACAM6 and LTF represented neutrophil granules signature and TNFAIP6, CYP4F3 and FPR1 represented neutrophil related signature. Level of HPRT1 remained constant in peripheral blood of SLE patients based on microarray data and it was chosen as housekeeping gene. See FIG. 5.

Based on results of RT-PCR, SLE patients were classified to similar groups A, B and C, according to unsupervised hierarchical clustering: group A lacked either signature; group B showed IFIG signature, but lacked neutrophil granules signature; and group C showed prominent neutrophil granules signature.

As more samples were studied further classifications could be made. Group B could be subdivided in two groups, B1 and B2, based on absence or presence of neutrophil related signature. Group C could also be subdivided into two groups, C1 and C2, based on the absence or presence of IFIG signature. Among the 59 SLE patients used for validation a new visit of patient IF58, which was from our initial set of patients, were used to confirm the absence of IFIT1 and IFIT3 expression for that patient.

In summary, classification of SLE patients based on the IFIG, neutrophil-granules and neutrophil related signatures subdivides SLE patient in 5 groups.

Example 5

Clinical Characteristics of Defined SLE Patient's Groups

It was hypothesized that classification of SLE patients based on hierarchical clustering of mRNA data might reflect distinct clinical phenotypes.

Demographic data for five groups of SLE patients were summarized in Table 11. In general, the prevalence of SLE is far higher in females than in males. In our study 11 out of 81 patients were males and male/female ratio was close to the frequently reported ratio of 1:9. Unexpectedly, the distribution of male patients among groups was biased with significant prevalence of male patients in group C1 (OR 5.6, 95% CI (1.5-41), p<0.03). Groups A and B1 have minor proportion of male cases. Interestingly, patients from group B1 were significantly older at the first visit (median age 41 years (range 19-52 years p<0.04), and preferentially European Americans (4 out of 6, OR 3.4 95% CI (1.0-17), p=0.05). No other difference in patient's demographic was observed.

Major clinical characteristics for SLE patients, including ACR criteria for SLE, flare status, components of SLEDAI and BILAG scores, were collected longitudinally for each patient visits. ACR score and ACR criteria for the last follow visit for each patient was compared among groups (Table 12). There was no difference in ACR score between groups. However, no patients from group C 1 developed photosensitivity, in contrast to other groups (OR 0.1 95% CI (0-2.0) p<0.05). There were patients from group B1 and C2 whom developed photosensitivity more often (non-significant). Patients from group C 1 were more prone to develop neurological disorders (non-significant). At the same time, there were no cases of discoid disorders among patients from group B2 and C 1 (non-significant). Group B2 also showed higher incidence of serositis disorders (OR 2.8 (1.0-10) p<0.05). ACR criteria for renal disorders, which represent one of the major challenges for lupus patients, were detected among patients from group C1 and C2.

The most illustrative parameter of disease activity is lupus flare. In order to evaluate parameters, such as flares, which vary over the time, a generalized linear mixed model as described in Example 1 was used. Based on SELENA/SLEDAI index, flares can be categorized to severe and mild/moderate. The rate of total, severe and mild/moderate flares per year for each category was compared first. Patients from group B1 and C2 developed an average of 1.9 (1.3-2.8) flares/year, and 1.6 (1.2-2.4) flares/year, respectively. That was significantly higher (p<0.03 and p<0.01, respectively) in comparison to that of group A which had 1.1 (0.8-1.5) flares/year. With regard to severe flare occurrences, the highest rate of severe flares was for groups C1 (0.6 (0.2-1.6) flares/year) and C2 (0.6 (0.3-1.4) flares/year). That was significantly higher rate (p<0.03 and p<0.01, respectively) in comparison with group A (0.2 flares/year).

SLEDAI is a useful instrument to evaluate disease activity over time. In this study SLEDAI score tended to be higher in groups B2 and C2, without reaching significance. BILAG score is an organ specific index, based upon the physician's intention to treat the patient, which scores SLE disease activity in eight organ-based systems (American College of Rheumatology Ad Hoc Committee on Systemic Lupus Erythematosus Response Criteria 2004). BILAG scores were significantly higher among SLE patients from group C2 (4 (4.5-7.6), p<0.02).

Subsequently, the statistical analysis was focused on components of the BILAG score. The rate of visits of patients with BILAG score A, B and C per year, were calculated. The grades A, B and C of BILAG score indicate current involvement of a system in pathological process. Based on components of B1LAG score, it was observed that patients from group B2, who showed prominent IFIG and neutrophil-related gene signatures, were more prone to have mucocutaneous involvements (estimate 2.3 (1.6-3.3) visits/year, p<0.04). In contrast, patients from group C1, lacking IFIG signature, rarely display mucocutaneous involvement (estimate 0.4 (0.2-0.8) visits/year, p<0.01).

The next prominent difference was that patients with neutrophil granule gene signature, groups C1 and C2, were more prone to develop vascular involvements (estimate 1.3 (0.7-2.3) visits/year p<0.05 and 1.7 (1.1-2.6) visits/year p<0.01, respectively). Patients showing both neutrophil granule and IFIG gene signatures, group C2, were more prone to manifest renal flares by BILAG (estimate 1.5 (1-2.4) visits/year p<0.05). Groups B2 and C1, both displaying IFIG signatures, showed increase rate of general involvement (estimate 3.1 (2.3-4.2) p<0.01 and 2.6 (2-3.5) p<0.01 visits/year, respectively).

In summary, it was observed that patients from group C2 were more active and more often developed renal disease, which is a significant clinical challenge for SLE patients.

The fact that patients from group C2 were more active was further supported by the observation that the overall dose of prednisone over the last month was higher for this group compared to others (12.3 (9.2-15.6) mg/day p<0.01).

These data are summarized in Table 13. FIG. 6 shows a graphical representation of each group with regard to severe flares, and clinical manifestations, including mucocutaneous, renal, and vascular.

The results herein show that mRNA transcripts differentially expressed among patient groups A, B1, B2, C1 and C2 were not only associated with different degrees of disease activity and frequency of clinical flares, but might also identify distinct pathogenic mechanisms associated for instance with mucocutaneous versus vascular involvement.

The results of laboratory blood tests collected longitudinally for the majority of the patients were also compared. Group C2 of SLE patients, in accordance with their clinical manifestations, showed non-significant increase in erythrocytes sedimentation rate (ESR) (35.8 mm/h (31.1-40.4) N/S) and C-reactive protein concentration (CRP) (1.3 mg/dL (1-1.5) N/S). Compared to other groups, significant decrease in lymphocytes count ((ALC) for group C2 was observed (1.12/pt (0.98-1.25) p<0.02). Level of complement C3 was also low in group A (84 mg/dL (78-91), N/S), whereas group B1 had significantly higher level of C3 compared to other groups (96 mg/dL (87-106) p<0.02). SLE patients, from group C1, where male prevalence was noted, had the lowest erythrocytes sedimentation rate (13.4 mm/h (3.8-23.4) p<0.01), and at the same time showed increased neutrophil counts (ANC) in peripheral blood (5.67/μL (4.64-6.69) p<0.02). These results are summarized in Table 14.

Figure 7:
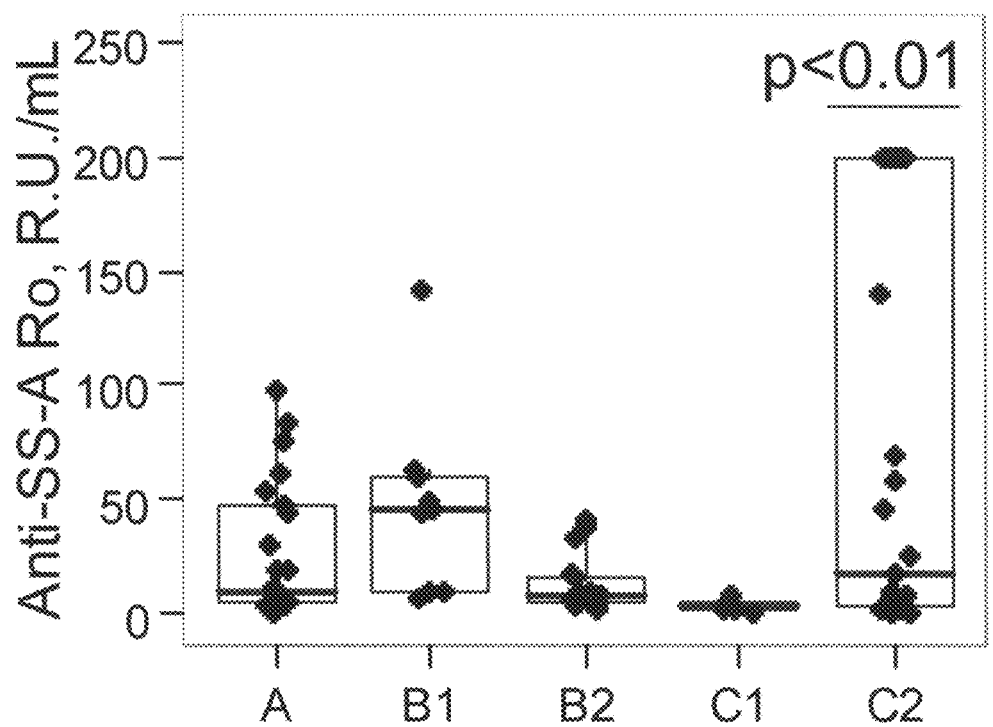
FIG. 7 is a graph depicting the amount of anti-SS-A (Ro60) antibody in plasma samples of the various groups of SLE patients as measured by ELISA. The concentration higher than upper detection limit was considered as 200 R.U./mL. $p<0.01$.

The classification of SLE patients based on the selected IFIG, neutrophil-granules and neutrophil related genes was capable of sub-dividing SLE patient in groups, with distinct clinical, laboratory and demographic association. In general, SLE patients from group A and B1 received less doses of prednisone in the course of their disease as compared to other groups (5.6 (3-8) mg/day and 5.8 (1.6-10.4) mg/day, respectively), while SLE patients from group C2 received significantly higher doses (12.3 (9.2-15.6) mg/day p<0.01) (Table 13). Moreover, patients from group C2 were more prone to develop flares (including severe flares). Those, along with BILAG score and rate of renal involvement, indicated that group C2 of SLE patients was associated with a more dangerous course of disease. That group was also associated with higher levels of anti-SS-A(Ro) autoantibody (FIG. 7). Although groups B2 and C1 of SLE patients were less active than group C2, those patients remain under the higher risk compared to groups A1 and B1. Interestingly the pathological mechanism among the groups was also different, as groups C1 and C2 were more prone to vascular involvements, while groups B1 and B2 were more prone to mucocutaneus disorders. See Table 13.

TABLE 11

Demographic characteristics obtained for groups of SLE patients (A, B1, B2, C1, C2)

|  | A | B1 | B2 | C1 | C2 |
| --- | --- | --- | --- | --- | --- |
| Total | 22 | 9 | 15 | 6 | 29 |
| Sex Male | 1 | 0 | 3 | 3 | 4 |
| (%) | (5%) | (0%) | (20%) | (50%)* | (14%) |
| p-value |  |  |  | 0.03 |  |
| Age, years | 25.5 | 41 | 28 | 29.5 | 28 |
| (range) | (14-57) | (19-52)* | (17-50) | (25-43) | (17-49) |
|  |  | 0.036 |  |  |  |
| Disease duration, | 4.5 | 4 | 3 | 6 | 3 |
| years | (0-24) | (0-11) | (0-19) | (0-16) | (0-23) |
| (range) |  |  |  |  |  |
| Asian Americans | 2 | 1 | 1 | 1 | 2 |
| (%) | (9%) | (11%) | (7%) | (17%) | (7%) |
| Black Americans | 9 | 1 | 4 | 2 | 14 |
| (%) | (41%) | (11%) | (27%) | (33%) | (48%) |
| European Americans | 5 | 4 | 2 | 2 | 2 |
| (%) | (23%) | (44%)* | (13%) | (33%) | (7%) |
| p-value |  | 0.06 |  |  | 0.07 |
| Hispanic Americans | 5 | 2 | 8 | 1 | 11 |
| (%) | (23%) | (22%) | (53%) | (17%) | (38%) |
| Other | 1 | 1 | 0 | 0 | 0 |
| (%) | (5%) | (11%) | (0%) | (0%) | (0%) |

Note:
Confidence intervals and p-values were obtained for categorical data using odds ratio test for small samples. Confidence intervals and p-values for continuous parameter such as age, was calculated using generalized linear model (see details in methods). Significantly different parameters were bolded and labeled with asterisk mark.

TABLE 12

Average ACR score and number of individuals correspond to ACR criteria for groups of SLE patients (A, B1, B2, C1, C2)

|  | A | B1 | B2 | C1 | C2 |
| --- | --- | --- | --- | --- | --- |
| ACR score, | 6 | 6 | 6 | 5 | 6 |
| (range) | (3-9) | (3-7) | (2-9) | (4-6) | (2-9) |
| Malar Rash, | 13 | 4 | 9 | 2 | 16 |
| (%) | (59%) | (44%) | (60%) | (33%) | (55%) |
| Discoid Rash, | 3 | 2 | 0 | 0 | 6 |
| (%) | (14%) | (22%) | (0%) | (0%) | (21%) |
| Photosensitivity, | 6 | 5 | 5 | 0 | 15 |
| (%) | (27%) | (56%) | (33%) | (0%) | (52%) |
| p-value |  |  |  | 0.05 |  |
| Oral Ulcers, | 8 | 2 | 5 | 2 | 10 |
| (%) | (36%) | (22%) | (33%) | (33%) | (34%) |
| Arthritis, | 21 | 8 | 13 | 5 | 24 |
| (%) | (95%) | (89%) | (87%) | (83%) | (83%) |
| Serositis, | 9 | 2 | 10 | 1 | 12 |
| (%) | (41%) | (22%) | (67%) | (17%) | (41%) |
|  |  |  | 0.04 |  |  |
| Renal Disorder, | 8 | 4 | 6 | 4 | 18 |
| (%) | (36%) | (44%) | (40%) | (67%) | (62%) |
| Neurological disorder, | 2 | 1 | 4 | 2 | 6 |
| (%) | (9%) | (11%) | (27%) | (33%) | (21%) |
| Hematologic disorder, | 18 | 6 | 10 | 3 | 21 |
| (%) | (82%) | (67%) | (67%) | (50%) | (72%) |

TABLE 12-continued

Average ACR score and number of individuals correspond to
ACR criteria for groups of SLE patients (A, B1, B2, C1, C2)

|  | A | B1 | B2 | C1 | C2 |
|---|---|---|---|---|---|
| Immunologic disorder, (%) | 21 (95%) | 6 (67%) | 12 (80%) | 5 (83%) | 24 (83%) |
| ANA (%) | 22 (100%) | 9 (100%) | 15 (100%) | 6 (100%) | 28 (97%) |

Note:
p-values were obtained for categorical data using odds ratio test for small samples.
ANA - indicates positive for antinuclear autoantibodies test.

TABLE 13

Estimated SLEDAI and BILAG scores and estimated rates of visits/year when flares or systemic involvement occur

| Estimates (95% CI), p-value | A | B1 | B2 | C1 | C2 |
|---|---|---|---|---|---|
| Flares/year | 1.1 (0.8-1.5) | 1.1 (0.6-1.8) | 1.9 (1.3-2.8) | 1.3 (0.8-2.2) | 1.7 (1.2-2.4)* 0.0261 |
| Severe Flares/year | 0.2 (0.1-0.4) | 0.2 (0.1-0.6) | 0.2 (0.1-0.5) | 0.6 (0.2-1.6)* 0.0296 | 0.6 (0.3-1.4)* 0.0036 |
| SLEDAI | 3.2 (2.4-3.9) | 3.4 (2.5-5.9) | 4.1 (3.8-7.5) | 2.9 (1.5-4.3) | 3.7 (3.1-5.8) |
| BILAG | 2.7 (2.1-3.4) | 2.9 (2.1-4.8) | 3.1 (2.6-5.2) | 2.6 (1.4-3.9) | 4 (4.5-7.6)* 0.0078 |
| General/year | 1.8 (1.4-2.2) | 2.2 (1.5-3.1) | 3.1 (2.3-4.2)* 0.0004 | 1.4 (0.9-2.3) | 2.6 (2-3.5)* 0.0046 |
| Mucocutaneous/year | 1.3 (1-1.7) | 1.9 (1.3-2.9) | 2.3 (1.6-3.3)* 0.0026 | 0.4 (0.2-0.8)* 0.0047 | 1.4 (1-2) |
| Neurological/year | 0.2 (0.1-0.3) | 0.6 (0.2-1.7) | 0.8 (0.4-2.2) | 0.9 (0.4-2.6) | 0.6 (0.3-1.6) |
| Muskoskeletal/year | 2.2 (1.8-2.7) | 1.7 (1.1-2.5) | 2.7 (2-3.7) | 1.2 (0.7-2)* 0.0244 | 2 (1.5-2.6) |
| Cardiac/year | 0.6 (0.4-0.9) | 0.2 (0.1-0.5) | 0.6 (0.4-1.1) | 0.1 (0-0.3) | 0.4 (0.2-0.6) |
| Vascular/year | 0.7 (0.5-1) | 0.9 (0.5-1.6) | 1.1 (0.6-1.7) | 1.3 (0.7-2.3)* 0.0394 | 1.7 (1.1-2.6)* 0.0001 |
| Renal/year | 0.5 (0.3-0.8) | 1.3 (0.7-2.3) | 1.2 (0.7-2.1) | 1 (0.5-1.9) | 1.5 (1-2.4)* 0.05 |
| Hemotological/year | 1.7 (1.4-2.2) | 1.1 (0.7-1.8) | 1.3 (0.9-1.9) | 1.2 (0.7-2) | 2.1 (1.6-2.8) |
| Prednisone mg/day | 5.6 (3-8) | 5.8 (1.6-10.4) | 8.9 (5.4-12.8) | 6.6 (1.7-11.5) | 12.3 (9.2-15.6)* 0.001 |

Note:
Flares and Severe flares were determined using SELENA/SLEDAI instruments.
SLEDAI—SLE disease activity index 2000;
BILAG—British Isles Lupus Assessment Group 2000 index;
BILAG score accounts disease activity in eight systems.
Disease activity in particular system was considered positive for BILAG equal A, B and C. Estimate indicates average rate of visits per year.
The corresponding p-value indicates level of significance in comparison to group A.

TABLE 14

Major laboratory findings for groups of SLE patients (A, B1, B2, C1, C2).

| Estimate (95% CI), p-value | A | B1 | B2 | C1 | C2 |
|---|---|---|---|---|---|
| C3 mg/dL | 84 (78-91) | 96 (87-106)* 0.02 | 88 (81-95) | 94 (83-105) | 86 (81-91) |
| C4 mg/dL | 18.9 (16.5-21.4) | 18.1 (14.2-21.8) | 16.1 (13.4-18.9) | 16.8 (12.2-21.3) | 18.4 (16.3-20.3) |
| ESR mm/hr | 22 (16.4-27.7) | 27.6 (18.1-37.2) | 20.9 (14.6-27.4) | 13.4 (3.8-23.4) 0.0002 | 35.8 (31.1-40.4) |
| CRP mg/dL | 1 (0.7-1.3) | 0.8 (0.2-1.4) | 0.7 (0.5-1.1) | 1 (0.5-1.5) | 1.3 (1-1.5) |

TABLE 14-continued

Major laboratory findings for groups of SLE patients (A, B1, B2, C1, C2).

| Estimate (95% CI), p-value | A | B1 | B2 | C1 | C2 |
|---|---|---|---|---|---|
| HB mg/dL | 12 (11.7-12.4) | 12.3 (11.8-12.8) | 12.1 (11.7-12.5) | 12.5 (11.9-13.2) | 11.8 (11.6-12.1) |
| WBC/uL | 6.2 (5.4-7) | 6.5 (5.2-7.7) | 5.7 (4.8-6.7) | 7.6 (6.1-9) | 6.1 (5.5-6.8) |
| ANC/uL | 4.18 (3.61-4.75) | 4.49 (3.56-5.33) | 4.22 (3.58-4.88) | 5.67 (4.64-6.69)* 0.014 | 4.46 (3.99-4.92) |
| ALC/uL | 1.38 (1.21-1.54) | 1.22 (0.97-1.46) | 1.17 (0.98-1.35) | 1.32 (1.02-1.6) | 1.12 (0.98-1.25)* 0.0144 |
| PLT/uL | 0.27 (0.25-0.29) | 0.3 (0.27-0.33) | 0.29 (0.27-0.31) | 0.24 (0.2-0.28) | 0.27 (0.25-0.29) |

Note:
Estimates, confidence intervals and p-values were obtained based on linear mixed model followed by Markov chain Monte Carlo methods for detecting p values.

Example 6

Biomarkers for Lupus Disease Activity

Using K-means clustering of the microarray data in Example 1, twenty-five of the most significant clusters with the greatest level of variance over time were selected.

Using the generalized linear mixed model analysis described in Example 1, the best combination of transcript signatures was identified as the interferon, plasma cell, neutrophil related, and neutrophil granule (Table 15).

Representative gene transcripts from various clusters were chosen to verify this correlation. Select genes from a cluster can reflect the entire cluster in relation to disease activity. The criteria for the selection of the gene transcripts was:
1. Each component of score (probe set) should be expressed at a high level and represent functional characteristics of the cluster.
2. The obtained score should reflect SLEDAI score (Spearman correlation).
3. The obtained score should coincide with severe flare ($p<0.01$) and show decrease after severe flare.

Using these criteria and the results of generalized linear mixed effects model between the clusters and SLEDAI set forth in Table 15, four genes from four different clusters were chosen for further microarray analysis: IFIT3 from C08, KLRB1 form C10, CD38 from C27, and MMP8 from C49.

TABLE 15

Relationship between SLEDAI and Gene Clusters

| Cluster # | Cluster Name | Number of genes | t-value | p-value |
|---|---|---|---|---|
| C17 | Neutrophil-related genes | 23 | 4.24 | ..0001 |
| C10 | T-cells/iNKT genes | 20 | -3.42 | 0.0009 |
| C49 | Neutrophil granule genes | 24 | 3.37 | 0.0010 |
| C08 | IFIG | 83 | 2.99 | 0.0033 |
| C27 | Immunoglobulin/plasma cell genes | 45 | 1.93 | 0.0561 |

Figure 8:
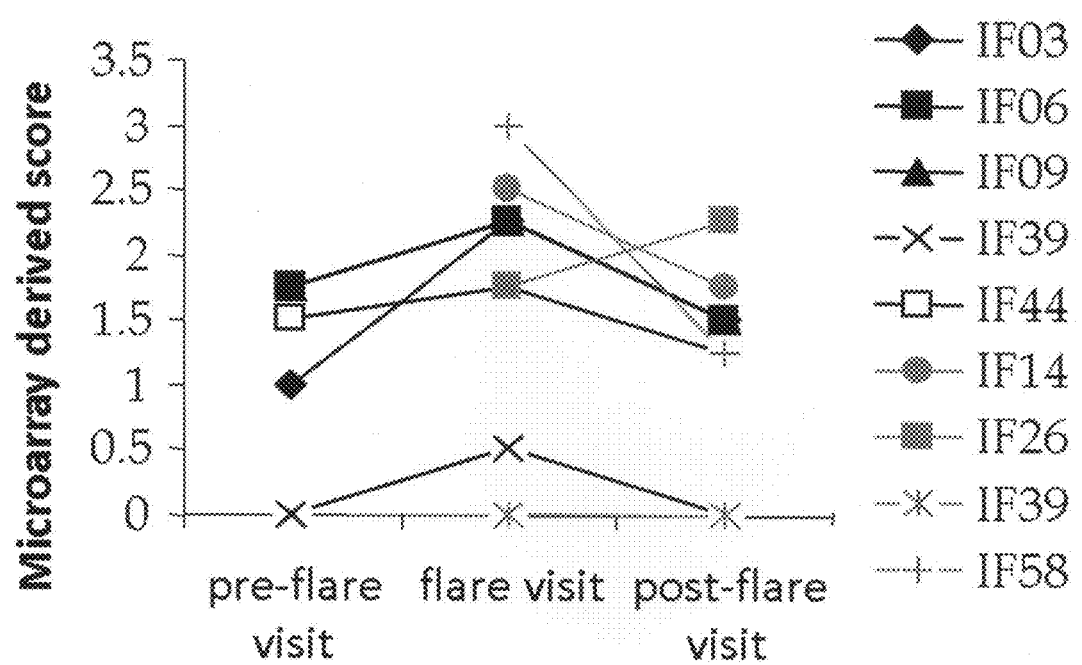
FIG. 8 is graph depicting results of the 4-gene microarray score for nine patients (denoted with IF#) at a mean of 100 days before flare ($p=<0.02$), at flare visit and a mean of 100 days after flare visit ($p=<0.02$).
Figure 9A:
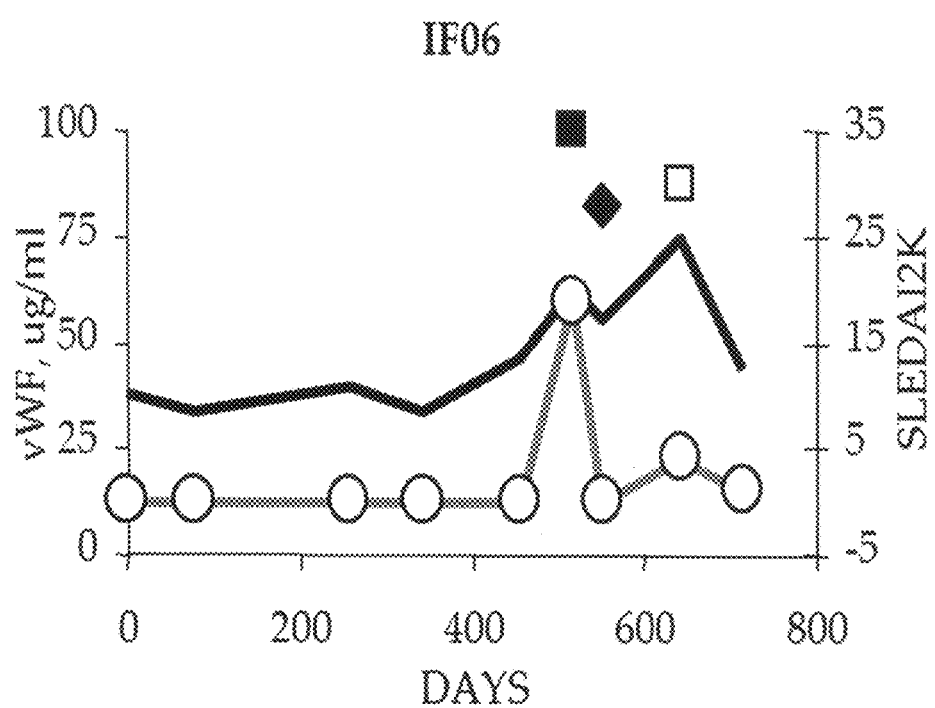
FIGS. 9A, 9B, and 9C (IF06, IF09, and IF12 respectively) are the results of measurement of vWF in µg/ml versus days are shown in solid black lines.
Figure 9B:
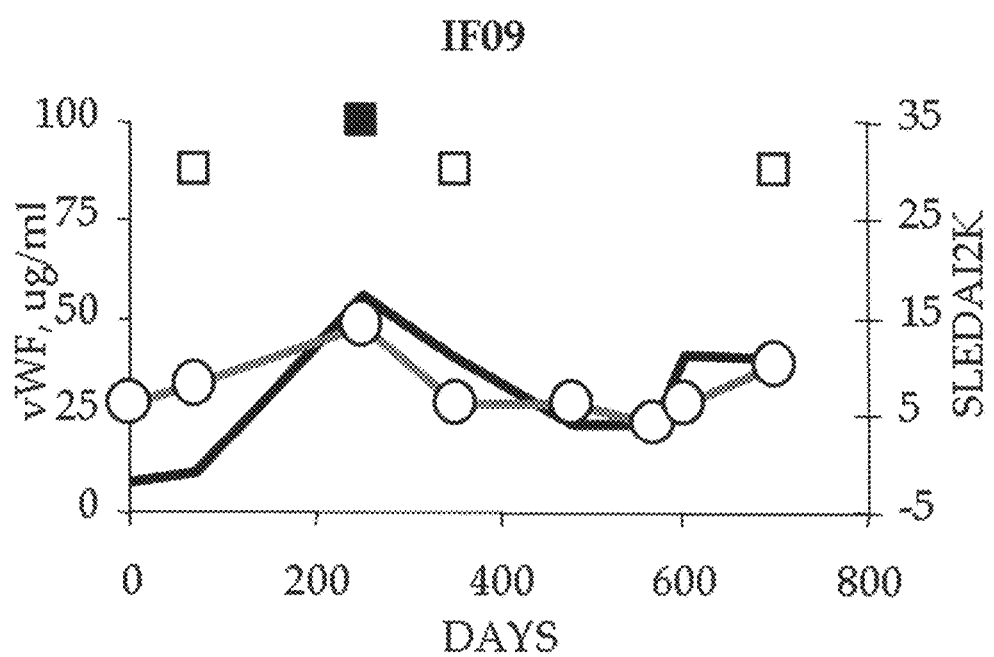
Figure 9C:
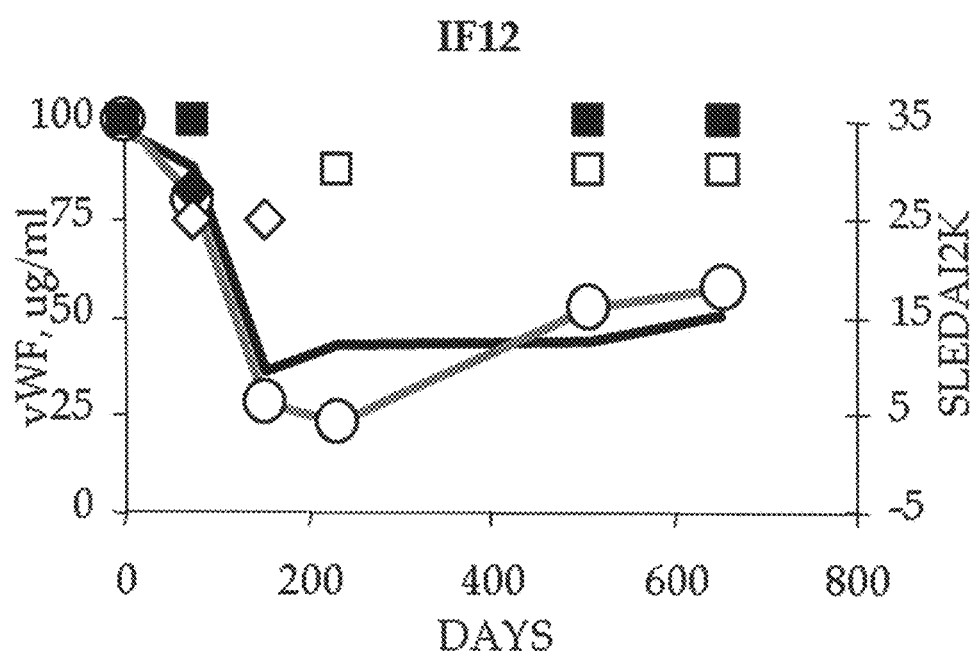
Figure 9D:
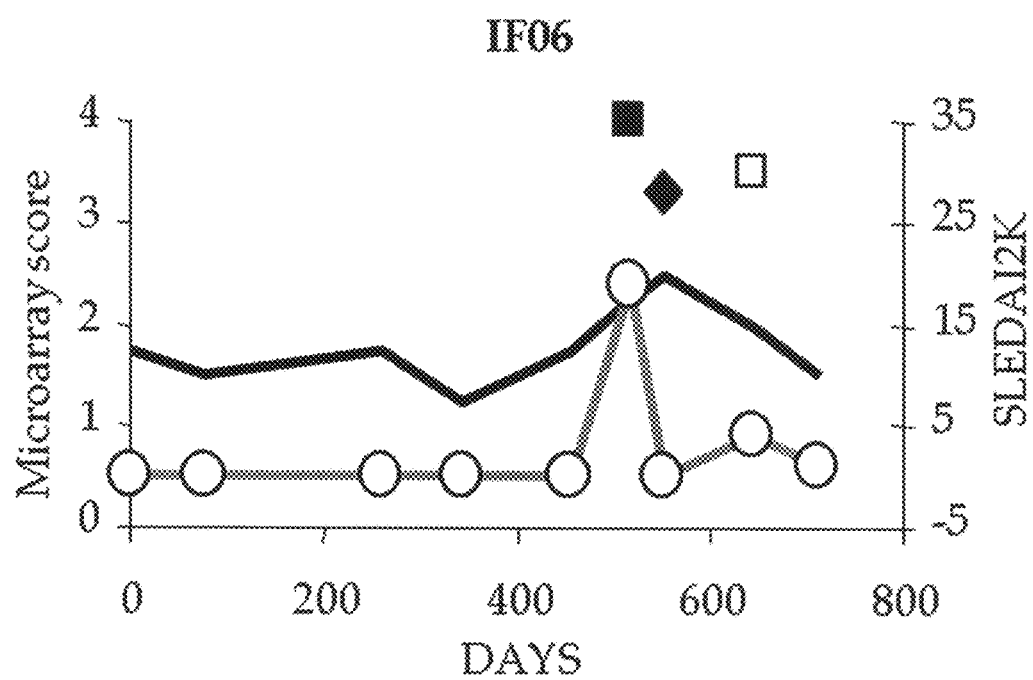
FIGS. 9D, 9E, and 9F (IF06, IF09, and IF12 respectively) are the 4-gene microarray scores versus days as shown in solid black lines. In all six figures, the SLEDAI 2K score is shown in open circles connected by black lines, black solid squares denote severe flares, black solid diamonds denote pulse glucocorticoids, and open diamonds denote Cytoxan.
Figure 9E:
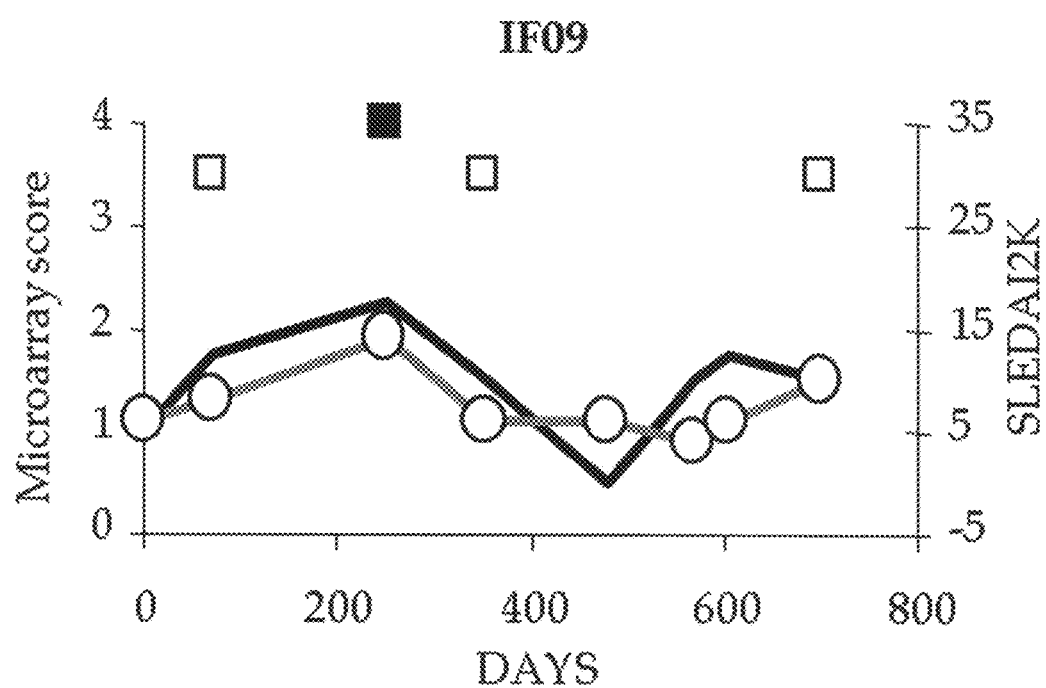
Figure 9F:
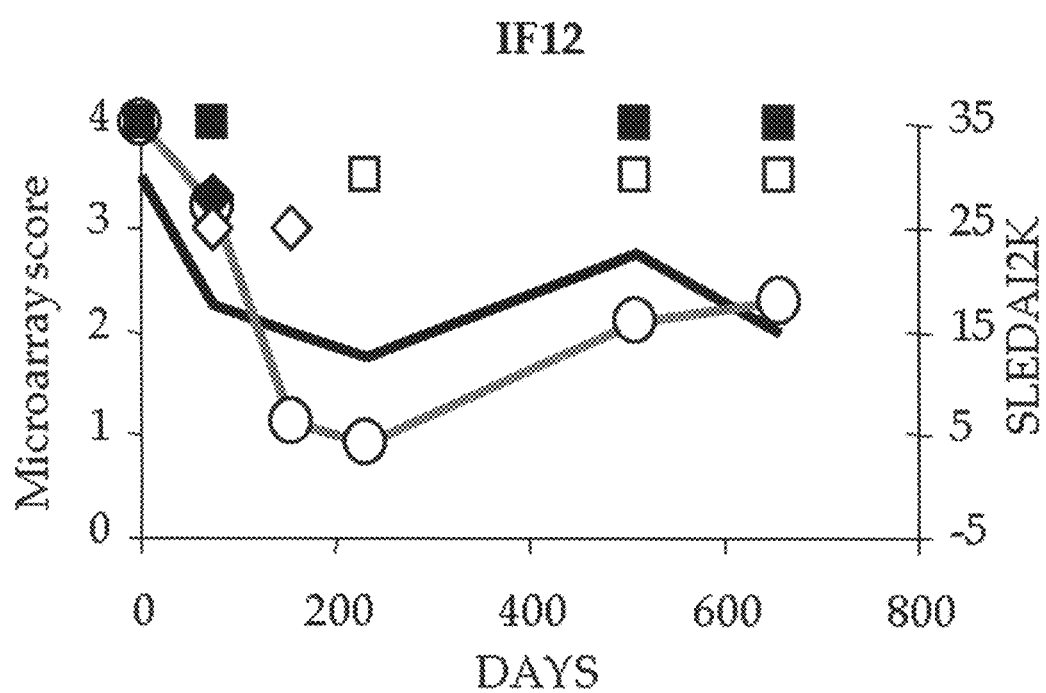

As shown in FIG. 8, the 4-gene microarray score for ten SLE patients increased during flare visits.

Next using the generalized linear mixed model analysis of the plasma analytes in Table 10 four were identified that were significantly different between SLE and healthy controls. These were von Willebrand factor (vWF), Eotaxin, IL-10, and anti-Ro antibody.

Using Pearson correlation, vWF showed the highest level of significance when relating levels of all patient visits to SLEDAI score (R=0.5). Moreover, paired t-test analysis showed a consistent increase in the level of vWF during severe flare ($p<0.02$, mean fold change 1.6x) as compared to both the first non-flaring visit before and the first non-flaring visit after. In generalized linear mixed model analysis for correlation of plasma factors with SLEDAI score, vWF gave the strongest correlation with SLEDAI. Only vWF was significantly higher at the time of flare as compared to non-flare visits.

The level of vWF in plasma was correlated with the 4-gene score. As shown by FIG. 9, level of vWF in plasma was significantly correlated with 4-gene score. FIG. 9 shows representative examples of fluctuation of vWF (FIGS. 9A, B, C) and 4-gene microarray score (FIGS. 9D, E, F) in three selected SLE patients.

vWF is produced by endothelial cells and is required for normal hemostasis and vascular function. Levels of circulating vWF are increased following endothelial cell damage and during acute phase responses. The significantly increased level of vWF during lupus flare in the majority of SLE patients highlights the role of endothelial injury as a major pathogenic mechanism in SLE and identifies vWF as an informative biomarker for patient management and clinical studies.

Figure 10:
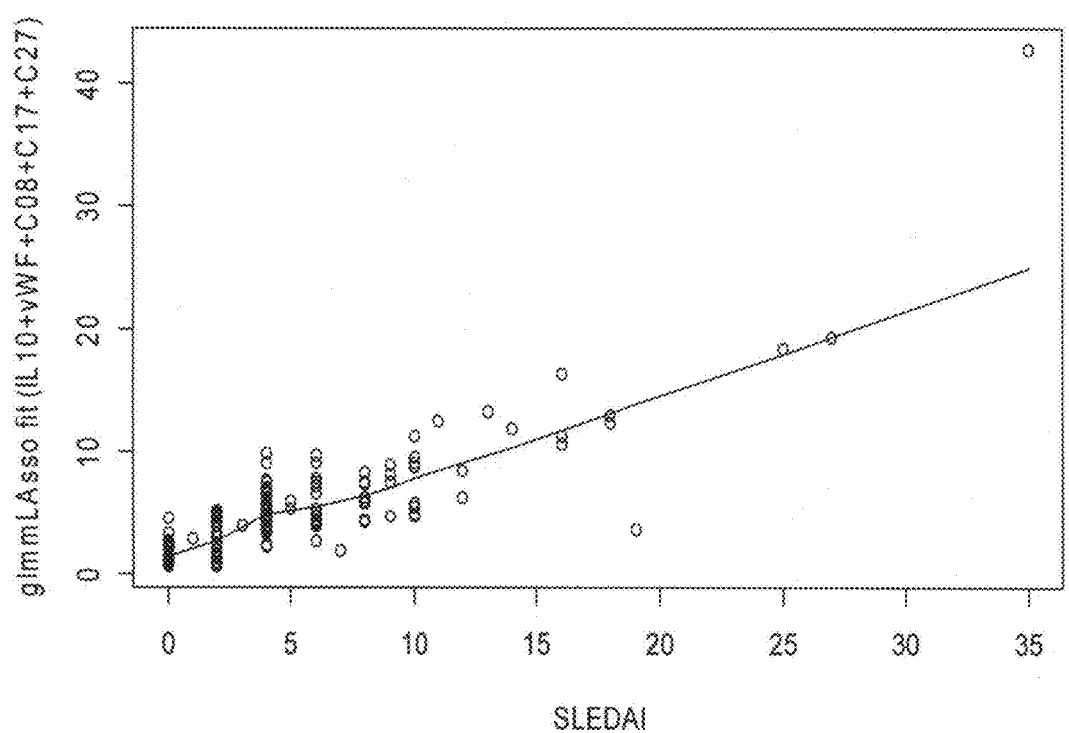
FIG. 10 is a graph depicting the best fit panel of biomarkers versus SLEDAI score, using generalized linear mixed model analysis.

When the transcripts and plasma analytes were combined, the five factors providing the best correlation with SLEDAI were von Willebrand factor, IL-10, interferon transcripts, plasma cell transcripts, and neutrophil granule transcripts. See FIG. 10.

Example 7

Biomarkers for Future Flare Activity

Using microarrays and statistical analysis as described in Example 1, and the 4-gene microarray described in Example 6, and the clinical characteristics described in Example 5, a correlation between gene expression and future flares was sought.

Participating SLE patients were divided into two groups according to 4-gene score level, with those defined as having a high score in the top 25th percentile and those defined as having a low score in the bottom 25th percentile. The score was determined at the first patient visit with a SLEDAI score <4 and identified as time 0. An increase of >3 in the SLEDAI score was considered as a flare event.

Based on the Kaplan-Meier plot, SLE patients with a high 4-gene score at time 0 were more likely to develop a flare during the follow-up visits than those with a low 4-gene score (estimated level of significance p<0.1 N/S).

The disease manifestations of these groups, as well as their number of SLEDAI2K>4 visits/year, average prednisone intake, and average C3 level is summarized in Table 16.

The difference between mean level of gene transcript expression between high and low flaring patients for all non-flaring visits greater than 100 days prior to or after a severe flare was determined.

Figure 11:
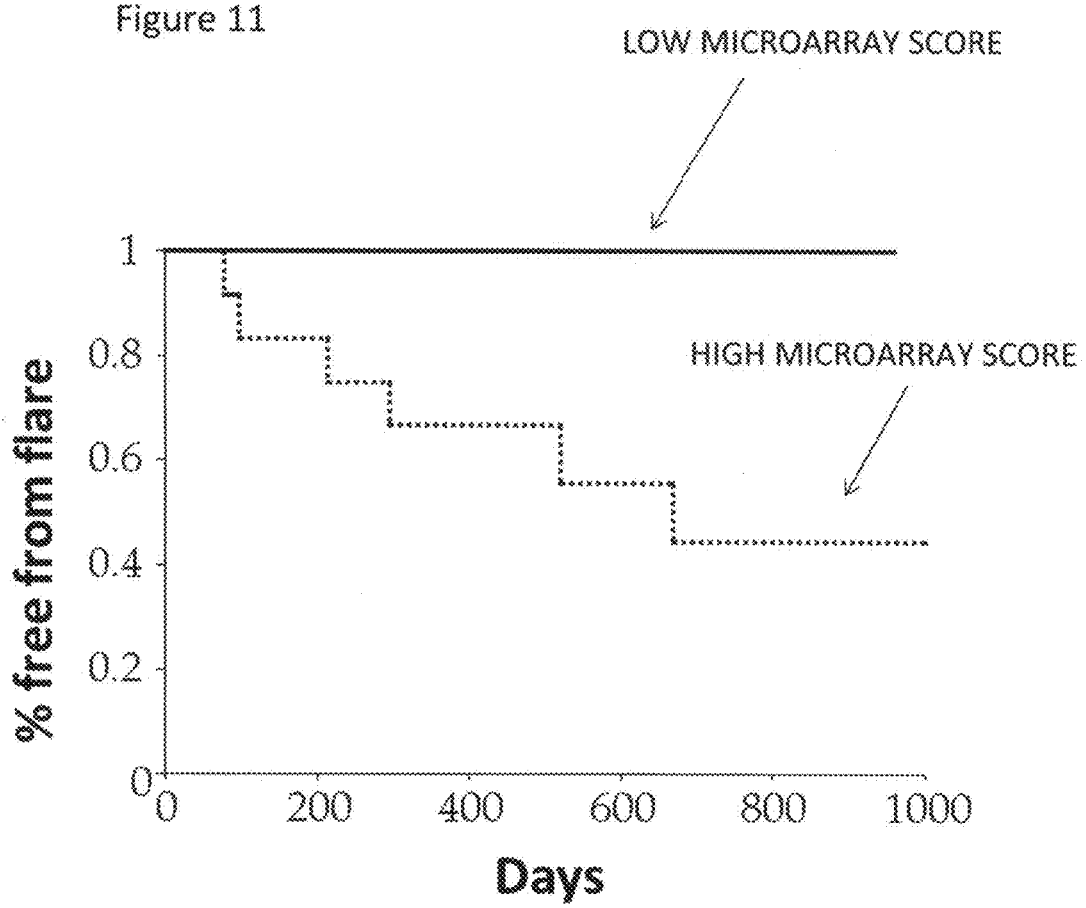
FIG. 11 is a graph showing the percentage free from flares versus days of patients with a low 4-gene microarray score at non-flaring visits and patients with a high 4-gene microarray score at non-flaring visits.

As shown in FIG. 11, patients with a low 4-gene score of genes comprising IFIT3, KLRB1, CD38, and MMP8 at non-flaring visits were significantly less likely to develop flares (p<0.01).

Figure 12:
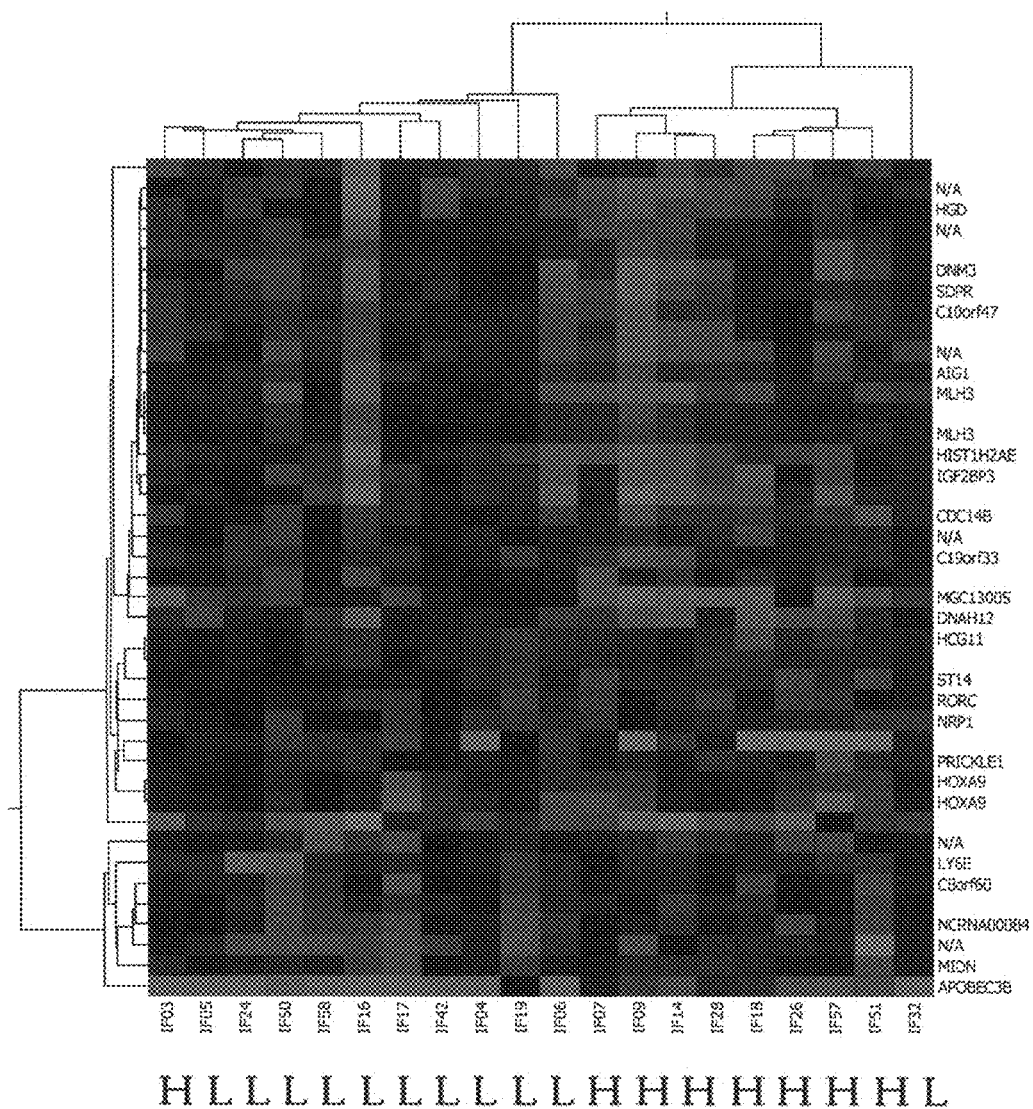
FIG. 12 is a heatmap of gene expression analysis of high and low-flaring patients at non-flaring visit. Low-flaring patients are denoted as "L", and high-flaring patients are denoted as "H".

Additionally, as shown in FIG. 12, unsupervised hierarchical clustering of SLE patients based on the level of 41 deregulated transcripts between high and low flaring patient's groups. The red color of tree correspond to low flaring SLE patients (labeled as L), the green tree color correspond to highly flaring SLE patients (labeled as H).

TABLE 16

Disease Manifestations and SLEDAI > 4 of high and low flaring SLE patients

|  | High (11) | Low (11) | P value |
| --- | --- | --- | --- |
| Malar rash | 7 (64%) | 4 (36%) | N/S |
| Discoid | 3 (27%) | 1 (9%) | N/S |
| Photosensitivity | 6 (55%) | 2 (18%) | 0.091 |
| Ulceration | 6 (55%) | 3 (27%) | N/S |
| Arthritis | 10 (91%) | 10 (91%) | N/S |
| Serositis | 7 (64%) | 2 (18%) | 0.04 |
| Renal | 5 (45%) | 7 (64%) | N/S |
| Neurological | 2 (18%) | 3 (27%) | N/S |
| Hematological | 7 (64%) | 6 (55%) | N/S |
| Immunological | 10 (91%) | 9 (82%) | N/S |
| ANA | 10 (91%) | 11 (100%) | N/S |
| SLEDAI2K ≥4 visits/year | 4.9 (±1.8) | 1.5 (±1.8) | <0.01* |
| Average oral prednisone ≥8 mg/day | 8 (73%) | 3 (27%) | 0.04 |
| Average C3 level, mg/dl | 72 (±11) | 97 (±22) | <0.01* |

Additional genes that could be useful as biomarkers for future flares are listed in Table 17. These transcripts were different between high and low flaring SLE patients at non-flare visits.

TABLE 17

Gene Candidates for Biomarkers for Future Flares

| Probe Set ID | Gene Symbol | Gene Title | Hi vs Low | p values |
| --- | --- | --- | --- | --- |
| 206632_s_at | APOBEC3B | apolipoprotein B mRNA editing enzyme (3B) | 3.9 | 0.0102 |
| 234989_at | NCRNA00084 | non-protein coding RNA 84 | 1.8 | 0.0005 |
| 202145_at | LY6E | lymphocyte antigen 6 complex, locus E | 1.6 | 0.0162 |
| 225954_s_at | MIDN | midnolin | 1.5 | 0.0098 |
| 220712_at | C8orf60 | chromosome 8 open reading frame 60 | 1.5 | 0.0092 |
| 228806_at | RORC | RAR-related orphan receptor C | 0.7 | 0.0047 |
| 230708_at | PRICKLE1 | prickle homolog 1 (*Drosophila*) | 0.7 | 0.0014 |
| 209905_at | HOXA9 | homeobox A9 | 0.7 | 0.0064 |
| 201280_s_at | DAB2 | disabled homolog 2, mitogen-responsive phosphoprotein | 0.7 | 0.0278 |
| 208022_s_at | CDC14B | CDC14 cell division cycle 14 homolog B | 0.7 | 0.0367 |
| 235121_at | ZNF542 | zinc finger protein 542 | 0.6 | 0.0074 |
| 216905_s_at | ST14 | suppression of tumorigenicity 14 (colon carcinoma) | 0.6 | 0.0005 |
| 218711_s_at | SDPR | serum deprivation response (phosphatidylserine b. protein) | 0.6 | 0.0422 |
| 212298_at | NRP1 | neuropilin 1 | 0.6 | 0.0041 |
| 217216_x_at | MLH3 | mutL homolog 3 (*E. coli*) | 0.6 | 0.0006 |
| 203819_s_at | IGF2BP3 | insulin-like growth factor 2 mRNA binding protein 3 | 0.6 | 0.0236 |
| 214651_s_at | HOXA9 | homeobox A9 | 0.6 | 0.0153 |
| 214469_at | HIST1H2AE | histone cluster 1, H2ae | 0.6 | 0.0348 |
| 214307_at | HGD | homogentisate 1,2-dioxygenase (homogentisate oxidase) | 0.6 | 0.0449 |
| 1557167_at | HCG11 | HLA complex group 11 | 0.6 | >0.0001 |
| 1557169_x_at | HCG11 | HLA complex group 11 | 0.6 | >0.0001 |
| 243802_at | DNAH12 | dynein, axonemal, heavy chain 12 | 0.6 | 0.04 |
| 223631_s_at | C19orf33 | chromosome 19 open reading frame 33 | 0.6 | 0.0097 |
| 230051_at | C10orf47 | chromosome 10 open reading frame 47 | 0.6 | 0.0316 |
| 230520_at | AIG1 | androgen-induced 1 | 0.6 | 0.012 |
| 1554918_a_at | ABCC4 | ATP-binding cassette, sub-family C member 4 | 0.6 | 0.0151 |
| 208180_s_at | HIST1H4B | Histone cluster 1, H4b | 0.5 | 0.0459 |
| 209839_at | DNM3 | dynamin 3 | 0.5 | 0.0255 |
| 220496_at | CLEC1B | C-type lectin domain family 1, member B | 0.5 | 0.0401 |

TABLE 17-continued

Gene Candidates for Biomarkers for Future Flares

| Probe Set ID | Gene Symbol | Gene Title | Hi vs Low | p values |
|---|---|---|---|---|
| 223777_at | MGC13005 | hypothetical LOC84771 | 0.4 | 0.0071 |
| 203290_at | HLA-DQA1 | major histocompatibility complex, class II, DQ alpha 1 | 0.2 | 0.0118 |

REFERENCES

Abramson et al. (1983) *Arthritis Rheum.* 26:630-6
American College of Rheumatology Ad Hoc Committee on Systemic Lupus Erythematosus Response Criteria (2004) *Arthritis Rheum.* 50:3418-26
Ausubel et al. (1994) *Current Protocols in Molecular Biology*
Baechler et al. (2003) *Proc Natl Acad Sci USA* 100:2610-5
Barrat et al. (2005) *J. Exp. Med.* 202:1131-9
Bates and Maechler (2009) "Sparse Matrices in package Matrix and applications" Seminar for Statistics, useR! 2009, Rennes, Jul. 10, 2009
Bauer et al. (2009) *Arthritis Rheum.* 60:3098-107
Bennett et al. (2003) *J. Exp. Med.* 197:711-23
Brinkmann et al. (2004) *Science* 303:1532-5
Chaussabel et al. (2008) *Immunity* 29:150-64
Crow and Kirou (2008) *Arthritis Res. Ther.* 10:126
Crow (2007) *Curr. Top. Microbiol. Immunol.* 316:359-86
Crow and Wohlgemuth (2003) *Arthritis Res. Ther.* 5:279-87
Crow et al. (2003) *Autoimmunity* 36:481-90
Denny et al. (2010) *J. Immunol.* 6:3284-97
de Waard et al. (1999) *Gene* 226:1-8
Fan et al. (2004) *Genome Res.* 14:878-85
Feng et al. (2006) *Arthritis Rheum.* 54:2951-62
Forsman and Dahlgren (2010) *BMC Cell Biol.* 11:52
Fukuda et al. (2009) *Clin. Rheumatol.* 28:301-4
Garcia-Carrasco et al. (2002) *J. Rheumatol.* 29:726-30.
Garcia-Romo et al. (2011) *Sci. Trans. Med.* 3:73ra20
Gray et al. (2010) *J. Immunol.* 184:6359-66
Hakkim et al. (2010) *Proc Natl Acad Sci USA* 107:9813-8
Han et al. (2003) *Genes Immun.* 4:177-86
Hargraves et al. (1948) *Mayo Clin. Proc.* 23:25-8
Hargraves (1969) *Mayo Clin. Proc.* 44:579-9
Irizarry et al. (2003) *Biostatistics* 4:249-64
Karlovich et al. (2009) *BMC Med. Genomics.* 2:33
Kirou et al. (2004) *Arthritis Rheum.* 50:3958-67
Kriegler (1990) *Gene Transfer and Expression: A Laboratory Manual*
Kurien and Scofield (2006) *Scand. J. Immunol.* 64:227-35.
Kurien et al. (2000) *Clin. Exp. Immunol.* 120:209-17
Lande et al. (2011) *Sci. Transl. Med.* 3:73ra19
Lovgren et al. (2004) *Arthritis Rheum.* 50:1861-72
Mantovani et al. (1998) *Ann. N Y Acad. Sci.* 840:338-51
Milner and Day (2003) *J. Cell. Sci.* 116:1863-73.
Nathan (2006) *Nat. Rev. Immunol.* 6:173-82
Samarajiwa et al. (2009) *Nucleic Acids Research* (Database Issue):D852-7
Sambrook et al. (1989) *Molecular Cloning, A Laboratory Manual*
Tan et al. (1982) *Arthritis Rheum.* 25:1271-7
Theilgaard-Mönch et al. (2005) *Blood* 105:1785-96
Velculescu et al. (1995) *Science* 270:484-487
Velculescu et al. (1997) *Cell* 88
Villanueva et al. (2011) *J. Immunol.* 187:538-52
Yee et al. (2009) *Rheumatology* 48:691-5
Zhao et al. (2009) *Drug Metab. Dispos.* 37:282-91

The invention claimed is:

1. A method of detecting a flare of systemic lupus erythematosus (SLE) in a subject diagnosed with SLE, consisting of:
   a. assaying gene expression levels of IFIT3, MMP8, CD38, and KLRB1 in a sample of blood from the subject, wherein assaying the gene expression levels is performed using a method comprising at least one of: PCR, RNA sequencing, or microarray;
   b. comparing the gene expression levels of IFIT3, MMP8, CD38, and KLRB1 in the sample from the subject with reference gene expression levels of IFIT3, MMP8, CD38, and KLRB1 in a sample of blood from a first healthy control;
   c. assaying for the level of vWF in a sample of blood from the subject, wherein assaying for vWF is performed using a method comprising at least one of: ELISA, western blot, immunoblot, quantitative mass spectrometry, radioimmunoassay, immunoradiometric assay, or immunoenzymatic assay;
   d. comparing the level of vWF with a reference level of vWF in a sample of blood from the first or a second healthy control; and
   e. determining that the subject is having a flare of SLE when the levels of IFIT3, MMP8, CD38, and vWF from the subject are increased and the level of KLRB1 from the subject is decreased as compared to the reference levels.

2. The method of claim 1, wherein the subject is human.

3. A method of determining the effectiveness of a treatment for systemic lupus erythematosus (SLE) consisting of:
   a. assaying gene expression levels of IFIT3, MMP8, CD38, and KLRB1 in a sample of blood from a subject who has received the treatment for SLE, wherein assaying the gene expression levels is performed using a method comprising at least one of: PCR, RNA sequencing, or microarray;
   b. comparing the gene expression levels of IFIT3, MMP8, CD38, and KLRB1 in the sample from the subject with reference gene expression levels of IFIT3, MMP8, CD38, and KLRB1 obtained from the subject prior to the treatment;
   c. assaying for the level of vWF in a sample of blood from the subject, wherein assaying for vWF is performed using a method comprising at least one of: ELISA, western blot, immunoblot, quantitative mass spectrometry, radioimmunoassay, immunoradiometric assay, or immunoenzymatic assay;
   d. comparing the level of vWF with a reference level of vWF in a sample of blood obtained from the subject prior to the treatment; and e. determining the treatment as being effective for treating SLE when the levels of IFIT3, MMP8, CD38, and vWF from the subject are decreased and the level of KLRB1 from the subject is increased as compared to the reference levels.

4. The method of claim 3, wherein the subject is human.

5. A method of detecting increased risk of future flares of systemic lupus erythematosus (SLE) in a subject diagnosed with SLE, consisting of:
   a. assaying gene expression levels of IFIT3, MMP8, CD38, and KLRB1 in a sample of blood from the subject, wherein assaying the gene expression levels is performed using a method comprising at least one of: PCR, RNA sequencing, or microarray;
   b. comparing the gene expression levels of IFIT3, MMP8, CD38, and KLRB1 in the sample from the subject with reference gene expression levels of IFIT3, MMP8, CD38, and KLRB1 in a sample of blood from a first healthy control;
   c. assaying for the level of vWF in a sample of blood from the subject, wherein assaying for the vWF is performed using a method comprising at least one of ELISA, western blot, immunoblot, quantitative mass spectrometry, radioimmunoassay, immunoradiometric assay, or immunoenzymatic assay;
   d. comparing the level of vWF with a reference level of vWF in a sample of blood from the first or a second healthy control;
   e. determining that the subject has an increased risk of future flares of SLE when the levels of IFIT3, MMP8, CD38, and vWF from the subject are increased and the level of KLRB1 from the subject is decreased as compared to the reference levels.

6. The method of claim 5, wherein the subject is human.

* * * * *